United States Patent
Ichikawa et al.

(10) Patent No.: US 8,617,790 B2
(45) Date of Patent: Dec. 31, 2013

(54) PHOTORESIST COMPOSITION AND METHOD FOR PRODUCING PHOTORESIST PATTERN

(75) Inventors: Koji Ichikawa, Osaka (JP); Yukako Anryu, Osaka (JP); Shingo Fujita, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/448,591

(22) Filed: Apr. 17, 2012

(65) Prior Publication Data
US 2012/0270153 A1 Oct. 25, 2012

(30) Foreign Application Priority Data
Apr. 20, 2011 (JP) ................................. 2011-093814

(51) Int. Cl.
*G03F 7/004* (2006.01)
*G03F 7/028* (2006.01)
*G03F 7/039* (2006.01)

(52) U.S. Cl.
USPC .......................... 430/270.1; 430/326; 430/925

(58) Field of Classification Search
USPC ............... 430/270.1, 326, 910, 921, 923, 925
See application file for complete search history.

(56) References Cited

U.S. PATENT DOCUMENTS

| | | | |
|---|---|---|---|
| 2006/0194982 A1 | 8/2006 | Harada et al. | |
| 2007/0027336 A1 | 2/2007 | Yoshida et al. | |
| 2007/0122750 A1 | 5/2007 | Yamaguchi et al. | |
| 2008/0081293 A1 | 4/2008 | Harada et al. | |
| 2011/0020749 A1* | 1/2011 | Ichikawa et al. | ........... 430/270.1 |

FOREIGN PATENT DOCUMENTS

JP        2010-224530        * 10/2010

OTHER PUBLICATIONS

Machine translation of JP 2010-224530, published on Oct. 7, 2010.*

* cited by examiner

*Primary Examiner* — Anca Eoff
(74) *Attorney, Agent, or Firm* — Birch, Stewart, Kolasch & Birch, LLP

(57) ABSTRACT

A photoresist composition comprising
(A) a resin which has an acid-labile group-containing structural unit and a lactone ring-containing structural unit, and
(B) a salt represented by formula (I):

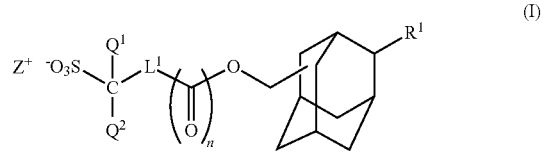

wherein $Q^1$ and $Q^2$ each independently represent a fluorine atom or a C1-C6 perfluoroalkyl group,
n represents 0 or 1,
$L^1$ represents a single bond or a C1-C10 alkanediyl group in which a methylene group may be replaced by an oxygen atom or a carbonyl group, provided that $L^1$ is not a single bond when n is 0,
$R^1$ represents a hydroxy group or a hydroxy group protected by a protecting group, and
$Z^+$ represents an organic cation.

12 Claims, No Drawings

PHOTORESIST COMPOSITION AND METHOD FOR PRODUCING PHOTORESIST PATTERN

This nonprovisional application claims priority under 35 U.S.C. §119 (a) on Patent Application No. 2011-093814 filed in JAPAN on Apr. 20, 2011, the entire contents of which are hereby incorporated by reference.

FIELD OF THE INVENTION

The present invention relates to a photoresist composition and a method for producing a photoresist pattern.

BACKGROUND OF THE INVENTION

A photoresist composition is used for semiconductor microfabrication employing a lithography process, which contains resin which has an acid-labile group, a solvent and an acid generator comprising a salt.

US2007/122750A1 mentions a photoresist composition comprising:
a resin which has a structural unit represented by formula (a1-1-2),
a structural unit represented by formula (a2-1-1) and a structural unit represented by formula (a3-1-1),
a salt represented by formula (B1), and
a solvent.

US2006/194982 mentions a photoresist composition comprising the resin as mentioned above, a salt represented by formula (B2), and a solvent.

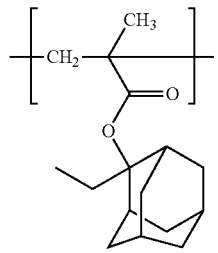

(a1-1-2)

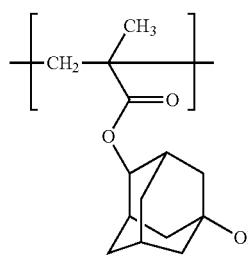

(a2-1-1)

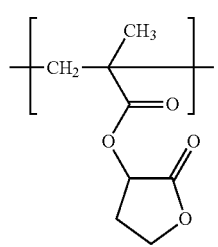

(a3-1-1)

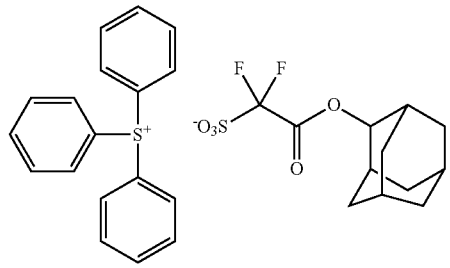

(B1)

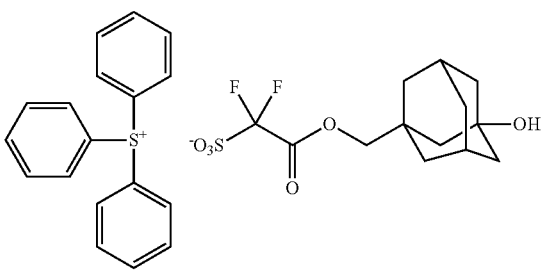

(B2)

SUMMARY OF THE INVENTION

The present invention is to provide a photoresist composition suitable for a lithography process.

The present invention relates to the followings:

<1> A photoresist composition comprising
(A) a resin which has an acid-labile group-containing structural unit and a lactone ring-containing structural unit, and
(B) a salt represented by formula (I):

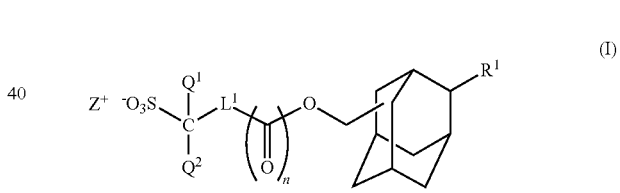

(I)

wherein $Q^1$ and $Q^2$ each independently represent a fluorine atom or a C1-C6 perfluoroalkyl group,
n represents 0 or 1,
$L^1$ represents a single bond or a C1-C10 alkanediyl group in which a methylene group may be replaced by an oxygen atom or a carbonyl group, provided that $L^1$ is not a single bond when n is 0,
$R^1$ represents a hydroxy group or a hydroxy group protected by a protecting group, and
$Z^+$ represents an organic cation.

<2> The photoresist composition according to <1>, which further comprises a solvent.

<3> The photoresist composition according to <1> or <2>, wherein n is 1.

<4> The photoresist composition according to <1>, <2> or <3>, wherein $L^1$ is a single bond.

<5> The photoresist composition according to any one of <1> to <4>, wherein $R^1$ is a hydroxy group.

<6> The photoresist composition according to any one of <1> to <5>, wherein $R^1$ is a hydroxy group protected by a protecting group, and is represented by formula (2A).

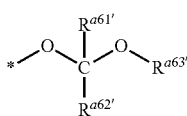

(2A)

wherein $R^{a61'}$ and $R^{a62'}$ independently each represent a hydrogen atom or a C1-C12 monovalent hydrocarbon group, and $R^{a63'}$ represents a C1-C20 monovalent hydrocarbon group, or $R^{a63'}$ represents a C2-C20 divalent hydrocarbon group together with $R^{a62'}$, and a methylene group of the monovalent hydrocarbon groups may be replaced by an oxygen atom or a sulfur atom, and a methylene group of the divalent hydrocarbon groups may be replaced by an oxygen atom or a sulfur atom.

<7> The photoresist composition according to any one of <1> to <6>, wherein $Z^+$ is an arylsulfonium cation.

<8> The photoresist composition according to any one of <1> to <7> wherein the lactone ring-containing structural unit is represented by formula (a3-1), formula (a3-2) or formula (a3-3):

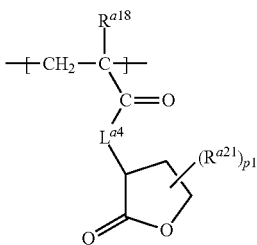

(a3-1)

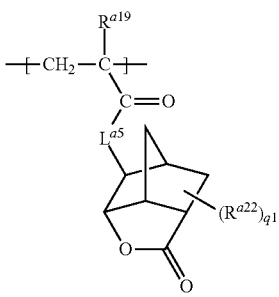

(a3-2)

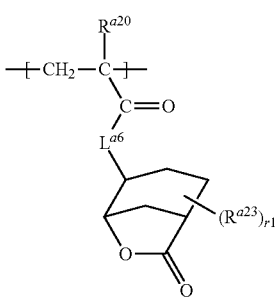

(a3-3)

wherein $L^{a4}$, $L^{a5}$ and $L^{a6}$ each independently represent *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

<9> The photoresist composition according to <8> wherein the lactone ring-containing structural unit is represented by formula (a3-2) wherein $L^{a5}$ represents *—O—$(CH_2)_{k3}$—CO—O— in which * represents a binding position to —CO— and k3 represents an integer of 1 to 7, and q1 is 0.

<10> The photoresist composition according to any one of <1> to <9> wherein the acid-labile group-containing structural unit is represented by formula (a1-1) or formula (a1-2):

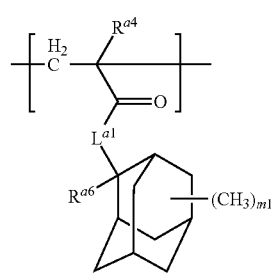

(a1-1)

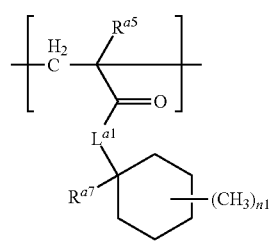

(a1-2)

wherein $L^{a1}$ and $L^{a2}$ each independently represent *—O— or *—O—$(CH_2)_{k1}$—CO—O— in which * represents a binding position to —CO—, and k1 represents an integer of 1 to 7, $R^{a4}$ and $R^{a5}$ each independently represent a hydrogen atom or a methyl group, $R^{a6}$ and $R^{a7}$ each independently represent a C1-C10 aliphatic hydrocarbon group, m1 represents an integer of 0 to 14, and n1 represents an integer of 0 to 10.

<11> The photoresist composition according to any one of <1> to <10> wherein the resin further comprises a hydroxyadamantan-1-yl group-containing structural unit.

<12> The photoresist composition according to any one of <1> to <11> which further comprises a resin comprising a structural unit represented by formula (a4-1):

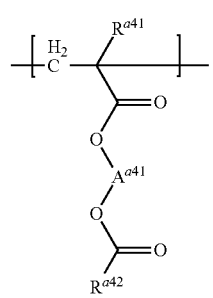

(a4-1)

wherein $R^{a41}$ represents a C6-C12 monovalent aromatic hydrocarbon group, or a C1-C12 monovalent aliphatic hydrocarbon group in which a methylene group may be replaced by an oxygen atom or a carbonyl group, $A^{a41}$ represents a C1-C6 alkanediyl group, or a moiety represented by formula (a-g1):

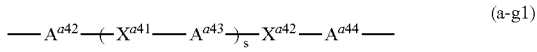

in which s represents 0 or 1, $A^{a42}$ and $A^{a44}$ respectively represent a C1-C5 aliphatic hydrocarbon group which may have a substituent, $A^{a43}$ represents a single bond or a C1-C5 aliphatic hydrocarbon group which may have a substituent, $X^{a41}$ and $X^{a42}$ respectively represent —O—, —CO—, —CO—O—, or —O—CO—, the total number of carbon atoms of $A^{a42}, A^{a43}, A^{a44}, X^{a41}$ and $X^{a42}$ is not more than 6,
$R^{a42}$ represents an aliphatic hydrocarbon group which may have a substituent.

<13> The photoresist composition according to any one of <1> to <12>, which further comprises a basic compound.
<14> A process for producing a photoresist pattern comprising the following steps (1) to (5):
(1) a step of applying the photoresist composition according to any one of <1> to <13> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.
<15> A process for producing a compound represented by formula (I-a):

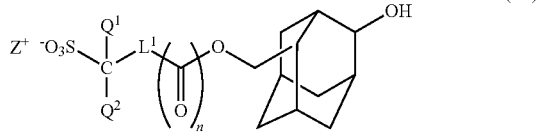

wherein $Q^1$ and $Q^2$ each independently represent a fluorine atom or a C1-C6 perfluoroalkyl group,
n represents 0 or 1,
$L^1$ represents a single bond or a C1-C10 alkanediyl group in which a methylene group may be replaced by an oxygen atom or a carbonyl group, provided that $L^1$ is not a single bond when n is 0, and $Z^+$ represents an organic cation,
which method comprises reducing a compound represented by formula (I-b):

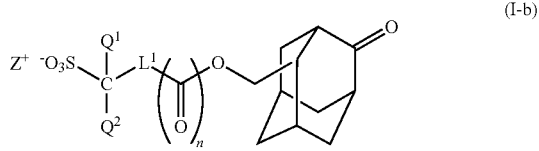

wherein $Q^1$, $Q^2$, n, $L^1$ and $Z^+$ are defined as above.

DESCRIPTION OF PREFERRED EMBODIMENTS

The photoresist composition of the present invention will be illustrated.
The photoresist composition of the present invention comprises a resin (A) which has an acid-labile group-containing structural unit and a lactone ring-containing structural unit, if necessary together with a resin (X) which has another specific structural unit described bellow.

The resin (A) has an acid-labile group-containing structural unit and a lactone ring-containing structural unit. The resin (A) has an acid-labile group derived from an acid-labile group-containing structural unit and a lactone ring derived from a lactone ring-containing structural unit, at its side chain.

With an acid-labile group-containing structural unit, the resin (A) is insoluble or poorly soluble in an aqueous alkali solution but becoming soluble in an aqueous alkali solution by the action of an acid. In other words, the resin is insoluble or poorly soluble in an aqueous alkali solution if it has not been contacted with an acid. The resin after being contacted with an acid can be soluble in an aqueous alkali solution. The resin (A) has one or more acid-labile groups.

Herein "an acid-labile group" refers to a group capable of being cleaved in case of contacting with an acid to give a hydrophilic group such as a hydroxy group or carboxy group.

Specific examples of the acid-labile group include a group represented by the formula (1):

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group, and * represents a binding position, and a group represented by the formula (2)

wherein $R^{a1'}$ and $R^{a2'}$ independently each represent hydrogen atom or a C1-C12 hydrocarbon group, and $R^{a3'}$ represents a C1-C20 monovalent hydrocarbon group, or Ra3' together with $R^{a1'}$ and $R^{a2'}$ represents a C2-C20 divalent hydrocarbon group in which a methylene group of the divalent hydrocarbon group may be replaced by —O— or —S—.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic. Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings.

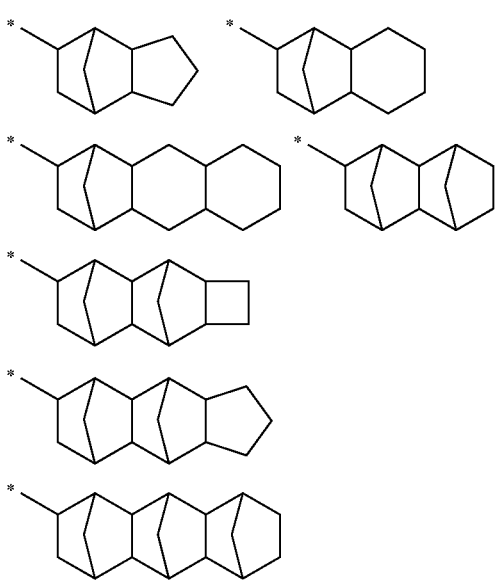

The alicyclic hydrocarbon group preferably has 3 to 16 carbon atoms.

When $R^{a1}$ and $R^{a2}$ of formula (1) are bonded each other to form a C2-C20 divalent hydrocarbon group, the moiety represented by —C($R^{a1}$) ($R^{a2}$) ($R^{a3}$) includes the following groups and the ring preferably has 3 to 12 carbon atoms.

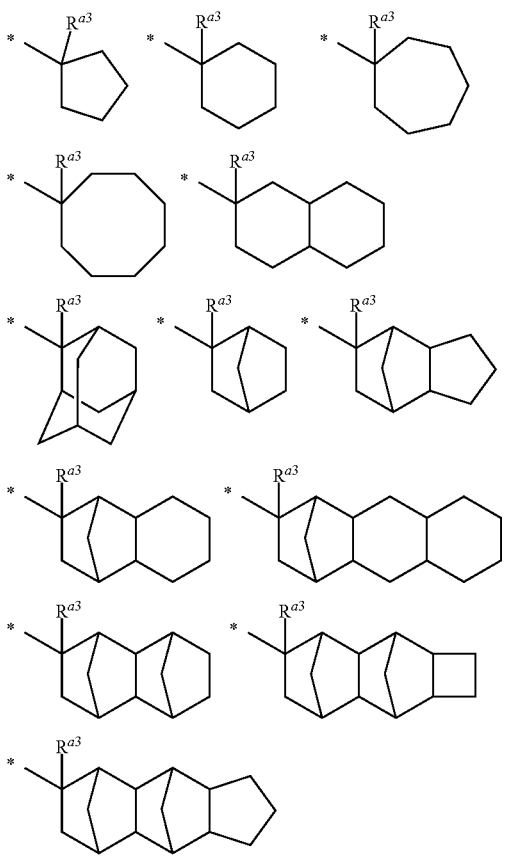

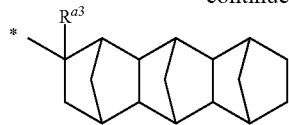

-continued wherein $R^{a3}$ is the same as defined above and * represents a binding position to —O— of formula (1).

The group represented by the formula (1) wherein $R^{a1}$, $R^{a2}$ and $R^{a3}$ independently each represent a C1-C8 alkyl group such as a tert-butyl group, such as 1,1'-dialkylalkoxylcarbonyl group, the group represented by the formula (1) where in $R^{a1}$ and $R^{a2}$ are bonded each other to form an adamantyl ring and $R^{a3}$ is a C1-C8 alkyl group such as a 2-alkyladaman-2-tyloxycarbonyl group, and the group represented by the formula (1) wherein $R^{a1}$ and $R^{a2}$ are C1-C8 alkyl groups and $R^{a3}$ is an adamantin-1-yl group such as a 1-(1-adaman-1-yl)-1-alkylalkoxycarbonyl group are preferable.

As to formula (2), examples of the hydrocarbon group include an alkyl group, an alicyclic hydrocarbon group and an aromatic hydrocarbon group.

Examples of the alkyl group and the alicyclic hydrocarbon group include the same as described above. Examples of the aromatic hydrocarbon group include an aryl, group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{a1'}$ and $R^{a2'}$ is a hydrogen atom.

Examples of the group represented by formula (2) include the following.

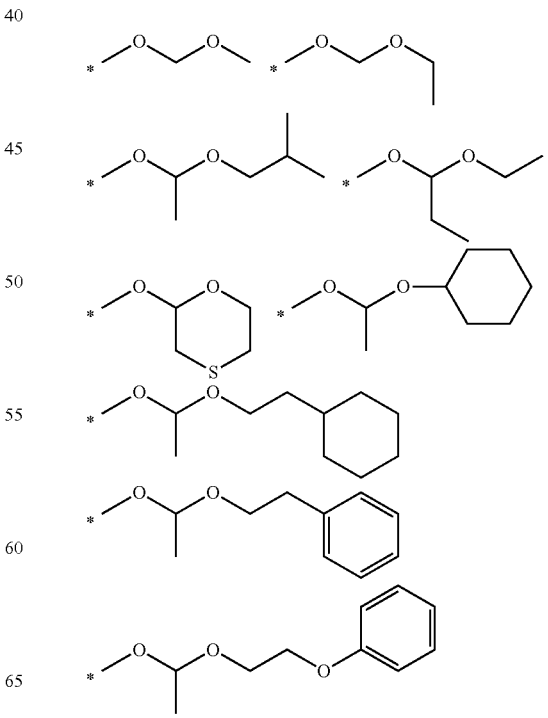

-continued

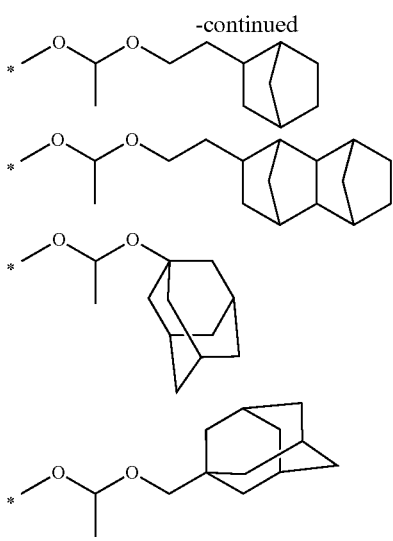

The acid-labile group-containing structural unit is preferably a structural unit derived from a compound having an acid-labile group in its side chain and a carbon-carbon double bond, and is more preferably a structural unit derived from a methacryalte compound having an acid-labile group in its side chain.

Preferable resin (A) has a structural unit represented by the formula (a1-1) or (a1-2) as the acid-labile group-containing structural unit:

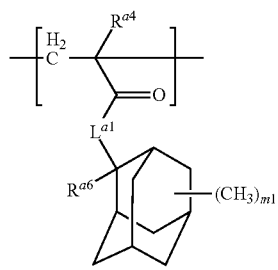

(a1-1)

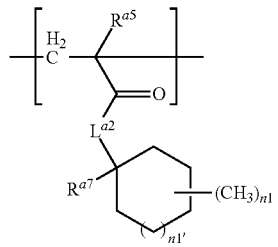

(a1-2)

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents —O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 to 3.

Examples of the aliphatic hydrocarbon group include a C1-C10 alkyl group such as a methyl group, an ethyl group, a propyl group, an isopropyl group, a butyl group, a tert-butyl group, 2,2-dimethylethyl group, 1-methylpropyl group, 2,2-dimethylpropyl group, 1-ethylpropyl group, 1-methylbutyl group, 2-methylbutyl group, 3-methylbutyl group, 1-propylbutyl group, a pentyl group, 1-methylpentyl group, a hexyl, group, 1,4'-dimethylhexyl group, a heptyl group, 1-methylheptyl group and an octyl group; and the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

The alkyl group has preferably 1 to 8 carbon atoms, more preferably 1 to 6 carbon atoms, and the saturated cyclic hydrocarbon group preferably has 3 to 10 carbon atoms and more preferably 3 to 6 carbon atoms.

$L^{a1}$ and $L^{a2}$ are preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

$R^{a4}$ and $R^{a5}$ are preferably methyl groups.

Particularly when the photoresist composition contains a resin derived from a monomer having a bulky structure such as a saturated alicyclic hydrocarbon group, the photoresist composition having excellent resolution tends to be obtained.

As the structural unit represented by the formula (a1-1) preferred are structural units represented by formulae (a1-1-1), (a1-1-2) (a1-1-3), (a1-1-4), (a1-1-5), (a1-1-6), (a1-1-7) and (a1-1-8), more preferred are structural units represented by formulae (a1-1-1), (a1-1-2), (a1-1-3) and (a1-1-4), and still more preferred are structural units represented by formulae (a1-1-2) and (a1-1-3).

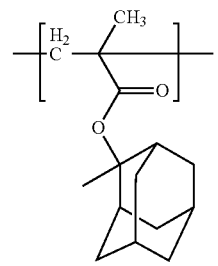

(a1-1-1)

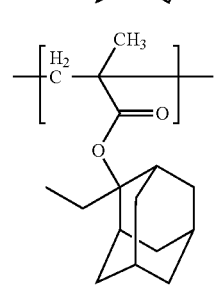

(a1-1-2)

(a1-1-3)
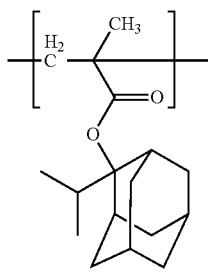

(a1-1-4)
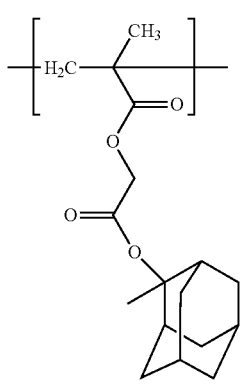

(a1-1-5)
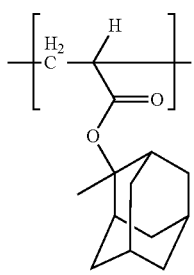

(a1-1-6)
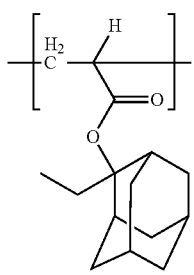

(a1-1-7)
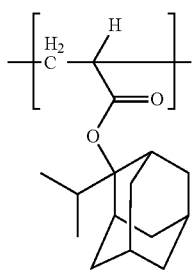

(a1-1-8)
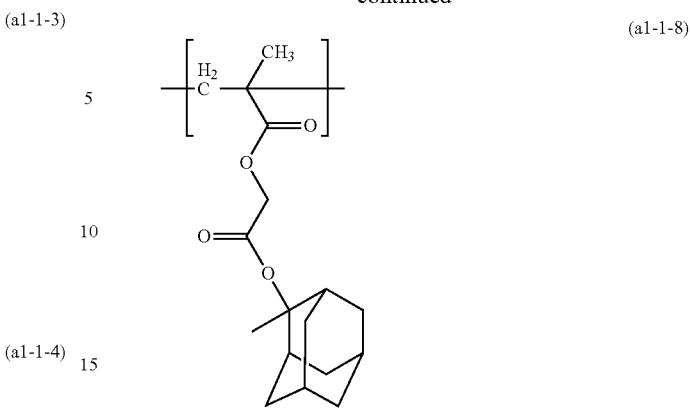

Structural units represented by the formula (a1-1) include compounds mentioned in JP2010-204646A.

Examples of structural units represented by the formula (a1-2) include 1-ethyl-cyclopentant-1-yl(meth)acrylate, 1-ethyl-cyclohexan-1-yl(meth)acrylate, 1-ethyl-cyclohept-1-yl (meth)acrylate, 1-methyl-cyclopent-1-yl(meth)acrylate, and 1-isopropyl-cyclopent-1-yl(meth)acrylate.

As the structural unit represented by the formula (a1-2), preferred are those represented by formulae (a1-2-1), (a1-2-2), (a1-2-3), (a1-2-4), (a1-2-5) and (a1-2-6), more preferred are those represented by formulae (a1-2-1), (a1-2-2), (a1-2-3) and (a1-2-4).

(a1-2-1)
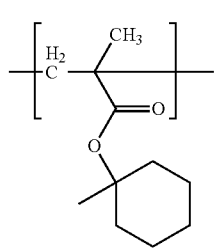

(a1-2-2)
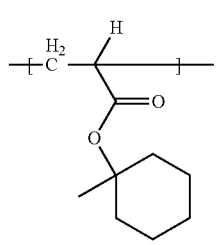

(a1-2-3)
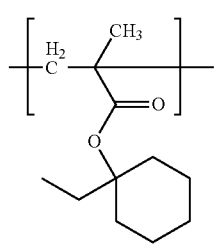

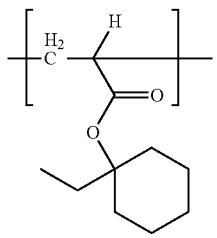 (a1-2-4)

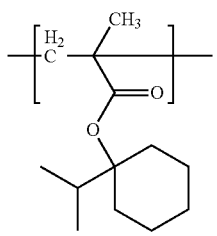 (a1-2-5)

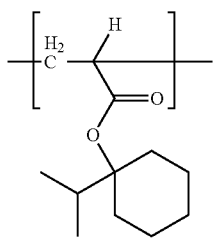 (a1-2-6)

The content of the acid-labile group-containing structural unit in the resin is usually 10 to 95% by mole, preferably 15 to 90% by mole and more preferably 20 to 85% by mole based on 100% by mole of all the structural units of the resin (A).

The content of the structural unit represented by the formula (a1-1) and/or (a1-2) in the resin is usually 10 to 95% by mole, preferably 15 to 90% by mole, and more preferably 20 to 85% by mole based on 100% by mole of all the structural units of the resin (A). When the resin (A) has an adamantane ring-containing structural unit, preferably the structural unit represented by formula (a1-1) as the acid-labile group-containing structural unit, the content of the structural unit represented by the formula (a1-1) is preferably 15 to 90% by mole and more preferably 20 to 85% by mole based on 100% by mole of all the acid-labile group-containing structural unit. When the resin (A) has an adamantane ring-containing structural, unit in such amount as mentioned above, the photoresist pattern obtained from the photoresist composition of the present invention can have more improved resistance to dry-etching.

As another example of the acid-labile group-containing structural unit include a unit derived from a (meth) acryl compound represented by the formula (a-5).

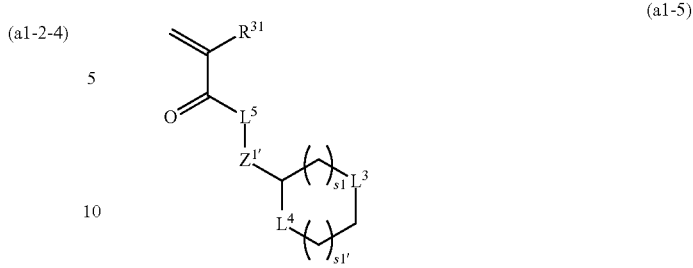 (a1-5)

wherein $R^{31}$ represents a hydrogen atom, a halogen atom, or a C1-C6 alkyl group having a halogen group, $L^3$ and $L^4$ each independently represents —O— or —SO—, $L^5$ represents —O—, —SO— *—O—$(CH_2)_{k4}$—CO—O— in which * represents a binding position to —CO—, and k4 represents an integer of 1 to 7, $Z^1$ represents a single bond or a C1-C6 alkanediyl group in which a methylene group may be replaced by an oxygen atom or a carbonyl group, and s1 and s1' each independently represent an integer of 0 to 4.

In the formula (a-5), $R^{31}$ represents preferably a hydrogen atom, C1-3 alkyl group which may have a fluorine atom, more preferably a hydrogen atom, methyl group, or trifluoromethyl group.

It is preferred that one of $L^3$ and $L^4$ represents —O—, while the other represents —SO—. $L^5$ preferably represents —O—.

s1 preferably represents 1. s1' represents an integer of 0 to 2.

$Z^1$ preferably represents a single bond or —$CH_2$—CO—O—.

The compound represented by the formula (a-5) includes the following ones:

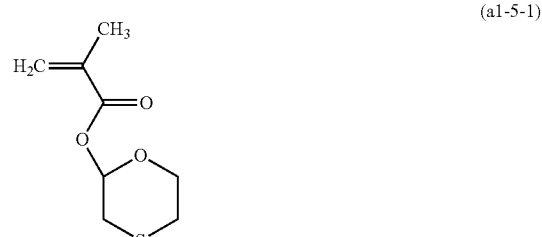 (a1-5-1)

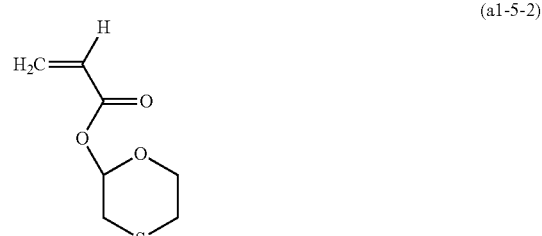 (a1-5-2)

(a1-5-3)

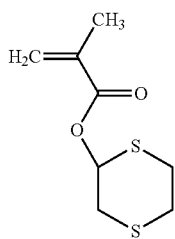

(a1-5-4)

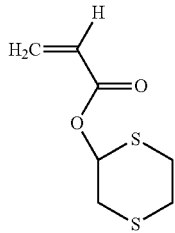

When the resin (A) has a structural unit derived from the compound represented by the formula (a-5), the content of the structural unit is usually 1 to 95% by mole, preferably 3 to 90% by mole and more preferably 5 to 85% by mole based on 100% by mole of all the structural units of the resin.

The resin (A) has a lactone ring-containing structural unit. The lactone ring-containing structural unit is derived from the compound having a lactone ring.

Examples of the lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of lactone ring-containing structural units include those represented by the formulae (a3-1), (a3-2) and (a3-3):

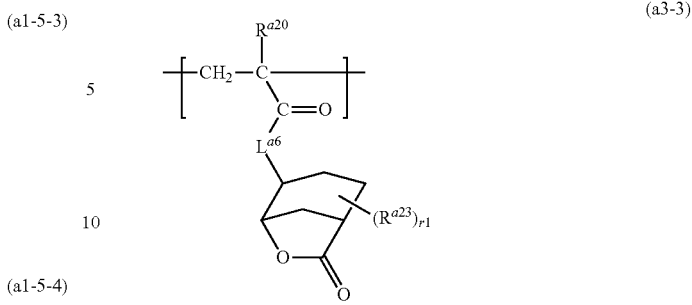

(a3-1)

(a3-2)

(a3-3)

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a hydrogen atom. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Preferred examples of the structural unit represented by the formula (a3-1) include those represented by the formula (a3-1-1), the formula (a3-1-2), the formula (a3-1-3) or the formula (a3-1-4).

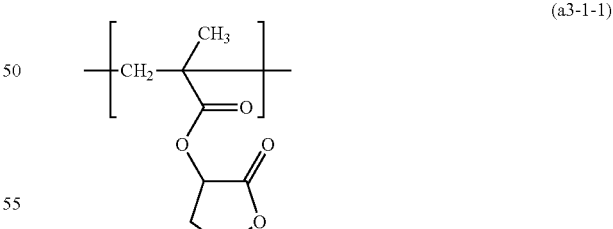

(a3-1-1)

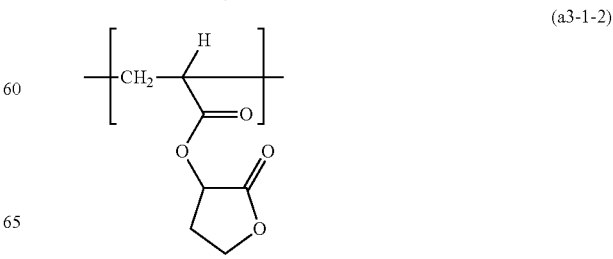

(a3-1-2)

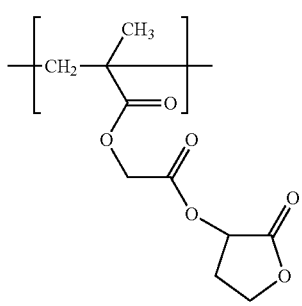
(a3-1-3)

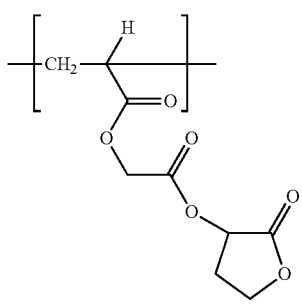
(a3-1-4)

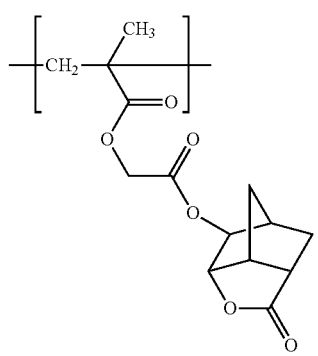
(a3-2-3)

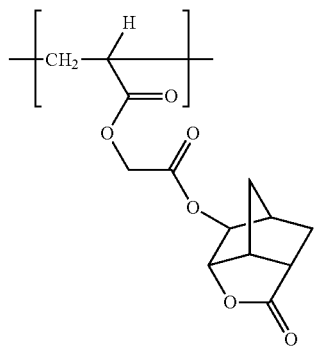
(a3-2-4)

Examples of the structural unit represented by the formula (a3-2) include preferably those represented by the formula (a3-2-1), the formula (a3-2-2), the formula (a3-2-3) or the formula (a3-2-4), and more preferably those represented by the formulae (a3-2) in which $L^{a5}$ represent *—O—CH$_2$—CO—O— in which * represents a binding position to —CO— and q1=1.

Preferred examples of the structural unit represented by the formula (a3-3) include those represented by the formula (a3-3-1), the formula (a3-3-2), the formula (a3-3-3) or the formula (a3-3-4).

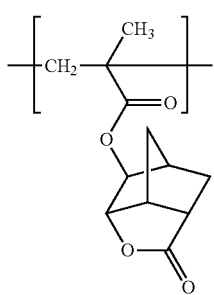
(a3-2-1)

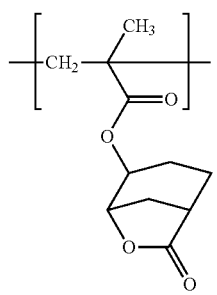
(a3-3-1)

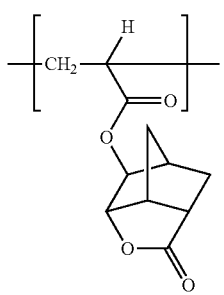
(a3-2-2)

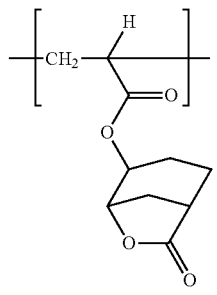
(a3-3-2)

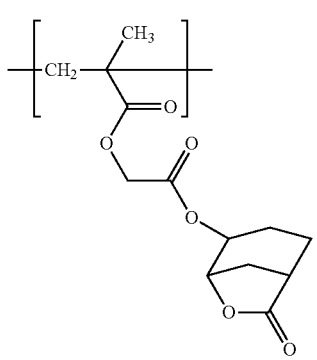

(a3-3-3)

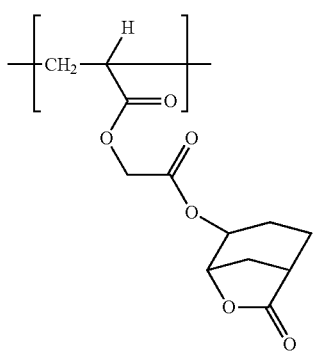

(a3-3-4)

Preferred lactone ring-containing structural unit are those represented by the formulae (a3-1-3), (a3-1-4), (a3-2-1), (a3-2-2), (a3-2-3), (a3-2-4), (a3-3-3) to (a3-3-4), more preferred are those represented by the formulae (a3-2-1), (a3-2-2), (a3-2-3) and (a3-2-4), still more preferred are those represented by the formulae (a3-2-3) and (a3-2-4), especially more preferred are those represented by the formulae (a3-1-3).

Monomers from which the structural units represented by the above formulae are derived are mentioned in JP2010-204646A.

The content of the acid-labile group-containing structural unit is usually 10 to 90% by mole and preferably 20 to 85% by mole based on the total molar of the acid-labile group-containing structural units and the lactone ring-containing structural unit in the resin (A).

The content of the lactone ring-containing structural unit is preferably 10 to 90% by mole, more preferably 15 to 80% by mole, and still more preferably 20 to 70% by mole, based on total molar of all the structural units of the resin. When the resin contains the structural unit represented by the formula (a3-1), formula (a3-2) or formula (a3-3), the content thereof is preferably 5 to 60%, more preferably 5 to 50% by mole and still more preferably 10 to 50% by mole, by mole based on total molar of all the structural units of the resin. When the resin (A) has the structural units in such amounts, a photoresist composition can show adhesiveness of photoresist to a substrate and provide a photoresist pattern with good resolution.

The resin (A) may have a structural unit which has no the lactone ring but which is free of acid-labile groups. Such structural unit is sometimes referred to as "structural unit having no acid-labile group".

Preferred examples of the structural unit having no acid-labile group include a structural unit not having an acid-labile group but having a hydroxy group. Hereinafter, the structural unit not having an acid-labile group but having a hydroxy group is sometimes referred to as "a structural unit having a hydroxy group". When the resin (A) has the structural unit having a hydroxy group, a photoresist composition can show more improved adhesiveness of photoresist to a substrate.

When KrF excimer laser (wavelength: 248 nm) lithography system, or a high energy laser such as electron beam and extreme ultraviolet is used as an exposure system, preferred is a resin which has the structural unit having a phenolic-hydroxy group. When ArF excimer laser (wavelength: 193 nm) is used as an exposure system, preferred is a resin which has the structural unit having represented by the formula (a2-1).

The total content of the lactone ring-containing structural unit and the structural unit having no acid-labile group is preferably 10 to 90% by mole, more preferably 15 to 80% by mole, and still more preferably 20 to 70% by mole, based on total molar of all the structural units of the resin.

The structural unit having a hydroxy group preferably has a hydroxyadamantyl group.

Preferred examples of the structural unit having a hydroxyadamantyl group include a structural unit represented by the formula (a2-1):

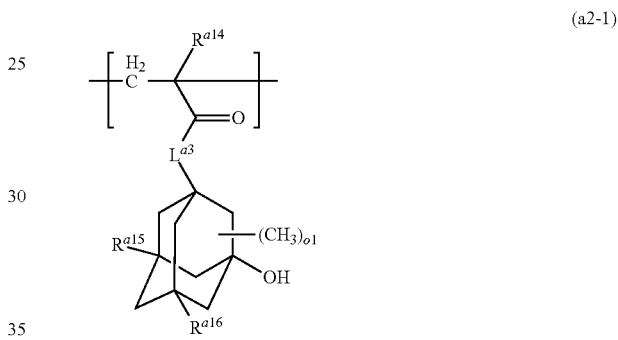

(a2-1)

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

In the formula (a2-1), $R^{a14}$ is preferably a methyl group, $R^{a15}$ is preferably a hydrogen atom, $R^{a16}$ is preferably a hydrogen atom or a hydroxy group, $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

The structural unit represented by the formula (a2-1) includes those represented by the formula as follow:

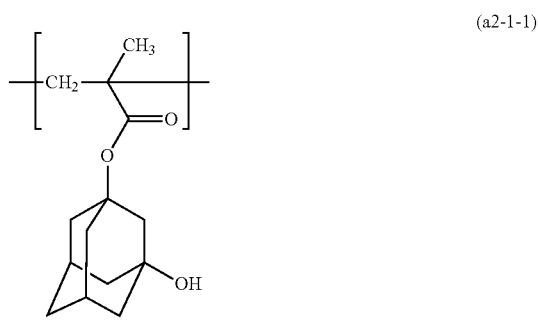

(a2-1-1)

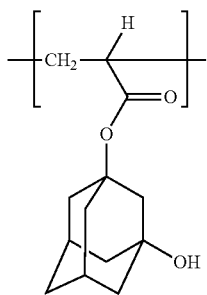
(a2-1-2)

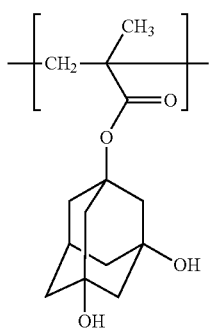
(a2-1-3)

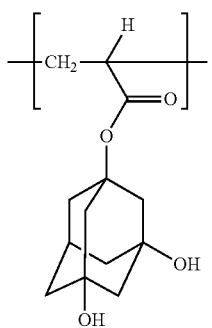
(a2-1-4)

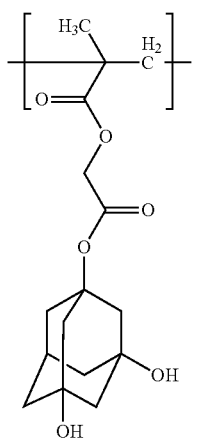
(a2-1-5)

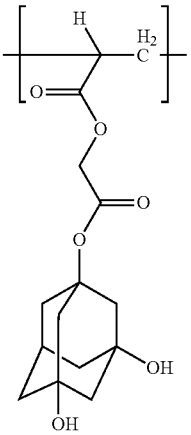
(a2-1-6)

The structural unit represented by formula (a2-1) includes those derived from the compounds mentioned in JP2010-204646A.

Among them, preferred are the structural units represented by formulae (a2-1-1), (a2-1-2), (a2-1-3) and (a2-1-4), more preferred are the structural units represented by formulae (a2-1-1) and (a2-1-3).

When the resin contains the structural unit represented by the formula (a2-1), the content of the structural unit represented by the formula (a2-1) is usually 3 to 45% by mole, and preferably 5 to 40% by mole, and more preferably 5 to 35% by mole, based on total molar of all the structural units of the resin.

Examples of the structural unit having no acid-labile group and having a hydroxy group include one represented by the formula (a2-0):

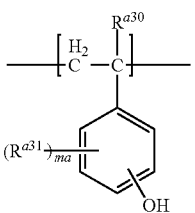
(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, ma represents an integer of 0 to 4.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. $R^{a30}$ represents preferably a C1-C4 alkyl group, more preferably a C1-C2 alkyl group, and still more preferably a methyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group. Examples of the C2-C4 acyl group include an acetyl group, a propionyl group and a butyryl group, and examples of the C2-C4 acyloxy group include an acetyloxy group, a propionyloxy group and a butyryloxy group. $R^{a31}$ represents preferably a C1-C4 alkoxy group, more preferably a C1-C2 alkoxy group, and still more preferably a methoxy group.

In the formula (a2-0), ma is preferably 0, 1 or 2, and is more preferably 0 or 1, and especially preferably 0.

The structural unit represented by the formula (a2-0) is preferably represented by the formulae (a2-0-1) and (a2-0-2). Monomers from which such unit is derived include compounds mentioned in JP2010-204634A.

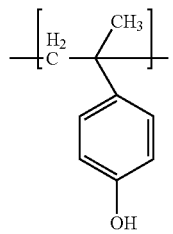

(a2-0-1)

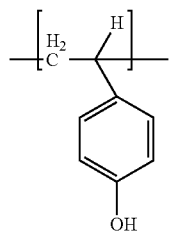

(a2-0-2)

The resin containing the structural unit represented by the formula (a2-0) can be produced, for example, by polymerizing a compound in which a hydroxy group has been protected with a protecting group such as an acetyl group and from which the structural unit represented by the formula (a2-0) is derived, followed by conducting deprotection of the obtained polymer with an acid or a base.

The resin having the structural unit represented by the formula (a2-0) can be produced from a hydroxylstylene as a monomer. Among them, preferred are 4-hydroxystyrene and 4-hydroxy-α-methylstyrene.

When such resin is produced from a hydroxylstylene, it can be produced by protecting a phenolic hydroxy group with an acetyl group to produce acetylhydroxylstylene, polymerizing acetylhydroxylstylene to obtain a resin having the structural unit represented by the formula (a2), followed by deprotecting acetylhydroxy groups of the resin to obtain a resin having the structural unit represented by the formula (a2-0). The deprotection of acetylhydroxy groups requires not remarkably detracting from other structural units such as the unit (a1).

When the resin (A) contains the structural unit represented by the formula (a2-0), the content of the structural unit represented by the formula (a2-0) is usually 10 to 90% by mole and preferably 20 to 85 % by mole and more preferably 30 to 80% by mole based on total molar of all the structural units of the resin.

Examples of the other structural unit having no acid-labile group include the structural units represented by the formula (a4-1):

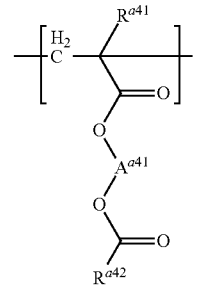

(a4-1)

wherein $R^{a41}$ represents a C6-C12 monovalent aromatic hydrocarbon group, or a C1-C12 monovalent aliphatic hydrocarbon group in which a methylene group may be replaced by an oxygen atom or a carbonyl group, $A^{a41}$ represents a C1-C6 alkanediyl group which may have a substituent, or a moiety represented by formula (a-g1):

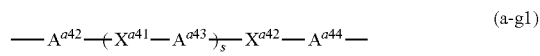

(a-g1)

in which s represents 0 or 1, $A^{a42}$ and $A^{a44}$ respectively represent a C1-C5 alipathic hydrocarbon group which may have a substituent, $A^{a43}$ represents a single bond or a C1-C5 alipathic hydrocarbon group which may have a substituent, $X^{a41}$ and $X^{a42}$ respectively represent —O—, —CO—, —CO—O—, or —O—CO—, the total number of carbon atoms of $A^{a42}$, $A^{a43}$, $A^{a44}$, $X^{a41}$ and $X^{a42}$ is not more than 6, $R^{a42}$ represents an aliphatic hydrocarbon group which may have a substituent and in which a methylene group may be replaced by —C=C—, preferably an aliphatic hydrocarbon group which may have a substituent.

The C1-C5 aliphatic hydrocarbon group includes a C1-C5 alkyl group such as a methyl group, an ethyl group, a propyl group, a butyl group or a pentyl group; C3-C5 alicyclic group; or combined group of the alkyl group and the alicyclic group.

The aliphatic hydrocarbon group of $R^{a42}$ includes a straight or cyclic alkyl group, alicyclic group, and a group comprising the alkyl group and alicyclic group.

The aliphatic hydrocarbon group of $R^{a42}$ is preferably an aliphatic hydrocarbon group which has a substituent.

Such substituent preferably includes a halogen group and a group represented by formula (a-g3):

(a-g3)

in which $X^{a43}$ represents —O—, —CO—, —CO—O—, or —O—CO—, $A^{a45}$ represents C3-C17 aliphatic hydrocarbon group which may have a halogen group. Thus, $R^{a42}$ is preferably represented by formula (a-g2):

(a-g2)

in which $A^{a46}$ respectively represent a C1-C17, preferably C3-C17, alipathic hydrocarbon group which may have a halogen atom, $X^{a44}$ represents —CO—O— or —O—CO—, $A^{a47}$ represents C3-C17 aliphatic hydrocarbon group which may have a halogen group, and the total number of carbon atoms of $A^{a46}$, $X^{a44}$ and $A^{a47}$ is not more than 18.

Hereinafter, the group represented by formula (a-g2) is described. The group represented by formula (a-g2) includes an aliphatic hydrocarbon group having a halogen atom, specifically an alkyl group having a halogen atom, an alicyclic hydrocarbon group (preferably a cycloalkyl group having a halogen atom). Examples of the halogen atom include fluorine atom, chlorine atom, bromine atom or iodine atom, and preferably include fluorine atom.

In case that $R^{a42}$ represents an aliphatic hydrocarbon group having a halogen group and $A^{a41}$ represents ethylene group, specific examples of the structural unit represented by formula (a4-1) include those represented by formulae (a4-1-1) to (a4-1-22).

(a4-1-1)
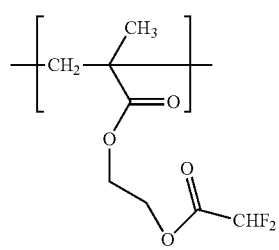

(a4-1-2)
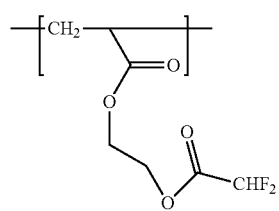

(a4-1-3)
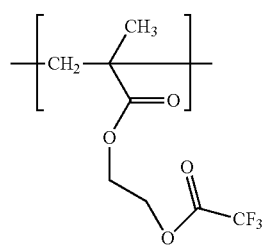

(a4-1-4)
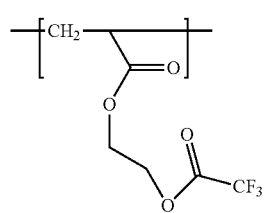

(a4-1-5)
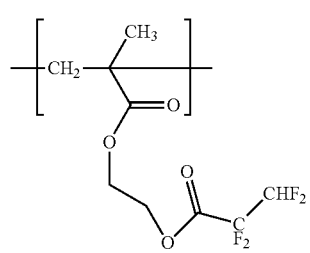

(a4-1-6)
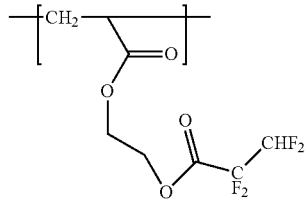

(a4-1-7)
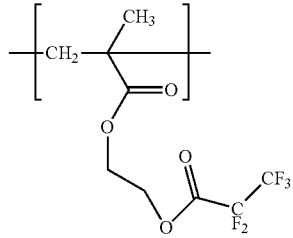

(a4-1-8)
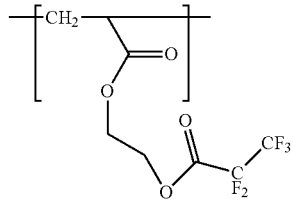

(a4-1-9)
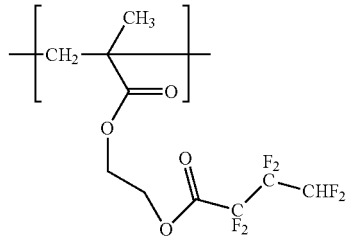

(a4-1-10)
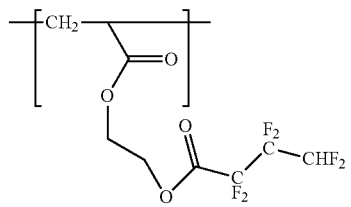

(a4-1-11)
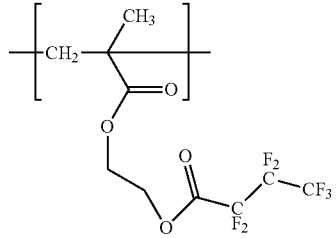

(a4-1-12)
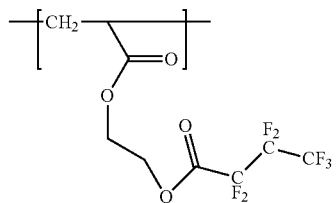

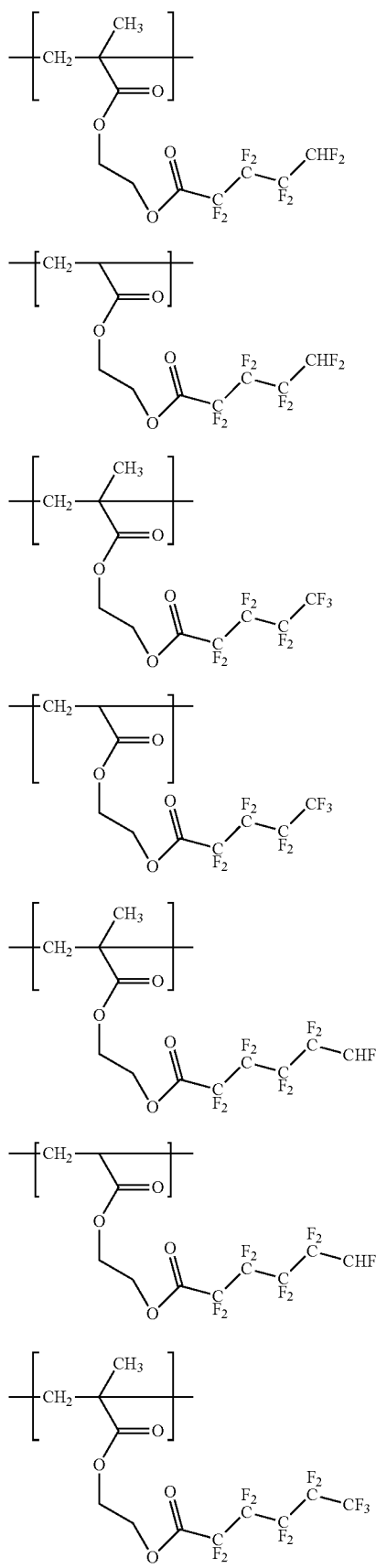

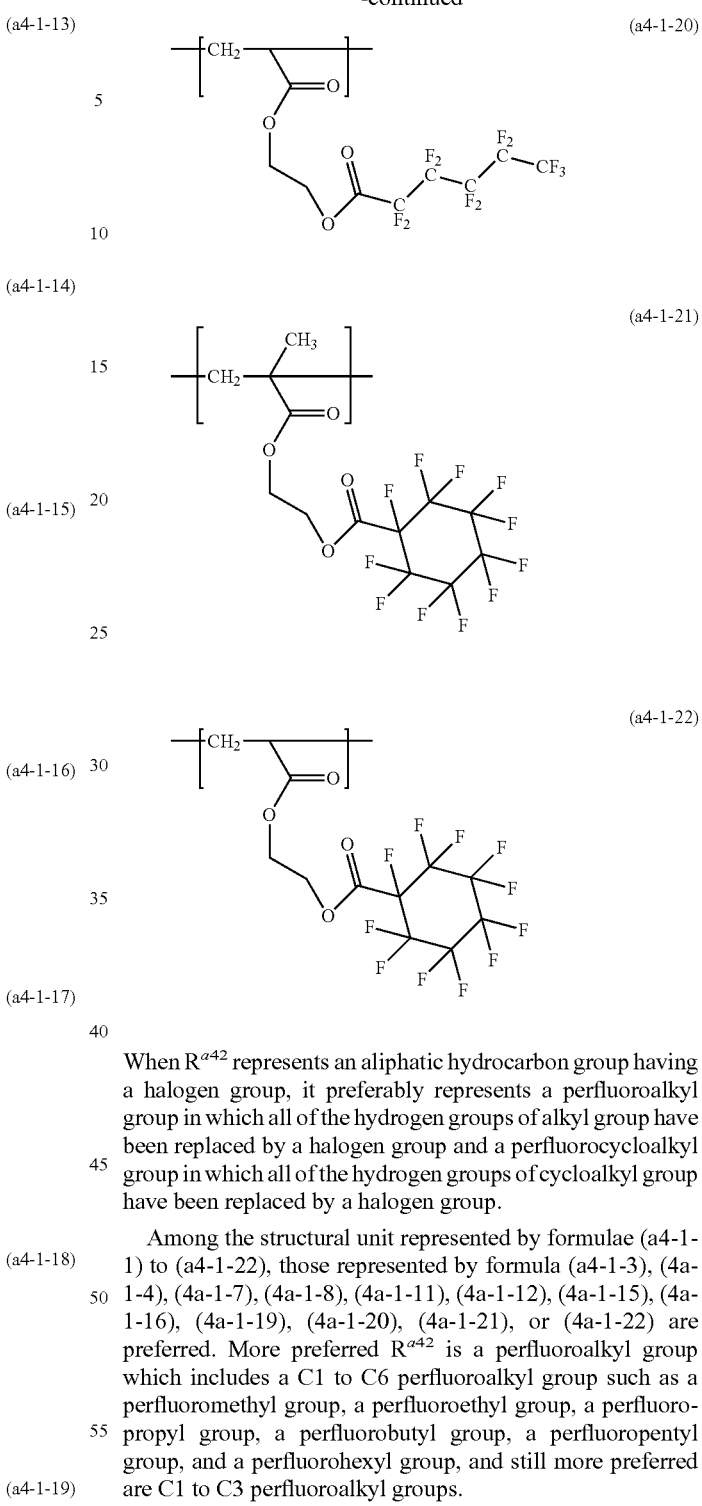

When $R^{a42}$ represents an aliphatic hydrocarbon group having a halogen group, it preferably represents a perfluoroalkyl group in which all of the hydrogen groups of alkyl group have been replaced by a halogen group and a perfluorocycloalkyl group in which all of the hydrogen groups of cycloalkyl group have been replaced by a halogen group.

Among the structural unit represented by formulae (a4-1-1) to (a4-1-22), those represented by formula (a4-1-3), (4a-1-4), (4a-1-7), (4a-1-8), (4a-1-11), (4a-1-12), (4a-1-15), (4a-1-16), (4a-1-19), (4a-1-20), (4a-1-21), or (4a-1-22) are preferred. More preferred $R^{a42}$ is a perfluoroalkyl group which includes a C1 to C6 perfluoroalkyl group such as a perfluoromethyl group, a perfluoroethyl group, a perfluoropropyl group, a perfluorobutyl group, a perfluoropentyl group, and a perfluorohexyl group, and still more preferred are C1 to C3 perfluoroalkyl groups.

$R^{a42}$ may have two or more aliphatic hydrocarbon groups having a group represented by formula (a-g3), which aliphatic hydrocarbon group has preferably 15 or less carbon atoms in total, more preferably 12 or less carbon atoms in total. $R^{a42}$ preferably has one aliphatic hydrocarbon groups having a group represented by formula (a-g3). In case that the structural unit represented by formula (a4-1) is an aliphatic hydrocarbon group which has a group represented by formula (a-g2), the structural unit is represented by formula (a4-1');

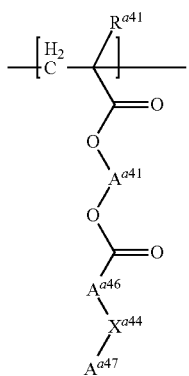 (a4-1′)

in which $R^{a41}$, $A^{a41}$, $A^{a46}$, $X^{a44}$ and $A^{a47}$ are defined as above.

As to formula (a4-1′), both $A^{a46}$ and $A^{a47}$ can have a halogen atom. However, preferably one of $A^{a46}$ and $A^{a47}$ represents an aliphatic hydrocarbon group having a halogen atom, more preferably $A^{a46}$ represents an aliphatic hydrocarbon group having a halogen atom, still more preferably $A^{a46}$ represents an alkanediyl group having a halogen atom, and in particular preferably $A^{a46}$ represents an perfluoroalkanediyl group.

In case that $A^{a46}$ represents a perfluoroalkanediyl group having a halogen group and $A^{a41}$ represents an ethylene group, specific examples of the structural unit represented by formula (a4-1′) include structural units represented by formulae (a4-1′-1) to (a4-1′-22).

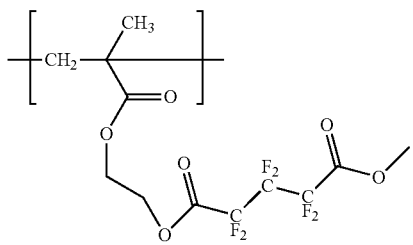 (a4-1′-1)

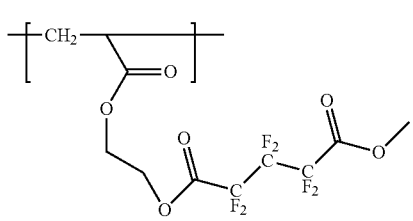 (a4-1′-2)

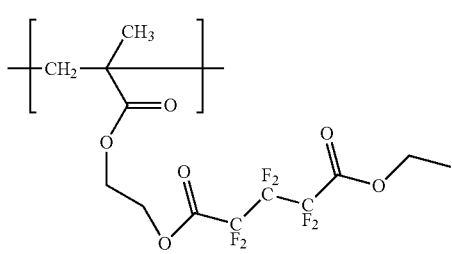 (a4-1′-3)

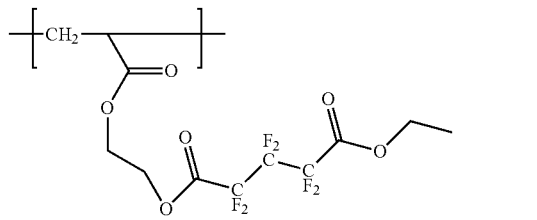 (a4-1′-4)

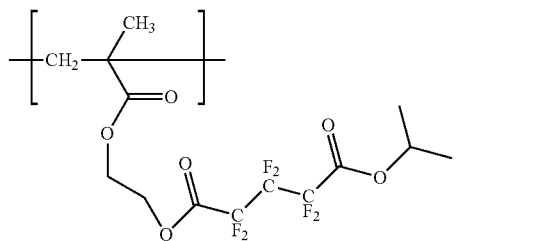 (a4-1′-5)

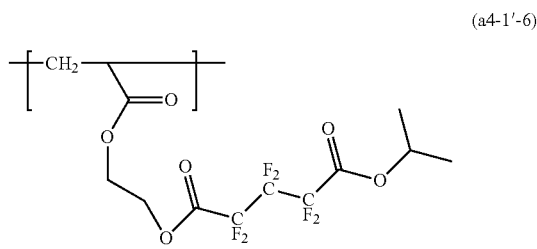 (a4-1′-6)

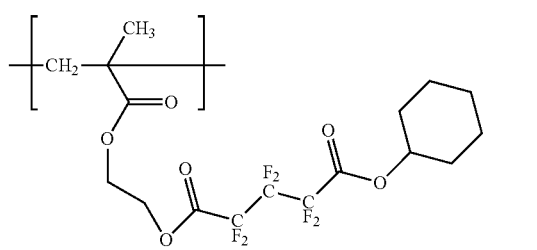 (a4-1′-7)

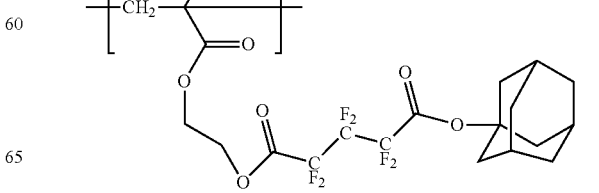 (a4-1′-8)

(a4-1′-9)

(a4-1'-10)
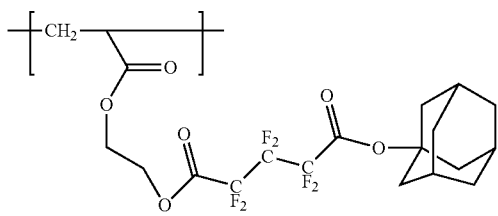
(a4-1'-11)
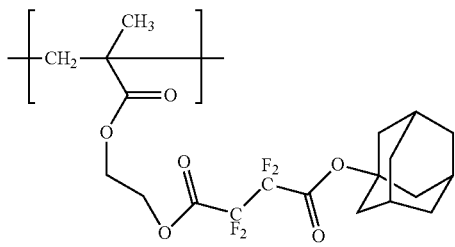
(a4-1'-12)
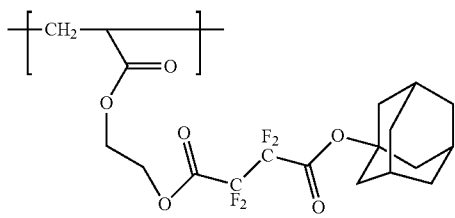
(a4-1'-13)
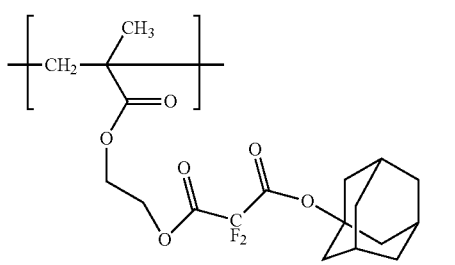
(a4-1'-14)
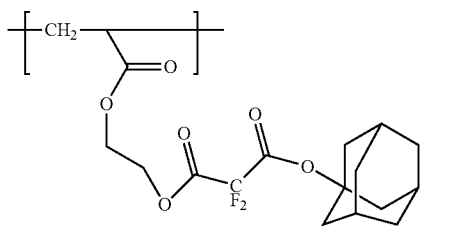
(a4-1'-15)
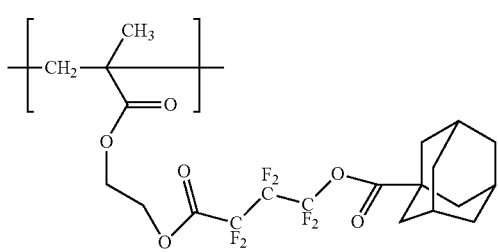
(a4-1'-16)
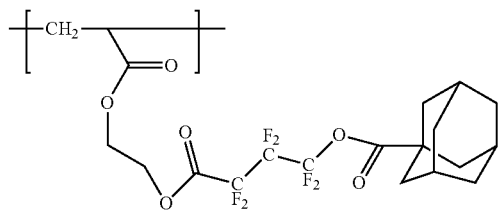
(a4-1'-17)
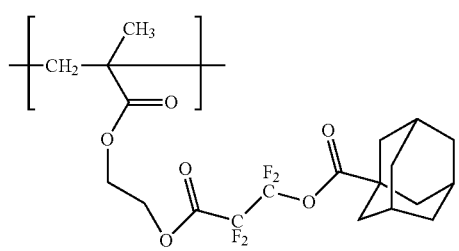
(a4-1'-18)
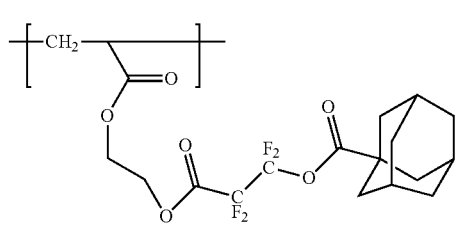
(a4-1'-19)
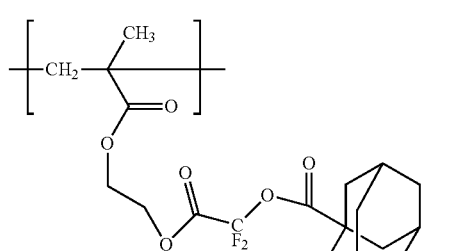
(a4-1'-20)
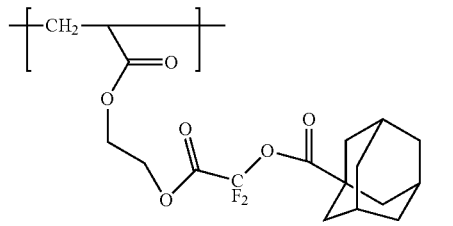
(a4-1'-21)
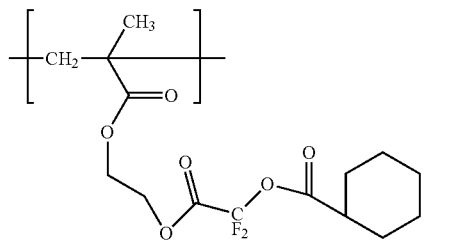

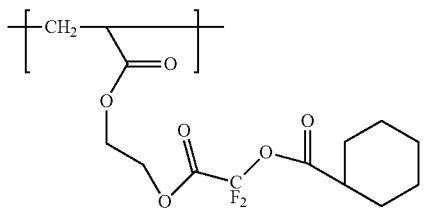

(a4-1'-22)

The total number of carbon atoms of $A^{a46}$ and $A^{a47}$ is 17 or less. The number of carbon atoms of $A^{a46}$ is preferably 1 to 6, and more preferably 1 to 3.

The total number of carbon atoms of $A^{a47}$ is preferably 4 to 15, more preferably 5 to 12.

$A^{a47}$ is preferably a C6 to C12 alicyclic hydrocarbon group, more preferably cyclohexyl group and adamantly group.

As *-$A^{a46}$-$X^{a44}$-$A^{a47}$, preferred moieties include ones as follow:

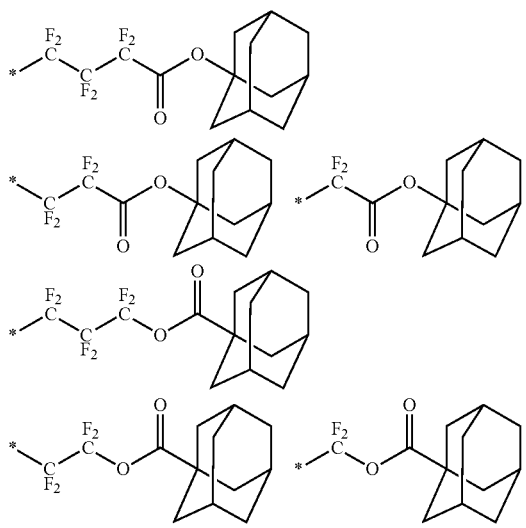

The structural unit having one of these preferred moieties corresponds to the structural units represented by formulae (a4-1'-9) to (a4-1'-20).

When the resin contains a structural unit represented by the formula (a4-1), formula (a1) and formula (a2) or (a3), the content of the structural unit represented by formula (a4-1) is usually 1 to 20% by mole and preferably 2 to 15% by mole, and more preferably 3 to 10% by mole based on the total molar of all the structural units of the resin.

The photoresist composition of the present invention further comprises another resin differing from the resin (A) and having a structural unit represented by formula (a4-1). Hereinafter, such resin is sometimes referred to as "resin (X)".

In resin (X), the content of the structural unit represented by formula (a4-1) is preferably not less than 80% by mole, more preferably not less than 83% by mole, still more preferably not less than 90% by mole, based on the total structural unit of the resin. The resin (X) may consist of the structural unit represented by formula (a4-1). The resin (X) may have the lactone ring-containing structural unit and the structural unit having a hydroxy group. The resin (X) preferably has the structural unit represented by formula (a4-1').

The resin (A) and resin (X) may have another known structural unit in the art, unless these resins detract from these properties.

The resin (A) can be obtained usually by copolymerizing a compound from which the lactone ring-containing structural unit is derived and a compound from which the acid labile group-containing structural unit is derived, preferably by copolymerizing a compound from which the structural unit represented by formula (1) and/or formula (2) is derived and a compound from which the lactone ring-containing structural unit is derived, more preferably by copolymerizing a compound from which the structural unit represented by formula (1) and/or formula (2) is derived, a compound from which the lactone ring-containing structural unit is derived, and a compound from which the structural unit having a hydroxy group is derived, still more preferably by copolymerizing a compound from which the lactone ring-containing structural unit is derived, a compound from which the structural unit represented by formula (a1-1) and/or formula (a2-1) is derived and a compound from which the structural unit having a hydroxy group is derived, particularly preferably by copolymerizing a compound from which the lactone ring-containing structural unit is derived, a compound from which the structural unit represented by formula (a2-1) is derived, and a compound from which the structural unit having a hydroxy group is derived. As the acid labile group-containing structural unit for the resin (A), preferred are an amadantane ring-containing structural unit, and more preferred are the structural unit represented by (a1-1)

The resin (X) can be obtained usually by polymerizing a compound from which the structural unit represented by formula (a4-1), preferably formula (a4-1') is derived.

The resin (A) and resin (X) can be produced according to known polymerization methods such as radical polymerization.

The resin (A) usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight.

The resin (X) usually has 8,000 or more of the weight-average molecular weight, preferably 10,000 or more of the weight-average molecular weight. The resin usually has 80,000 or less of the weight-average molecular weight, preferably has 60,000 or less of the weight-average molecular weight.

The weight-average molecular weight can be measured with gel permeation chromatography (standard: polyethylene).

The photoresist composition of the present invention comprises a salt represented by the formula (I). Hereinafter, such salt is sometimes referred to as "SALT (I)".

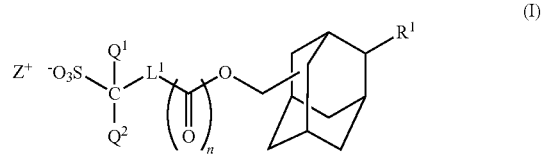

(I)

wherein $Q^1$ and $Q^2$ each independently represent a fluorine atom or a C1-C6 perfluoroalkyl group,
n represents 0 or 1, L¹ represents a single bond or a C1-C10 alkanediyl group in which a methylene group may be replaced by an oxygen atom or a carbonyl group, provided that L¹ is not a single bond when n is 0, R¹ represents a hydroxy group or a hydroxy group protected by a protecting group, and Z⁺ represents an organic cation.

Hereinafter, the moiety corresponding to the part except Z⁺ in formula (I) and having a negative charge is sometimes referred to as "sulfonic acid anion".

Examples of the C1-C6 perfluoroalkyl group represented by $Q^1$ and $Q^2$ include a trifluoromethyl group, a pentafluoroethyl group, a heptafluoropropyl group, a nonafluorobutyl group, an undecafluoropentyl group and a tridecafluorohexyl group. It is preferred that $Q^1$ and $Q^2$ independently each represent a fluorine atom or a C1-C3 perfluoroalkyl group, it is more preferred that $Q^1$ and $Q^2$ independently each represent a fluorine atom or a trifluoromethyl group, and it is still more preferred that $Q^1$ and $Q^2$ are fluorine atoms.

L¹ represents a single bond or a C1-C10 divalent saturated hydrocarbon group in which a methylene group may be replaced by an oxygen atom or a carbonyl group. When n is 0, L¹ is not a single bond. Such divalent saturated hydrocarbon group includes a linear chain alkanediyl group, a branched chain alkanediyl group, a monocyclic or dicyclic divalent alicyclic hydrocarbon group, and a group in which two or more of these alkanediyl and alicyclic hydrocarbon groups have been combined.

Examples of L¹ include linear hydrocarbon groups such as a methylene group, an ethylene group, a propane-1,3-diyl group, a propane-1,2-diyl group, a butane-1,4-diyl group, a butane-1,3-diyl group, a pentano-1,5-diyl group, a hexane-1,6-diyl group, a heptane-1,7-diyl group, an octane-1,8-diyl group, a nonane-1,9-diyl group, a decane-1,10-diyl group, an ethane-1,1-diyl group, a propane-1,1-diyl group;

branched chain groups including a group formed by attaching a side chain to a linear hydrocarbon group, such as a butan-1,3-diyl group, a2-methylpropane-1,3-diyl group, a 2-methylpropane-1,2-diyl group, a pentane-1,4-diyl group, and a 2-methylbutane-1,4-diyl group;

a monocyclic divalent alicyclic hydrocarbon groups such as a cyclobutan-1,3-diyl group, cyclopentane-1,3-diyl group, a cyclohexane-1,2-diyl group, a 1-methylcyclohexane-1,2-diyl group, cyclohexane-1,4-diyl group, cyclooctane-1,2-diyl group, and a cyclooctane-1,5-diyl group; and a polycyclic divalent alicyclic hydrocarbon groups such as a norbornane-2,3-diyl group, norbornane-1,4-diyl group, a norbornane-2,5-diyl group, an amadantane-1,2-diyl group, an amadantane-1,5-diyl group and an amadantane-1,6-diyl group.

When L¹ represents a C1-C10 alkanediyl group in which a methylene group has been replaced by an oxygen atom or a carbonyl group, examples of L¹ include the moiety represented by any one of formulae (b1-1) to (b1-6) as follow.

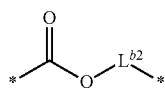

(b1-1)

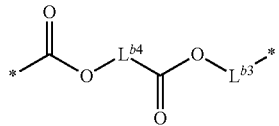

(b1-2)

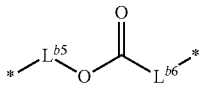

(b1-3)

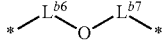

(b1-4)

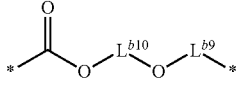

(b1-5)

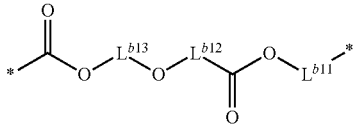

(b1-6)

wherein $L^{b2}$ represents a C1-C8 alkanediyl group,
$L^{b3}$ represents a C1-C5 alkanediyl group,
$L^{b4}$ represents a C1-C5 alkanediyl group provided that the total carbon atoms of $L^{b3}$ and $L^{b4}$ is up to 6,
$L^{b5}$ represents a C1-C7 alkanediyl group,
$L^{b6}$ represents a C1-C7 alkanediyl group provided that the total carbon atoms of $L^{b5}$ and $L^{b6}$ is up to 8,
$L^{b7}$ represents a C1-C8 alkanediyl group,
$L^{b8}$ represents C1-C8 alkanediyl group with the proviso that total carbon number of $L^{b7}$ and $L^{b8}$ is up to 9,
$L^{b9}$ represents a C1-C6 alkanediyl group,
$L^{b10}$ represents a C1-C6 alkanediyl group, with the proviso that total carbon number of $L^{b9}$ and $L^{b10}$ is up to 7,
$L^{b11}$ represents a C1-C3 alkanediyl group,
$L^{b12}$ represents C1-C3 alkanediyl group, and $L^{b13}$ represents C1-C3 alkanediyl group with the proviso that total carbon number of $L^{b11}$, $L^{b12}$ and $L^{b13}$ is up to 5,
* represents a binding position, * of the left side represents a binding position to —C(Q¹)(Q²)-, and * of the right side represents a binding position to —(C=O)—.

Examples of the moiety represented by formula (b1-1) include one represented as follows.

Examples of the moiety represented by formula (b1-2) include one represented as follows.

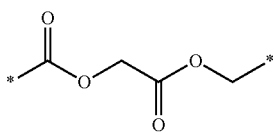

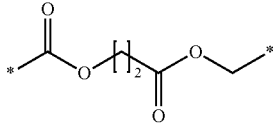

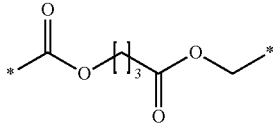

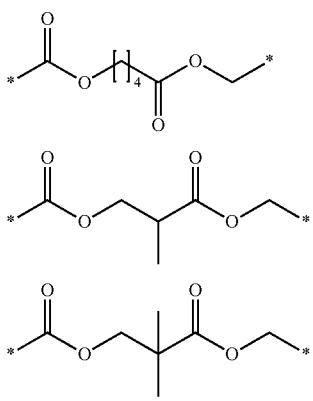

Examples of the moiety represented by formula (b1-3) include one represented as follows.

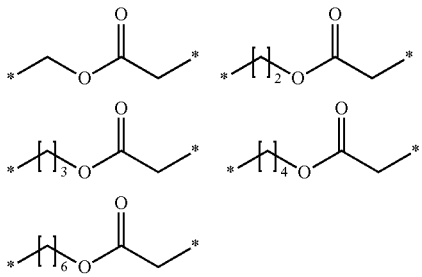

Examples of the moiety represented by formula (b1-4) include one represented as follows.

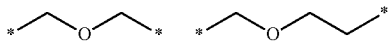

Examples of the moiety represented by formula (b1-5) include one represented as follows.

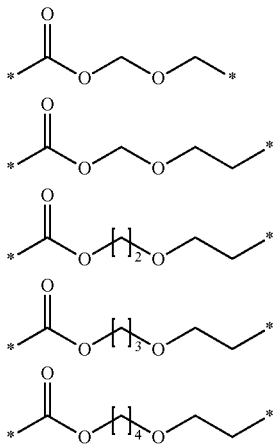

Examples of the moiety represented by formula (b1-6) include one represented as follows.

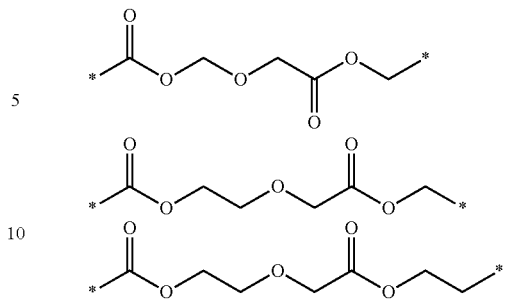

$L^1$ is preferably the moieties represented by any one of formulae (b1-1) to (b1-4), more preferably the moieties represented by any formula (b1-1) or (b1-2), still more preferably the moieties represented by formula (b1-1). Among the moieties represented by formula (b1-1), preferred are those in which $L^{b2}$ represents a single bond or a methylene group, and more preferred are one in which $L^{b2}$ represents a single bond, i.e., *—CO—O— where * represents a binding position to —C($Q^1$)($Q^2$)-.

$R^1$ represents a hydroxy group or a hydroxy group protected by a protecting group. As the protecting group, any group which is known as a group protecting a hydroxy group in the art of organic synthesis may be used.

It is assumed that the protecting group of $R^1$ is converted to a hydroxy group by the action of acids when acids are generated from the SALT (I).

The protecting group includes preferably the groups of formula (1A) and the groups of formula (2A).

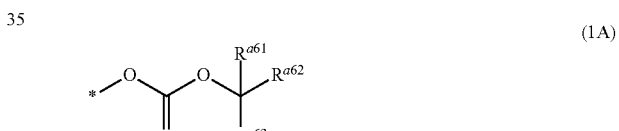

wherein $R^{a61}$, $R^{a62}$ and $R^{a63}$ independently represent C1 to C6 alkyl group, and * represents a binding position,

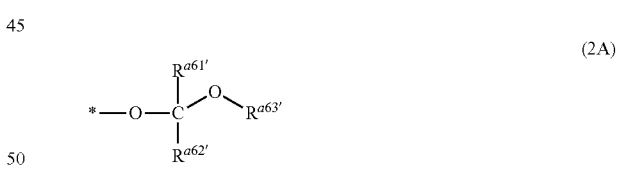

wherein $R^{a61'}$ and $R^{a62'}$ independently represent a hydrogen atom or C1 to C12 monovalent hydrocarbon group in which a methylene group may be replaced by an oxygen atom or a sulfur atom, and $R^{a63'}$ represents a hydrogen atom or C1 to C20 monovalent hydrocarbon group in which a methylene group may be replaced by an oxygen atom or a sulfur atom, or $R^{a63'}$ together with $R^{a62'}$ represents C2 to C20 divalent hydrocarbon group to form a ring including the moiety —C—O—, in which divalent hydrocarbon group a methylene group may be replaced by an oxygen atom or a sulfur atom, and * represents a binding position.

Examples of the C1-C6 alkyl group include a methyl group, an ethyl group, a propyl group, an isopropyl group, a butyl group, an isobutyl group, a sec-butyl group, a tart-butyl group, a pentyl group and a hexyl group.

Examples of the C1-C12 hydrocarbon group include a linear alkyl group, a branched chain alkyl group, and a monocyclic or polycyclic alicyclic hydrocarbon group, or aromatic hydrocarbon group, and specific examples thereof include a methyl group, an ethyl group, an isopropyl group, a cyclohexyl group, a cyclohexylethyl group, a benzyl group and a phenyl group.

$R^{a61}$, $R^{a62}$ and $R^{a63}$ are preferably C1-C3 alkyl group, more preferably a methyl group.

$R^{a61'}$ and $R^{a62'}$ are preferably a hydrogen atom and C1-C4 alkyl group, more preferably a hydrogen atom and methyl group. One or both of $R^{a61'}$ and $R^{a62'}$ are preferably a hydrogen atom. $R^{a63'}$ is preferably C1-C6 alkyl group, more preferably C1-C4 alkyl group.

As preferred protected groups, specific groups of formula (2A) include those represented by formula (2):

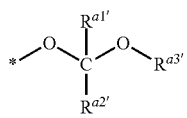
(2)

wherein $R^{a1'}$ and $R^{a2'}$ independently each represent hydrogen atom or a C1-C12 hydrocarbon group, and $R^{a3'}$ represents a C1-C20 monovalent hydrocarbon group, or $R^{a3'}$ together with $R^{a1'}$ and $R^{a2'}$ represents a C2-C20 divalent hydrocarbon group in which a methylene group of the divalent hydrocarbon group may be replaced by —O— or —S—. The groups represented by formula (2) are described as an acid labile group of the structural units of the resin (A).

The protecting group is more preferably the groups of formula (2A), still more preferably the groups of formula (2A) in which $R^{a1'}$ and $R^{a2'}$ respectively represent a hydrogen atom or a C1-C4 alkyl group and $R^{a3'}$ represents a C1-C4 alkyl group.

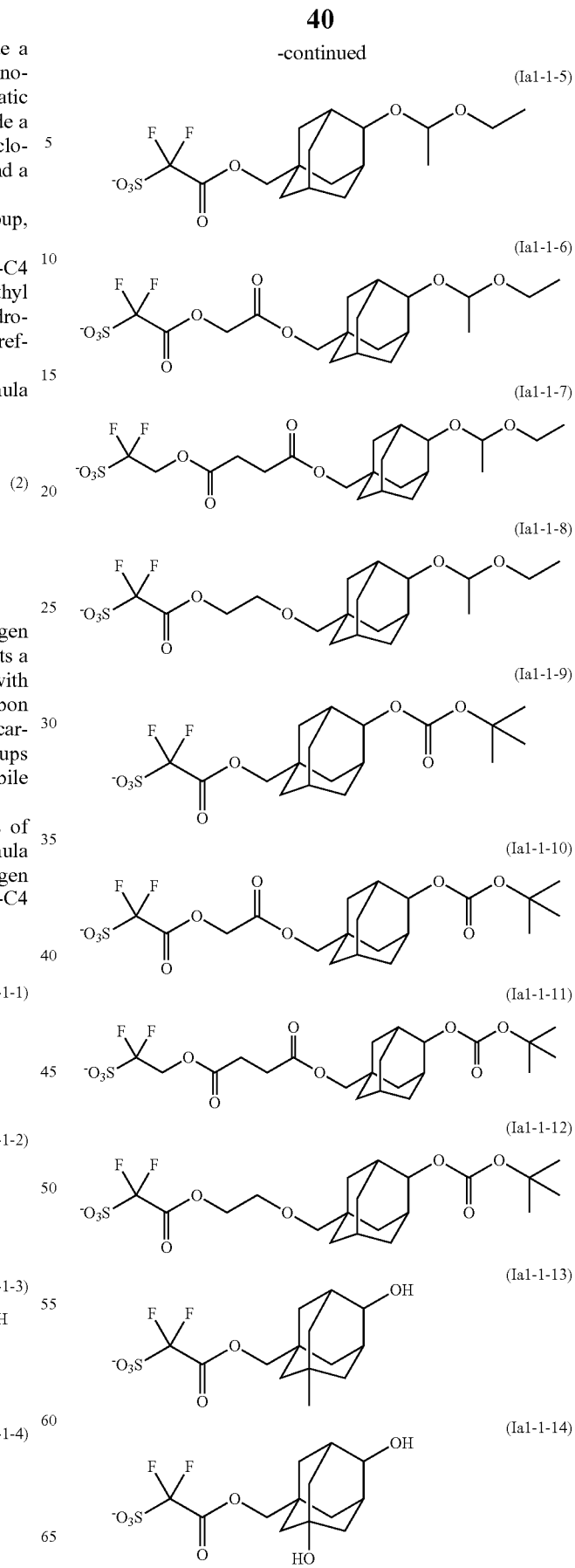

-continued

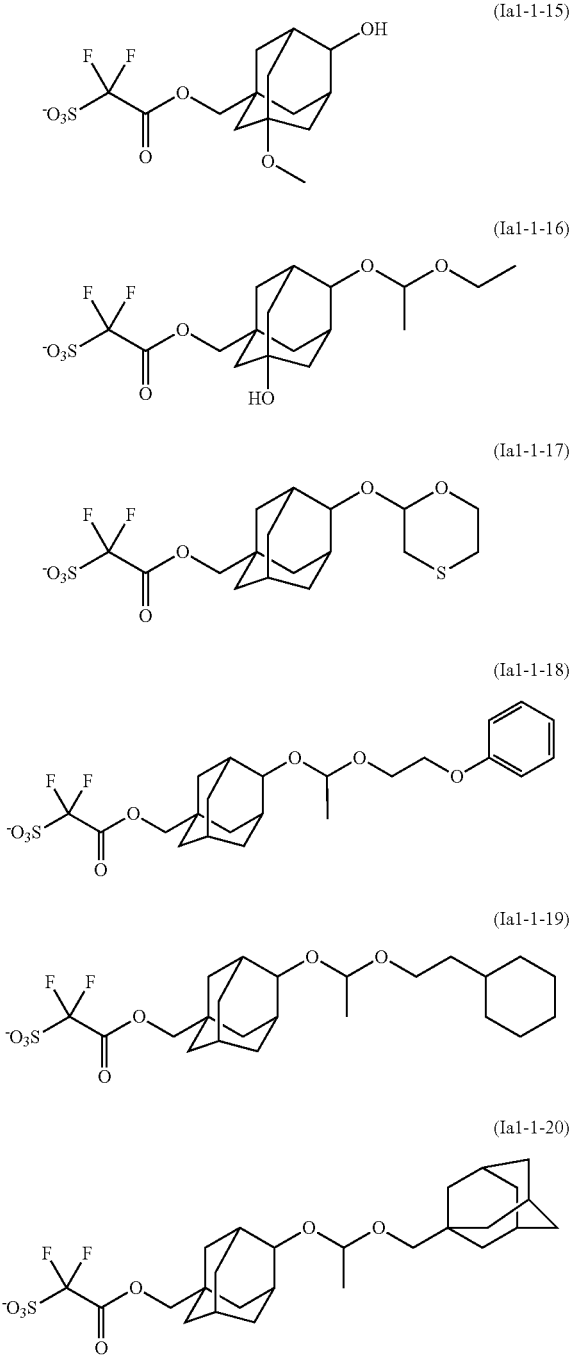

(Ia1-1-15)
(Ia1-1-16)
(Ia1-1-17)
(Ia1-1-18)
(Ia1-1-19)
(Ia1-1-20)

Hereinafter, the organic anion of SALT (I) will be described. Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. Herein, the arylsulfonium includes those having one, two or three aryl groups.

Preferable examples of the organic cation represented by $Z^+$ include the organic cations represented by the formulae (b2-1) to (b2-4):

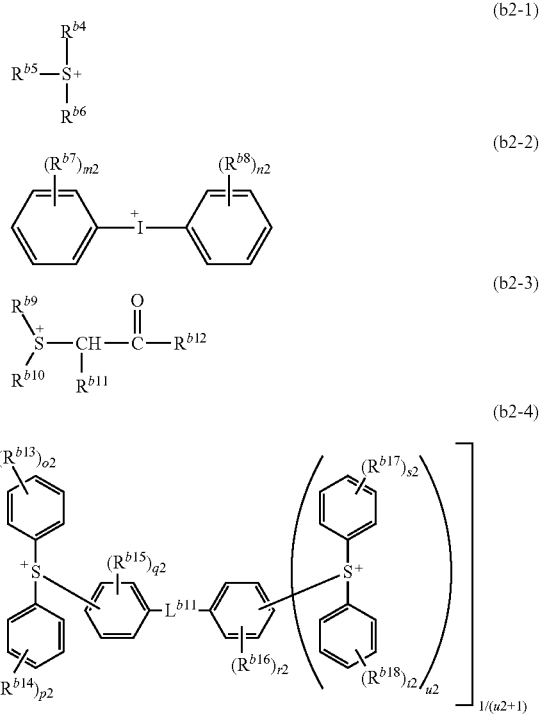

(b2-1)
(b2-2)
(b2-3)
(b2-4)

wherein $R^{b4}$, $R^{b5}$ and $R^{b6}$ independently represent a C1-C18 alkyl group in which a hydrogen atom can be replaced by a hydroxy group, or a C1-C12 alkoxy group, a C6-C18 aromatic hydrocarbon group, a C3-C18 alicyclic hydrocarbon group in which a hydrogen atom can be replaced by a halogen atom, a C2-C4 acyl group or a glycidyloxy group, and a C6-C18 aromatic hydrocarbon group in which a hydrogen atom can be replaced by a halogen atom, a hydroxy group, C1-C18 alicyclic hydrocarbon group, or C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxy group, a C1-C12 alkyl group or a C1-C12 alkoxy group, m2 and n2 independently represents an integer of 0 to 5, $R^{b9}$ and $R^{b10}$ independently represent a C1-C18 alkyl group or a C3-C18 alicyclic hydrocarbon group, or $R^{b9}$ and $R^{b10}$ are bonded each other to form a C1-C10 divalent acyclic hydrocarbon group which forms a 3- to 12-membered ring, preferably 3- to 7-membered ring together with the adjacent —$S^+$—, and one or more —$CH_2$— in the divalent acyclic hydrocarbon group may be replaced by an oxygen atom, sulfur atom or carbonyl group, and $R^{b11}$ represents a hydrogen atom, a C1-C18 alkyl group, or a C3-C18 alicyclic hydrocarbon group, or a C6-C18 aromatic hydrocarbon group. and $R^{b12}$ represents a C1-C12 alkyl group, a C3-C18 alicyclic hydrocarbon group, a C6-C18 aromatic hydrocarbon group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by an oxygen atom, sulfur atom or carbonyl atom, and $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the alicyclic hydrocarbon group represented by $R^{b4}$ to $R^{b6}$ include a cyclopropyl group, a cyclobutyl group, a cyclopentyl group, a cyclohexyl group, a cycloheptyl group, a cyclodecyl group, an adamantyl group, a 2-alkyladamantyl-2-yl group, a 1-(adaman-2-yl)alkane-1-yl group and an isobornyl group, and more preferable examples thereof include a cyclopentyl group and a cyclohexyl group. Preferable examples of the aromatic group represented by $R^{b4}$ to $R^{b6}$ include a phenyl group, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms. Preferable examples of the alkyl group represented by $R^{b7}$ and $R^{b8}$ include a methyl group, an ethyl group, a propyl group, an isopropyl group, a butyl group, a sec-butyl group, a tert-butyl group, a pentyl group, a hexyl group, an octyl group and a 2-ethylhexyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Preferable examples of the alkyl group represented by $R^{b9}$ to $R^{b12}$ include a methyl group, an ethyl group, a propyl group, an isopropyl group, a butyl group, a sec-butyl group, a tert-butyl group, a pentyl group, a hexyl group, an octyl group and a 2-ethylhexyl group. Such alkyl group preferably has 1 to 12 carbon atoms. Preferable examples of the alicyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group.

The alicyclic hydrocarbon group represented by $R^{b9}$ to $R^{b11}$ has preferably 4 to 12 carbon atoms.

Preferable examples of the aromatic group represented by $R^{b12}$ include a phenyl group, 4-methyl phenyl group, 4-ethyl phenyl group, 4-tert butyl phenyl group, 4-cyclohexyl phenyl group, 4-methoxy phenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group.

Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclohexane ring, oxonorbornane ring and oxoamadantane ring. A C1-C5 divalent acyclic hydrocarbon group is preferable.

Examples of the group in which the alkyl group has been combined with the aromatic hydrocarbon group include typically an aralkyl group, preferably benzyl group. As examples of the organic cations represented by formulae (b2-1) to (b2-4) include organic cations mentioned in JP2010-204646A1.

Among the above-mentioned cations, preferred is the cation represented by the formula (b2-1), more preferred is the cation represented by the formula (b2-1) in which any of $R^{b4}$, $R^{b5}$ and $R^{b6}$ is an aromatic hydrocarbon group, still more preferred is the cation represented by the formula (b2-1-1), especially more preferred is triphenylphosphonium cation or tritolylsulfonium cation.

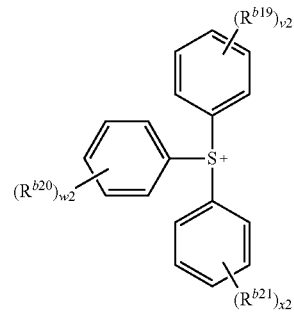

(b2-1-1)

wherein $R^{b19}$, $R^{b20}$ and $R^{b21}$ are independently in each occurrence a halogen atom (preferably a fluorine atom); a hydroxy group; a C1-C18 aliphatic hydrocarbon group in which one or more hydrogen atoms can be replaced by a halogen group, a C2-C4 acyl group, or a grycidyloxy group; or a C1-C12 alkoxy group; and $R^{b19}$ and $R^{b20}$, $R^{b19}$ and $R^{b21}$ or $R^{b20}$ and $R^{b21}$ can be bonded each other to form a ring together with $S^+$, and v2, w2 and x2 independently each represent an integer of 0 to 5. The aliphatic hydrocarbon group of $R^{b19}$, $R^{b20}$ and $R^{b21}$ includes an alkyl group and an aliphatic hydrocarbon group, preferably C1-C12 alkyl group and C1-C18 aliphatic hydrocarbon group.

Each of $R^{b19}$, $R^{b20}$ and $R^{b21}$ is preferably a halogen atom (preferably a fluorine atom), a hydroxy group, a C1-C12 alkyl group and a C1-C12 alkoxy group, and more preferably a halogen atom (preferably a fluorine atom) and a C1-C6 alkyl group.

The v2, w2 and x2 independently each represent 0 or 1.

As the cation represented by the formula (b2-1-1), a triphenylsulfonium cation and a tritolylsulfonium cation are especially preferable.
Examples of the cation represented by the formula (b2-1-1) include the following.
(b2-c-1)
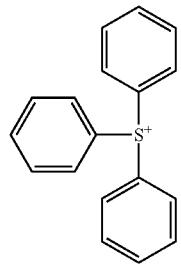
(b2-c-2)
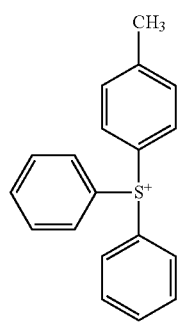
(b2-c-3)
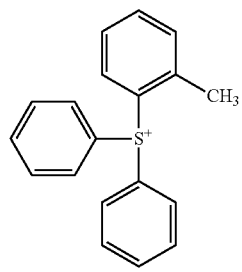
(b2-c-4)
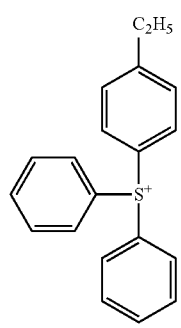
(b2-c-5)
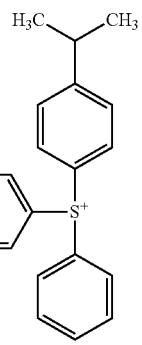
(b2-c-6)
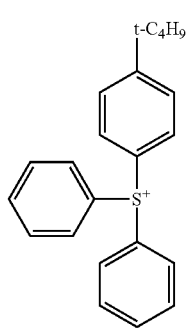
(b2-c-7)
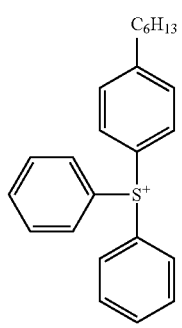
(b2-c-8)
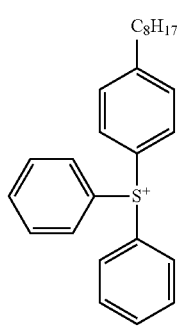
(b2-c-9)
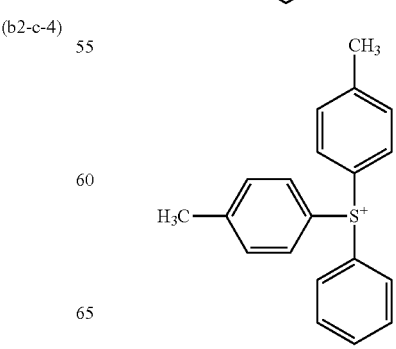

(b2-c-10)
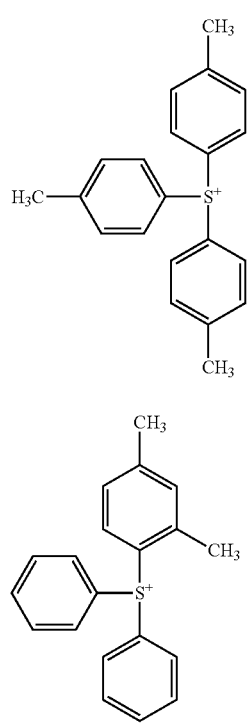
(b2c-11)
(b2-c-12)
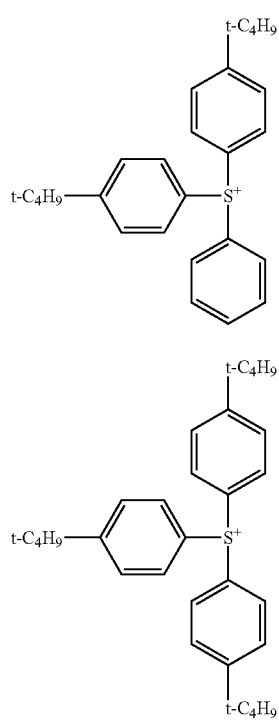
(b2-c-13)
(b2-c-14)
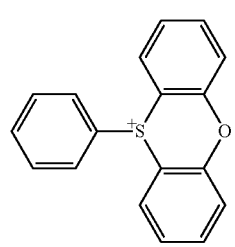
(b2-c-15)
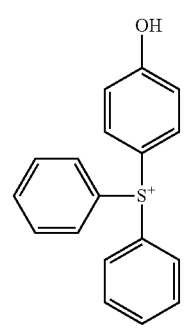
(b2-c-16)
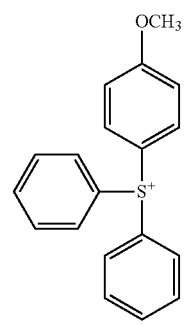
(b2-c-17)
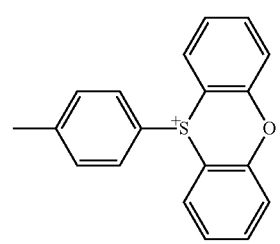
(b2-c-18)
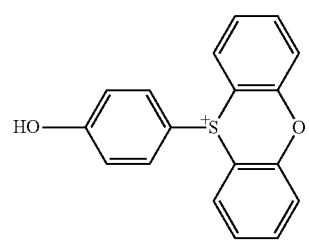
(b2-c-19)
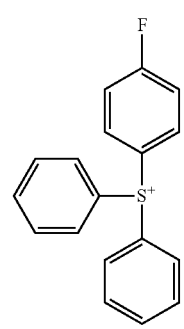

(b2-c-20)
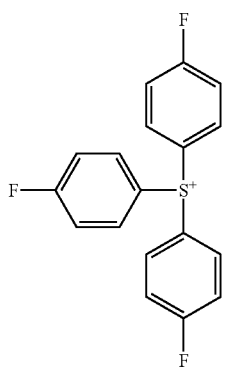
(b2-c-21)
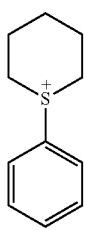
(b2-c-22)
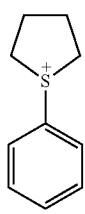
(b2-c-23)
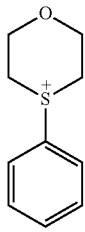
(b2-c-24)
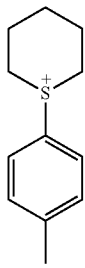
(b2-c-25)
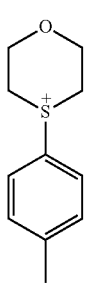
(b2-c-26)
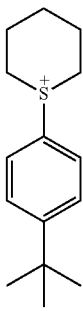
(b2-c-27)
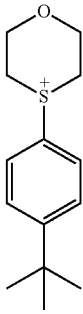
Examples of the cation represented by the formula (b2-2) include the followings.
(b2-c-28)
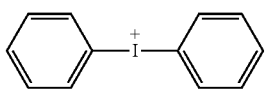
(b2-c-29)
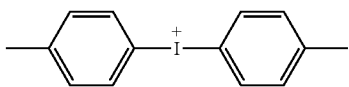
(b2-c-30)
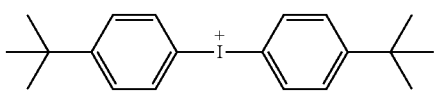
Examples of the cation represented by the formula (b2-3) include the followings.
(b2-c-31)
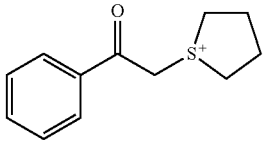
(b2-c-32)
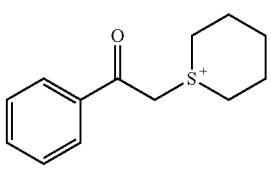

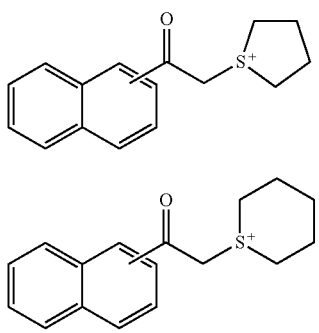 (b2-c-33)
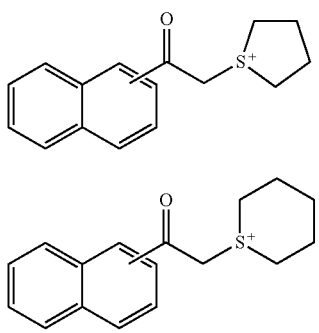 (b2-c-34)
Examples of the cation represented by the formula (b2-4) include the followings.
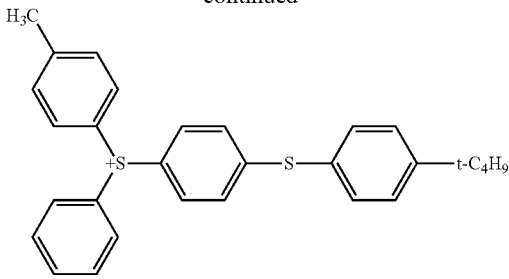
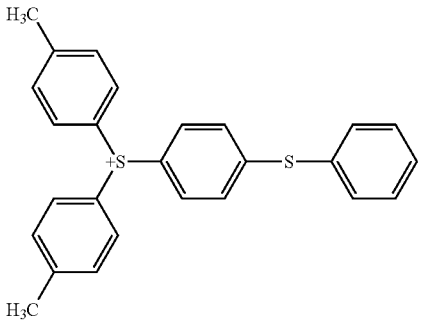
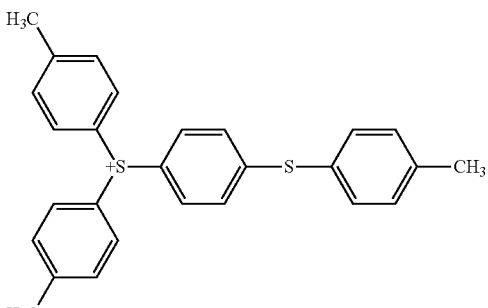
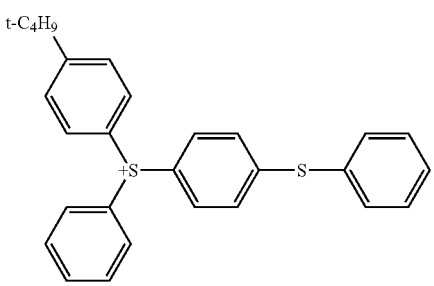
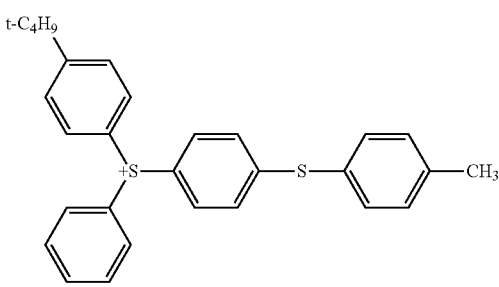

-continued
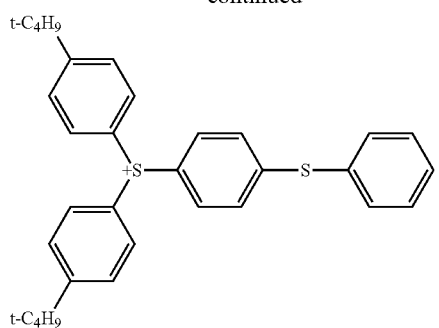
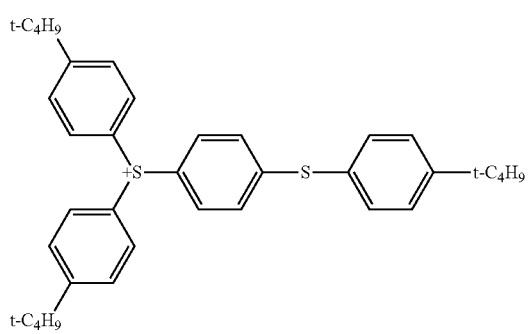
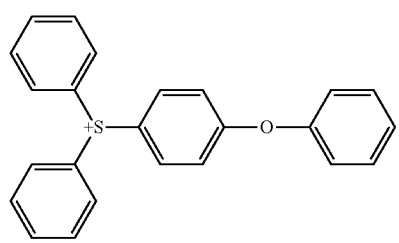
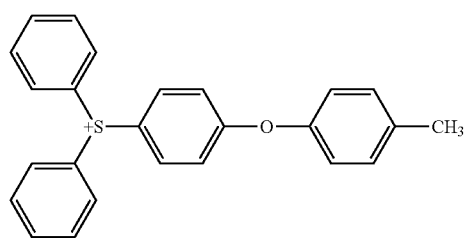
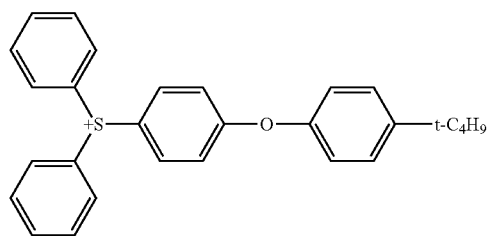
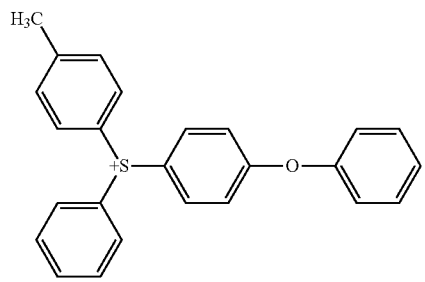
-continued
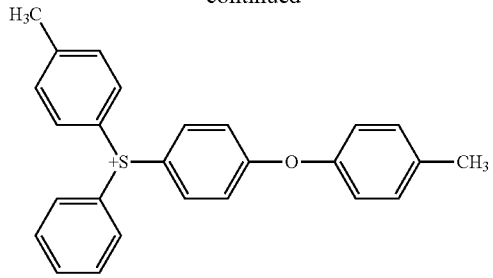
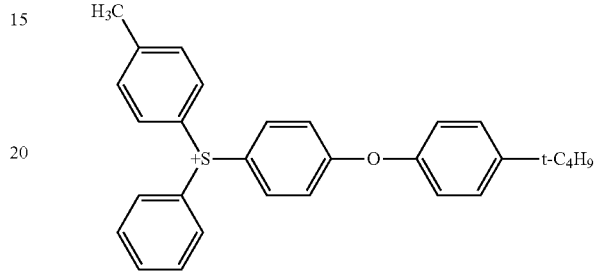
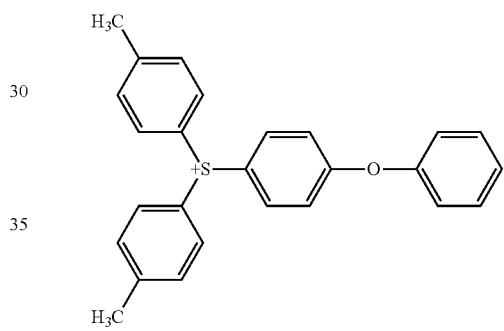
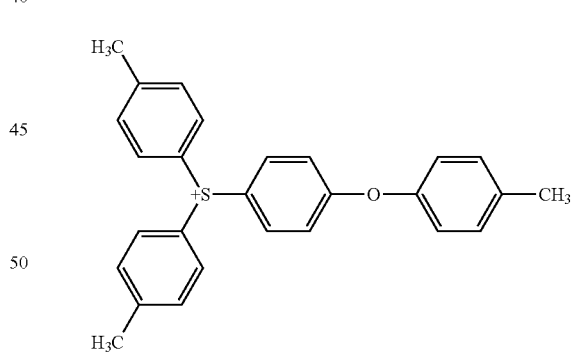
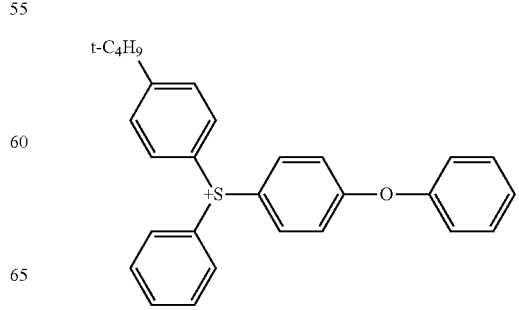

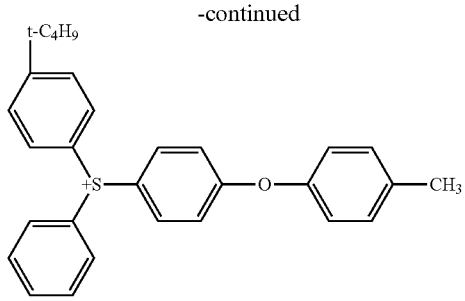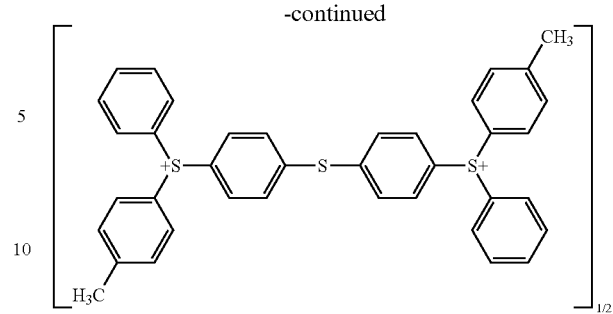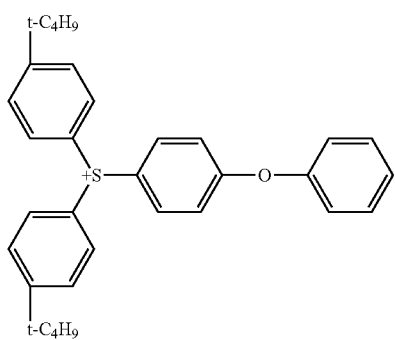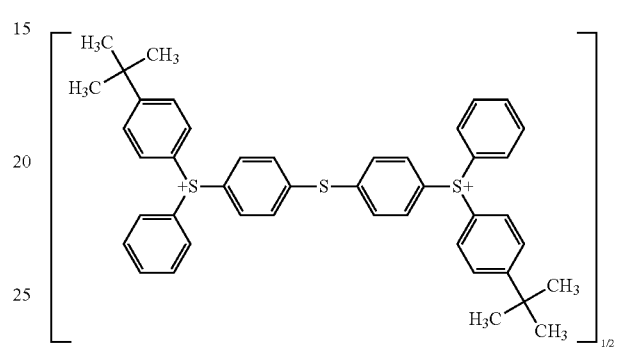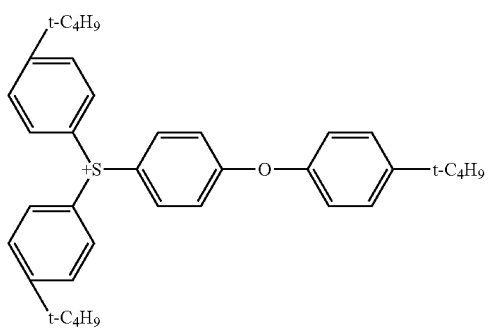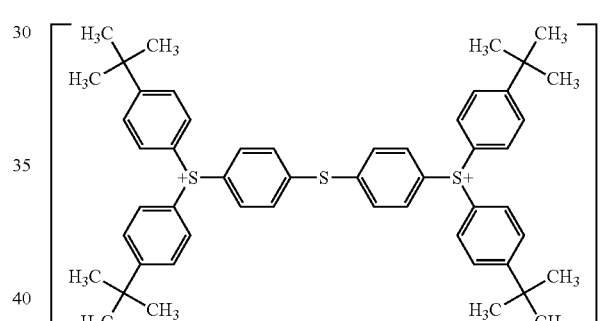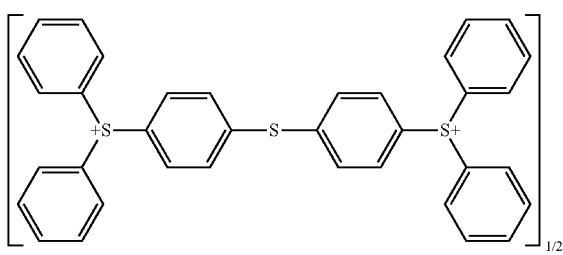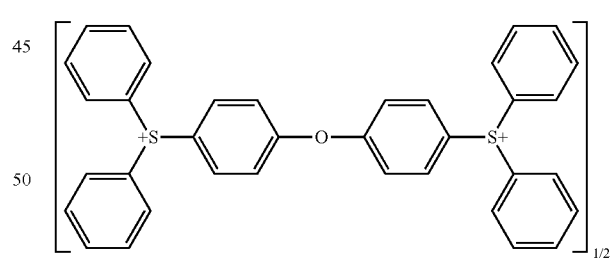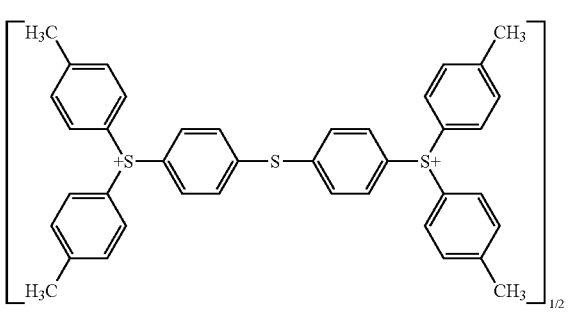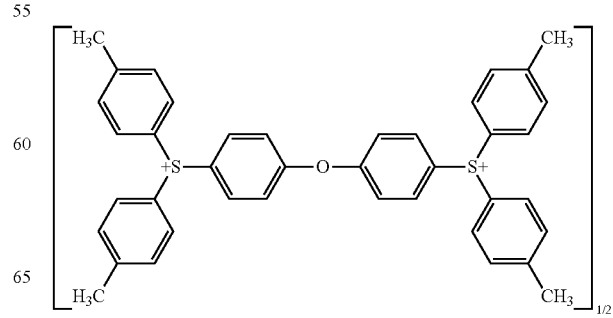

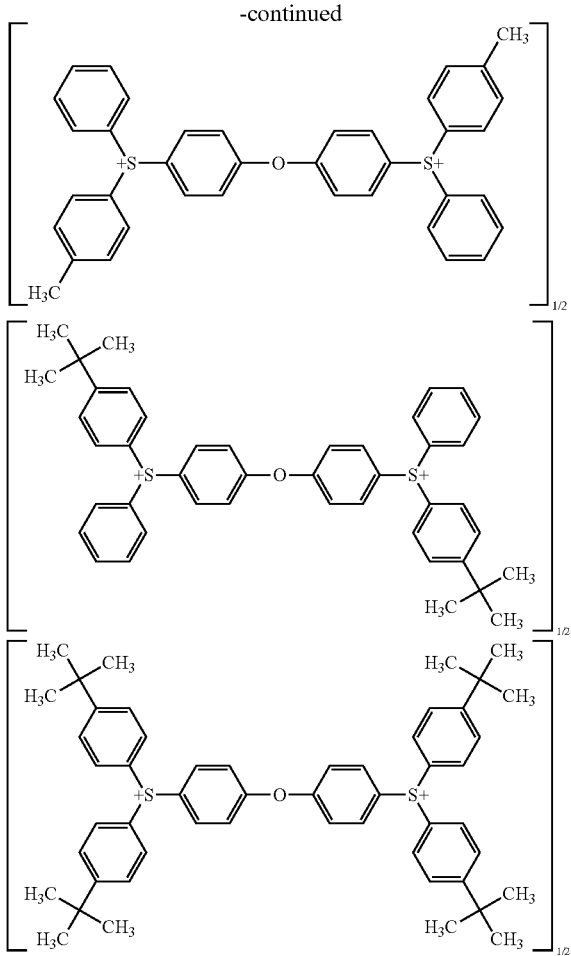

Examples of SALT (I) include a salt wherein the anion is any one of the above-mentioned anions and the counter ion is any one of organic cations. Preferable examples of SALT (I) include those shown in Tables 1, 2, 3 and 4.

In each tables, any symbol of column "sulfonic acid" refers to the symbol of formula representing the sulfonic acid, any symbol of column "organic cation" refers to the symbol of formula representing the counter ion, and any symbol of column "SALT (I)" refers to the symbol of formula representing the SALT (I).

TABLE 1

| SALT (I) | Sulfonic acid | organic cation |
|---|---|---|
| (I-1) | (Ia1-1-1) | (b2-c-1) |
| (I-2) | (Ia1-1-2) | (b2-c-1) |
| (I-3) | (Ia1-1-3) | (b2-c-1) |
| (I-4) | (Ia1-1-4) | (b2-c-1) |
| (I-5) | (Ia1-1-5) | (b2-c-1) |
| (I-6) | (Ia1-1-6) | (b2-c-1) |
| (I-7) | (Ia1-1-7) | (b2-c-1) |
| (I-8) | (Ia1-1-8) | (b2-c-1) |
| (I-9) | (Ia1-1-9) | (b2-c-1) |
| (I-10) | (Ia1-1-10) | (b2-c-1) |
| (I-11) | (Ia1-1-11) | (b2-c-1) |
| (I-12) | (Ia1-1-12) | (b2-c-1) |
| (I-13) | (Ia1-1-1) | (b2-c-10) |
| (I-14) | (Ia1-1-2) | (b2-c-10) |
| (I-15) | (Ia1-1-3) | (b2-c-10) |
| (I-16) | (Ia1-1-4) | (b2-c-10) |
| (I-17) | (Ia1-1-5) | (b2-c-10) |

TABLE 1-continued

| SALT (I) | Sulfonic acid | organic cation |
|---|---|---|
| (I-18) | (Ia1-1-6) | (b2-c-10) |
| (I-19) | (Ia1-1-7) | (b2-c-10) |
| (I-20) | (Ia1-1-8) | (b2-c-10) |
| (I-21) | (Ia1-1-9) | (b2-c-10) |
| (I-22) | (Ia1-1-10) | (b2-c-10) |
| (I-23) | (Ia1-1-11) | (b2-c-10) |
| (I-24) | (Ia1-1-12) | (b2-c-10) |
| (I-25) | (Ia1-1-1) | (b2-c-14) |
| (I-26) | (Ia1-1-2) | (b2-c-14) |
| (I-27) | (Ia1-1-3) | (b2-c-14) |
| (I-28) | (Ia1-1-4) | (b2-c-14) |
| (I-29) | (Ia1-1-5) | (b2-c-14) |
| (I-30) | (Ia1-1-6) | (b2-c-14) |
| (I-31) | (Ia1-1-7) | (b2-c-14) |
| (I-32) | (Ia1-1-8) | (b2-c-14) |
| (I-33) | (Ia1-1-9) | (b2-c-14) |
| (I-34) | (Ia1-1-10) | (b2-c-14) |

TABLE 2

| SALT (I) | Sulfonic acid | organic cation |
|---|---|---|
| (I-35) | (Ia1-1-11) | (b2-c-14) |
| (I-36) | (Ia1-1-12) | (b2-c-14) |
| (I-37) | (Ia1-1-1) | (b2-c-23) |
| (I-38) | (Ia1-1-2) | (b2-c-23) |
| (I-39) | (Ia1-1-3) | (b2-c-23) |
| (I-40) | (Ia1-1-4) | (b2-c-23) |
| (I-41) | (Ia1-1-5) | (b2-c-23) |
| (I-42) | (Ia1-1-6) | (b2-c-23) |
| (I-43) | (Ia1-1-7) | (b2-c-23) |
| (I-44) | (Ia1-1-8) | (b2-c-23) |
| (I-45) | (Ia1-1-9) | (b2-c-23) |
| (I-46) | (Ia1-1-10) | (b2-c-23) |
| (I-47) | (Ia1-1-11) | (b2-c-23) |
| (I-48) | (Ia1-1-12) | (b2-c-23) |
| (I-49) | (Ia1-1-1) | (b2-c-27) |
| (I-50) | (Ia1-1-2) | (b2-c-27) |
| (I-51) | (Ia1-1-3) | (b2-c-27) |
| (I-52) | (Ia1-1-4) | (b2-c-27) |
| (I-53) | (Ia1-1-5) | (b2-c-27) |
| (I-54) | (Ia1-1-6) | (b2-c-27) |
| (I-55) | (Ia1-1-7) | (b2-c-27) |
| (I-56) | (Ia1-1-8) | (b2-c-27) |
| (I-57) | (Ia1-1-9) | (b2-c-27) |
| (I-58) | (Ia1-1-10) | (b2-c-27) |
| (I-59) | (Ia1-1-11) | (b2-c-27) |
| (I-60) | (Ia1-1-12) | (b2-c-27) |
| (I-61) | (Ia1-1-1) | (b2-c-28) |
| (I-62) | (Ia1-1-2) | (b2-c-28) |
| (I-63) | (Ia1-1-3) | (b2-c-28) |
| (I-64) | (Ia1-1-4) | (b2-c-28) |
| (I-65) | (Ia1-1-5) | (b2-c-28) |
| (I-66) | (Ia1-1-6) | (b2-c-28) |
| (I-67) | (Ia1-1-7) | (b2-c-28) |
| (I-68) | (Ia1-1-8) | (b2-c-28) |

TABLE 3

| SALT (I) | Sulfonic acid | organic cation |
|---|---|---|
| (I-69) | (Ia1-1-9) | (b2-c-28) |
| (I-70) | (Ia1-1-10) | (b2-c-28) |
| (I-71) | (Ia1-1-11) | (b2-c-28) |
| (I-72) | (Ia1-1-12) | (b2-c-28) |
| (I-73) | (Ia1-1-1) | (b2-c-31) |
| (I-74) | (Ia1-1-2) | (b2-c-31) |
| (I-75) | (Ia1-1-3) | (b2-c-31) |
| (I-76) | (Ia1-1-4) | (b2-c-31) |
| (I-77) | (Ia1-1-5) | (b2-c-31) |
| (I-78) | (Ia1-1-6) | (b2-c-31) |
| (I-79) | (Ia1-1-7) | (b2-c-31) |
| (I-80) | (Ia1-1-8) | (b2-c-31) |

TABLE 3-continued

| SALT (I) | Sulfonic acid | organic cation |
|---|---|---|
| (I-81) | (Ia1-1-9) | (b2-c-31) |
| (I-82) | (Ia1-1-10) | (b2-c-31) |
| (I-83) | (Ia1-1-11) | (b2-c-31) |
| (I-84) | (Ia1-1-12) | (b2-c-31) |
| (I-85) | (Ia1-1-1) | (b2-c-2) |
| (I-86) | (Ia1-1-2) | (b2-c-2) |
| (I-87) | (Ia1-1-5) | (b2-c-2) |
| (I-88) | (Ia1-1-6) | (b2-c-2) |
| (I-89) | (Ia1-1-9) | (b2-c-2) |
| (I-90) | (Ia1-1-10) | (b2-c-2) |
| (I-91) | (Ia1-1-1) | (b2-c-6) |
| (I-92) | (Ia1-1-2) | (b2-c-6) |
| (I-93) | (Ia1-1-5) | (b2-c-6) |
| (I-94) | (Ia1-1-6) | (b2-c-6) |
| (I-95) | (Ia1-1-9) | (b2-c-6) |
| (I-96) | (Ia1-1-10) | (b2-c-6) |
| (I-97) | (Ia1-1-1) | (b2-c-15) |
| (I-98) | (Ia1-1-2) | (b2-c-15) |
| (I-99) | (Ia1-1-5) | (b2-c-15) |
| (I-100) | (Ia1-1-6) | (b2-c-15) |
| (I-101) | (Ia1-1-9) | (b2-c-15) |
| (I-102) | (Ia1-1-10) | (b2-c-15) |

TABLE 4

| SALT (I) | Sulfonic acid | organic cation |
|---|---|---|
| (I-103) | (Ia1-1-1) | (b2-c-18) |
| (I-104) | (Ia1-1-2) | (b2-c-18) |
| (I-105) | (Ia1-1-5) | (b2-c-18) |
| (I-106) | (Ia1-1-6) | (b2-c-18) |
| (I-107) | (Ia1-1-9) | (b2-c-18) |
| (I-108) | (Ia1-1-10) | (b2-c-18) |
| (I-109) | (Ia1-1-1) | (b2-c-30) |
| (I-110) | (Ia1-1-2) | (b2-c-30) |
| (I-111) | (Ia1-1-5) | (b2-c-30) |
| (I-112) | (Ia1-1-6) | (b2-c-30) |
| (I-113) | (Ia1-1-9) | (b2-c-30) |
| (I-114) | (Ia1-1-10) | (b2-c-30) |

Preferred examples of SALT (I) include those represented as follow.

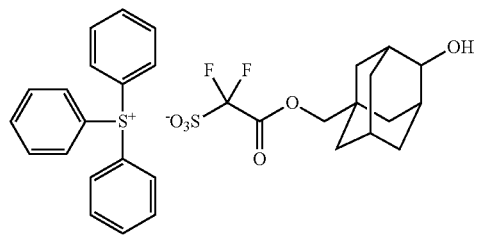

(I-1)

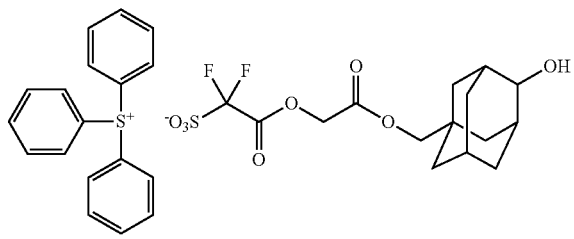

(I-2)

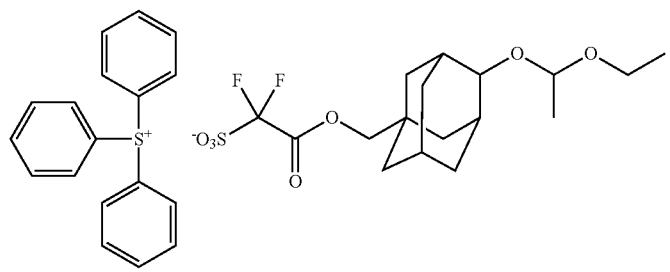

(I-5)

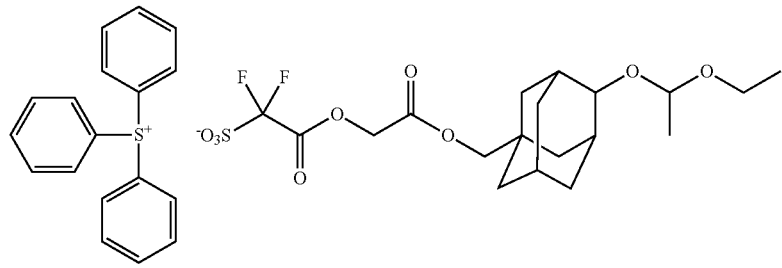

(I-6)

-continued
(I-9)
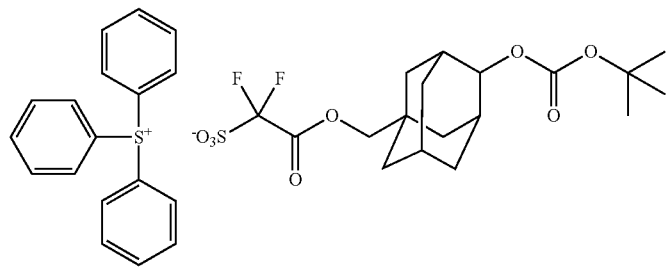
(I-10)
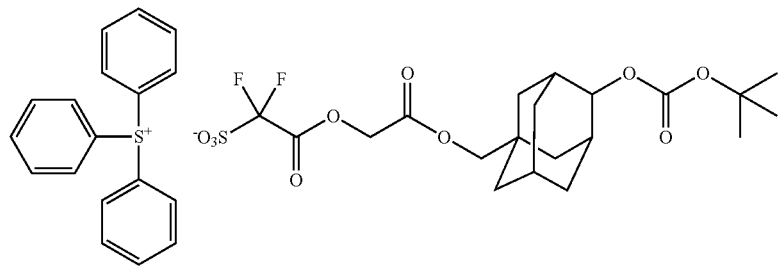
(I-13)
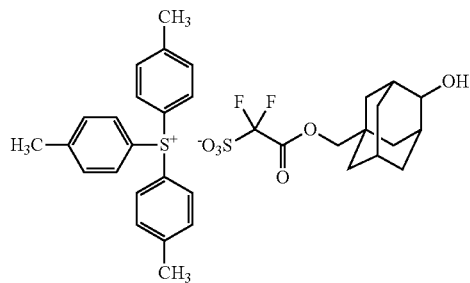
(I-14)
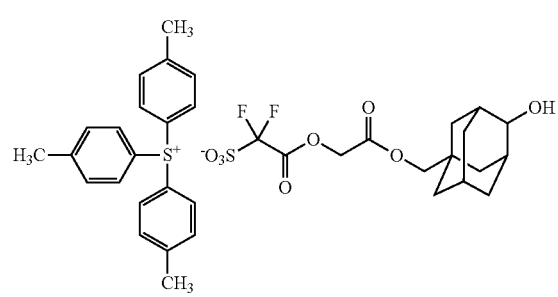
(I-17)
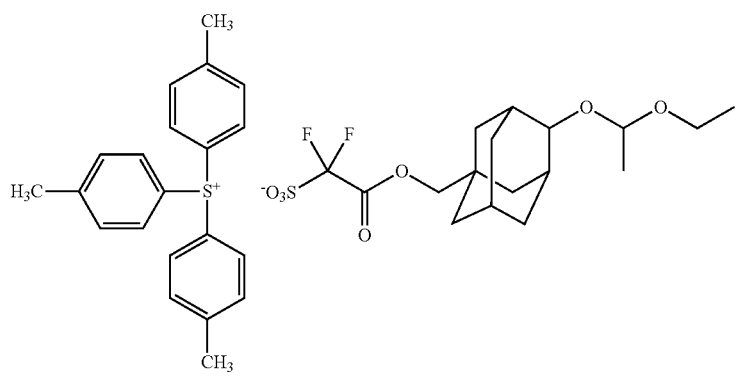
(I-18)
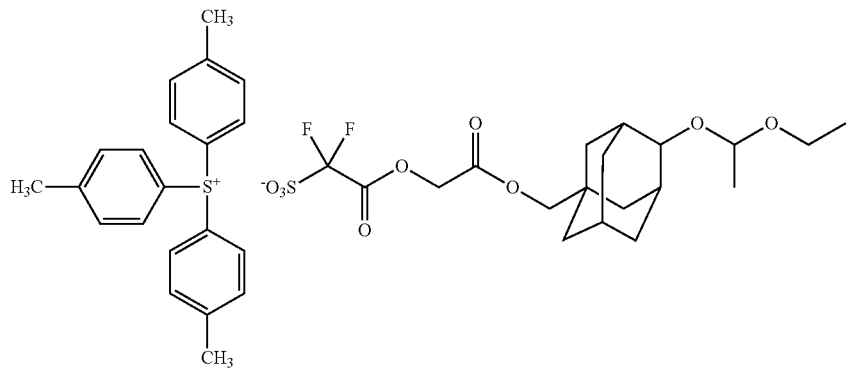

(I-21)
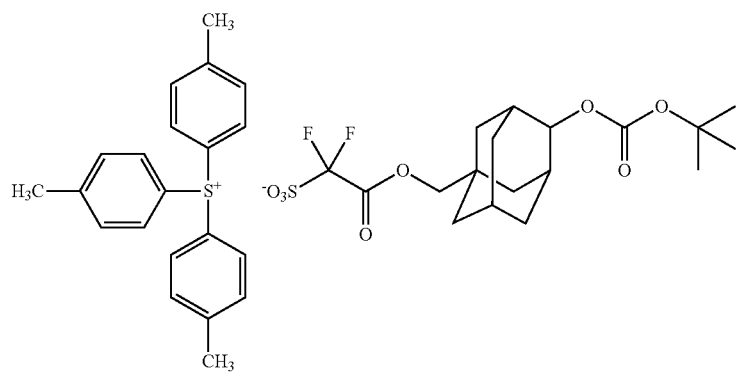
(I-22)
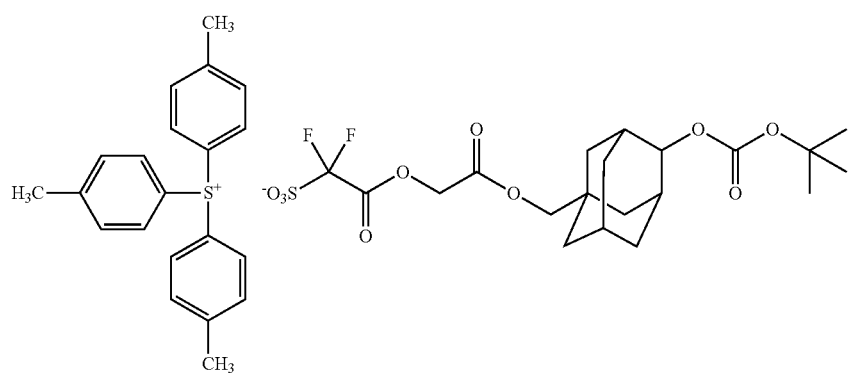
(I-25)
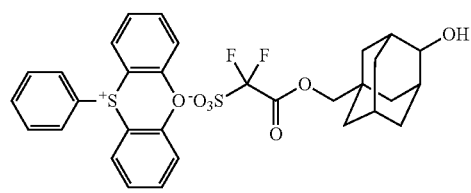
(I-26)
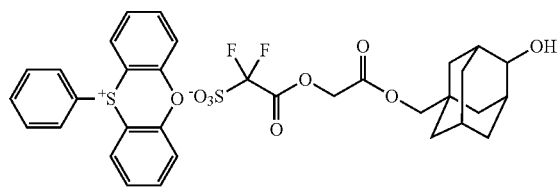
(I-29)
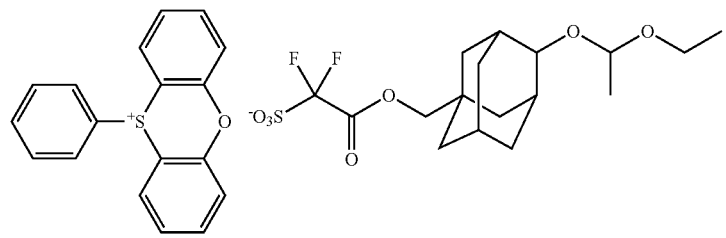
(I-30)
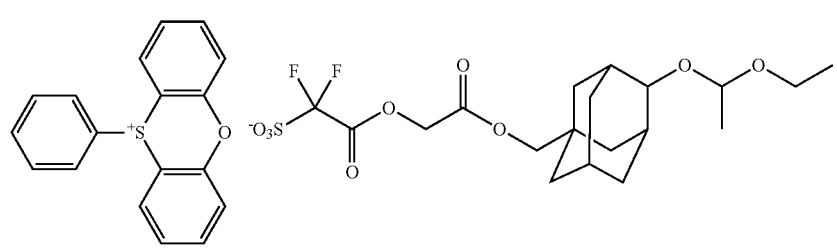

-continued
(I-33)
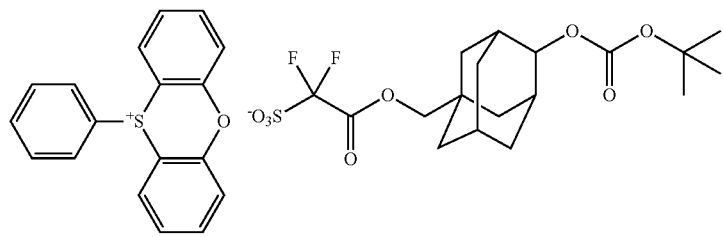
(I-34)
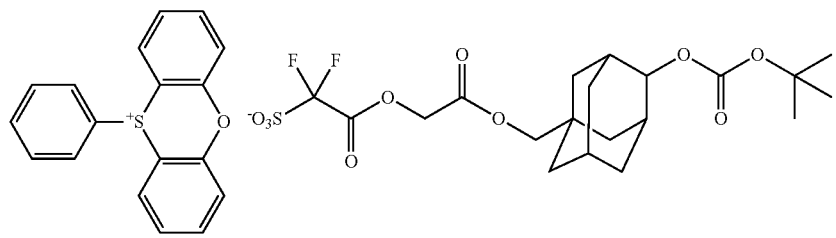
(I37) (I-38)
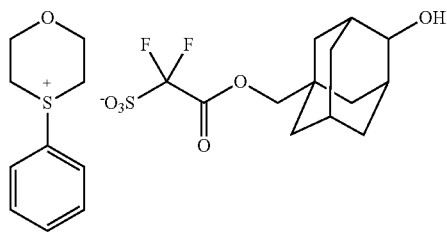 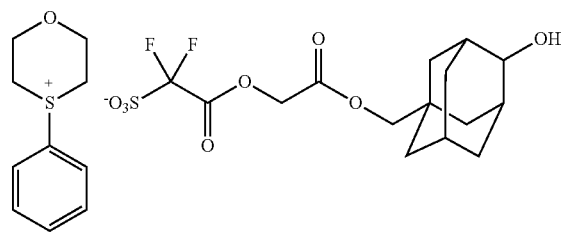
(I-41) (I-42)
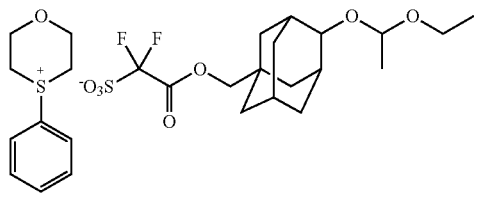 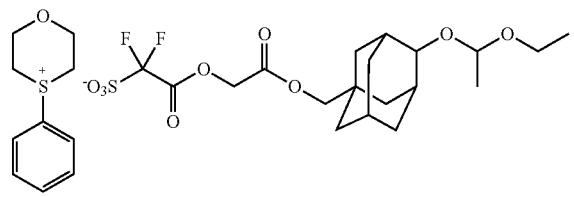
(I-45) (I-46)
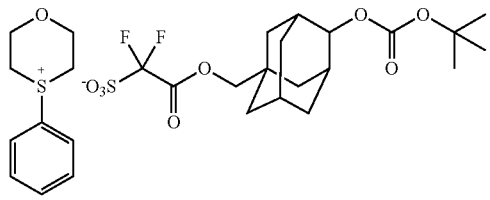 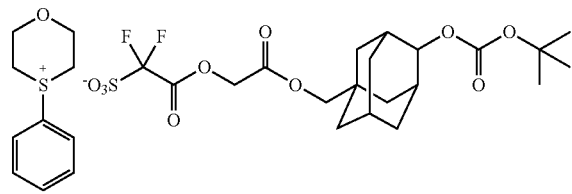
(I-49) (I-50)
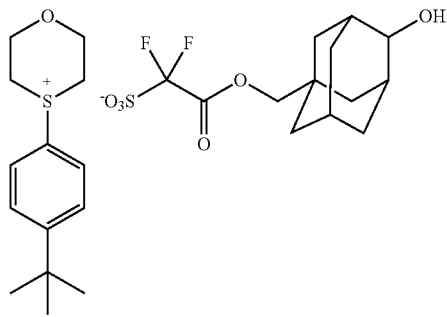 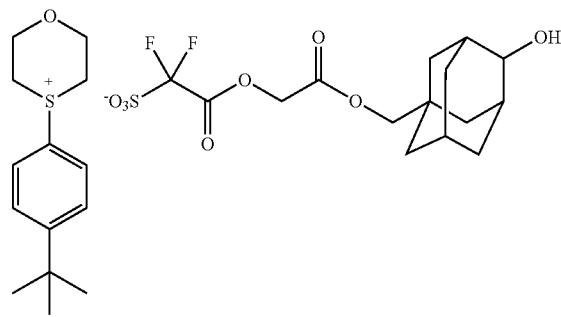

-continued
(I-53) 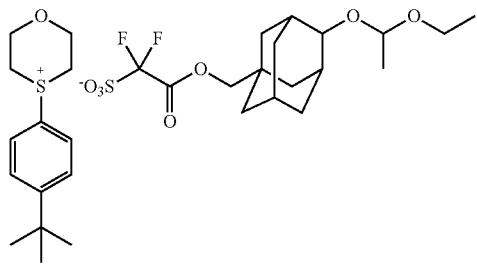
(I-54) 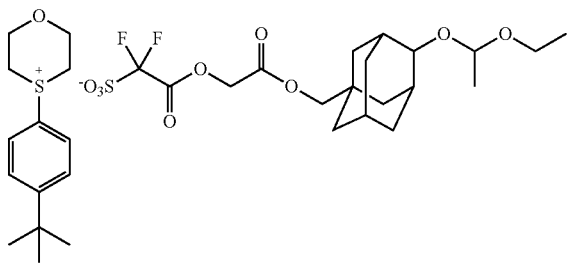
(I-57) 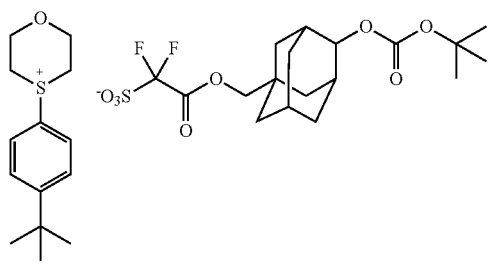
(I-58) 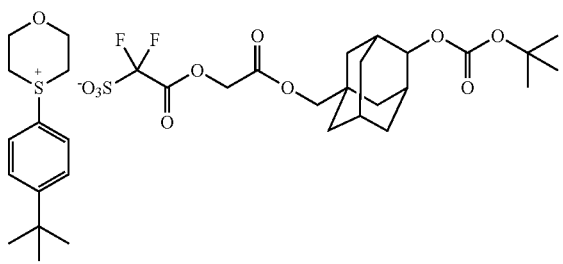
(I-61) 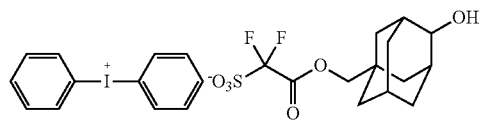
(I-62) 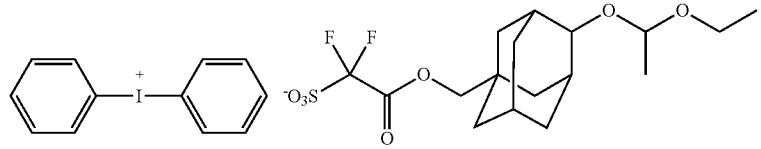
(I-65) 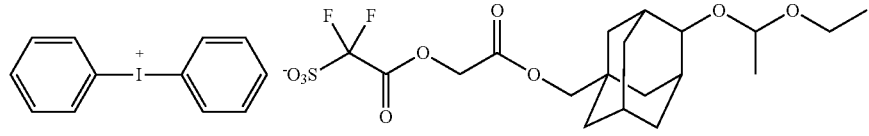
(I-66) 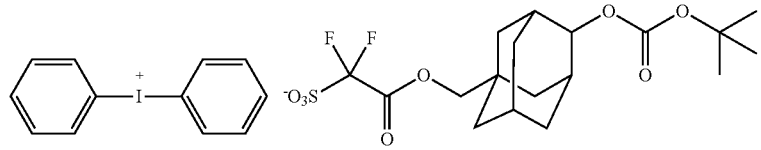
(I-69) 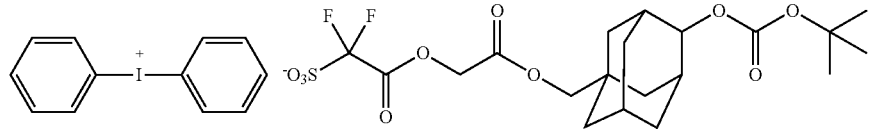
(I-70) 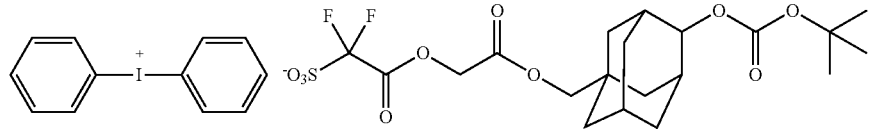
(I-73) 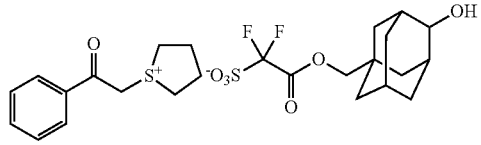
(I-74) 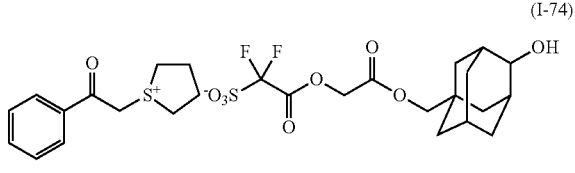

-continued

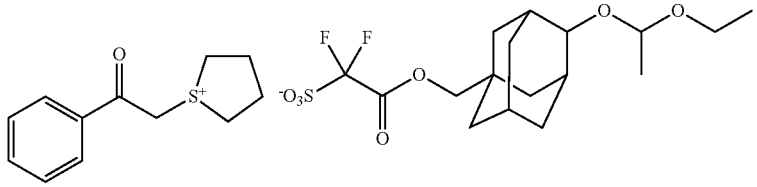
(I-77)

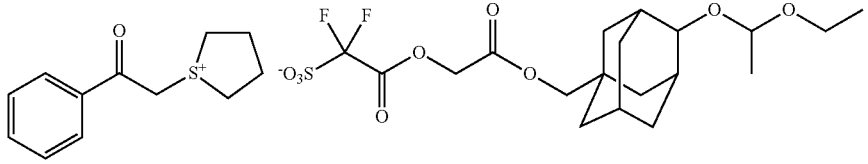
(I-78)

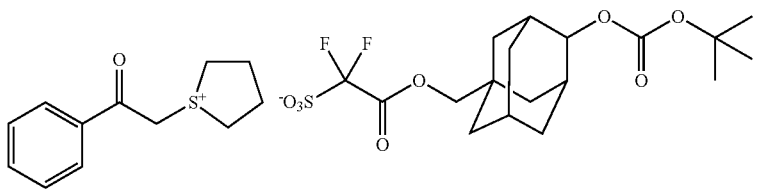
(I-81)

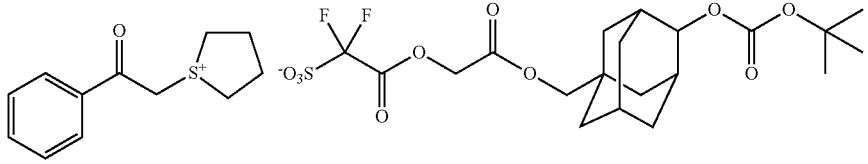
(I-82)

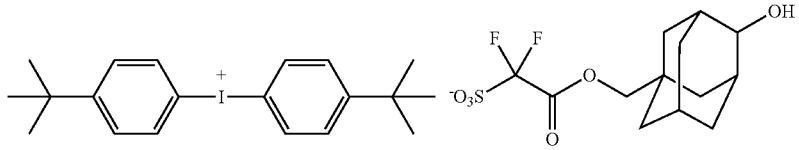
(I-109)

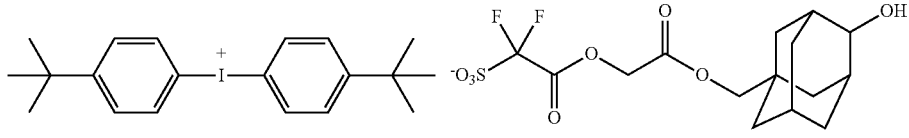
(I-110)

The process for producing SALT (I) will be illustrated. The SALT (I) wherein $R^1$ of the formula is a hydroxy group can be produced by reducing the compound represented by formula (I-b) in a solvent such as acetonitrile or water.

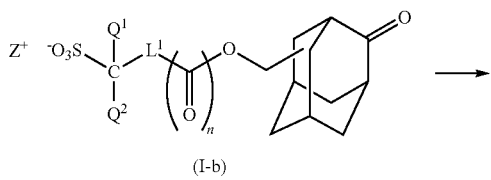
(I-b)

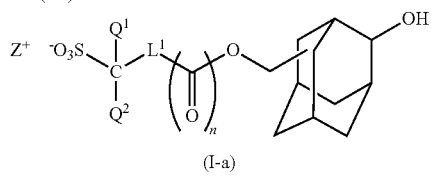
(I-a)

wherein $Q^1$, $Q^2$, $L^1$, n and $Z^+$ are the same as defined above.

The salt represented by formula (I-b) can be reduced with a reducing agent such as sodium borohydride.

Taking the compound represented by formula (b1-a) which $L^1$ is a single bond and n=1 in the formula (I) as an example of the compound represented by formula (I-b), The compound represented by formula (I-b) can be produced by reacting the compound represented by formula (b1-b) and the compound represented by formula (b1-c) in a solvent such as acetonitrile or chloroform, as illustrated as below:

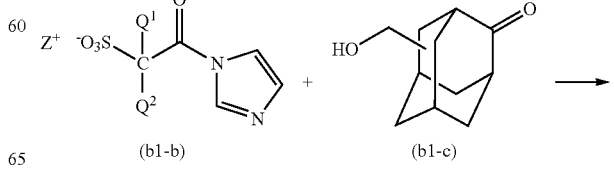
(b1-b)     (b1-c)

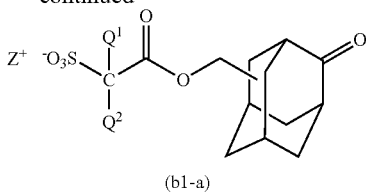

(b1-a)

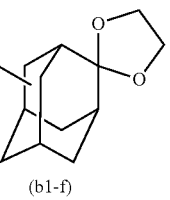

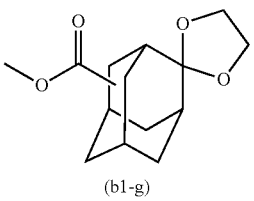

(b1-g)  (b1-f)

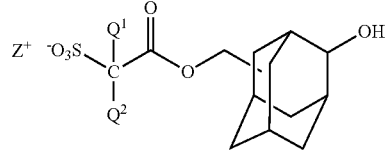

(b1-a)

The compound represented by formula (b1-g) can be reduced with a reducing agent such as lithium aluminum hydride.

The compound represented by formula (b1-g) can be produced by reacting the compound represented by formula (b1-h) and ethylene glycol in the presence of an acid, such as sulfuric acid, in a solvent such as toluene, as shown below.

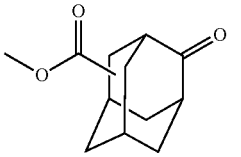

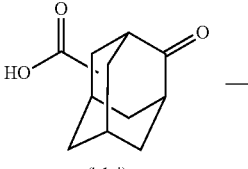

(b1-h)  (b1-g)

wherein $Q^1$, $Q^2$ and $Z^+$ are the same as defined above.

The compound represented by formula (b1-b) can be produced by reacting the compound represented by formula (b1-d) and the compound represented by formula (b1-e) in a solvent such as acetonitrile, as shown below:

The compound represented by formula (b1-h) can be produced by reacting the compound represented by formula (b1-j) with carbonyl diimidazole in a solvent such as chloroform, followed by being reacted with methanol, as shown below:

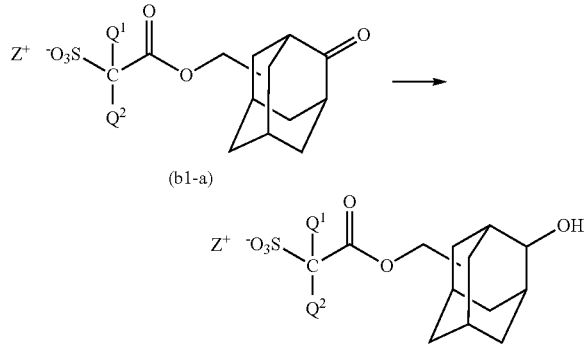

(b1-d)  (b1-e)

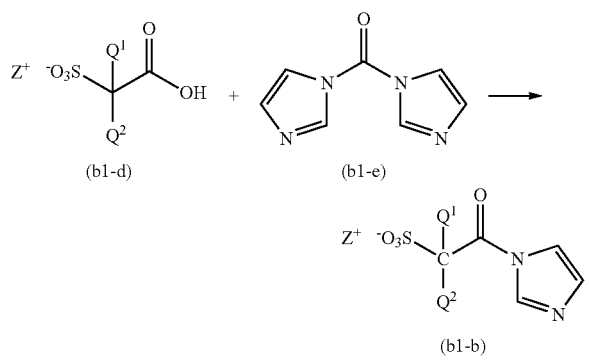

(b1-j)

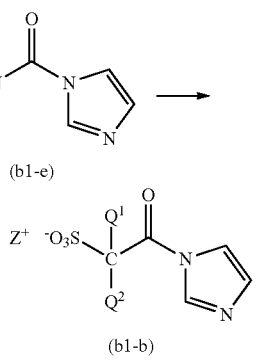

(b1-b)

(b1-i)  (b1-h)

wherein $Q^1$, $Q^2$ and $Z^+$ are the same as defined above.

The compound represented by formula (b1-d) can be produced by the method mentioned in JP2000-13551A1.

The compound represented by formula (b1-c) can be produced by reacting the compound represented by formula (b1-f) in the presence of an acid, e.g. hydrochloric acid, in a solvent such as acetonitrile, as shown below:

The compound represented by formula (b1-j) includes various oxoamadantyl carbonate, which is available on the market. Examples of oxoamadantyl carbonate available on the market include a compound of the formula.

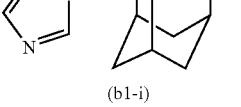

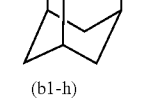

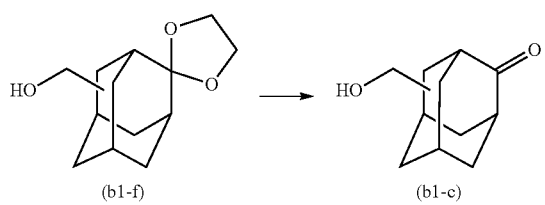

(b1-f)  (b1-c)

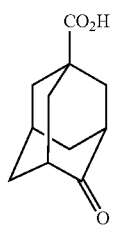

The compound represented by formula (b1-f) can be produced by reducing the compound represented by formula (b1-g) in the presence of an acid, such as sulfuric acid, in a solvent such as tetrahydrofuran, as shown below.

The compound represented by formula (b1-e) is available on the market.

The photoresist composition of the present invention comprises SALT (I) as an acid generator. The photoresist composition can contain two or more kinds of SALT (I). The photoresist composition may contain a salt other than SALT (I). The salt other than SALT (I) may be either ionic or non-ionic one.

The salt other than SALT (I) may be a salt comprising different cation and anion from those of SALT (I), or a salt comprising the same cation as SALT (I) and a different known anion from that of SALT (I).

Preferable examples of the salt other than SALT (I) include those represented by the formulae (B1-1) to (B1-20). The salts containing a triphenylsulfonium cation or a tritolylsulfonium cation are more preferable, and the salts represented by the formulae (B1-1), (B1-2), (B1-3), (B1-6), (B1-7), (B1-11), (B1-12), (B1-13) and (B1-14) are still more preferable.

(B1-1)

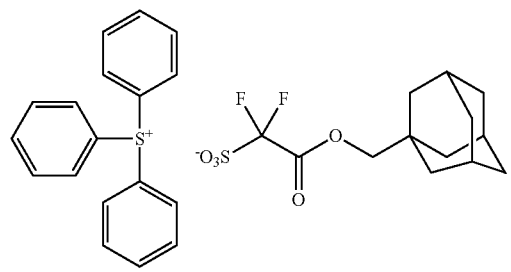

(B1-2)

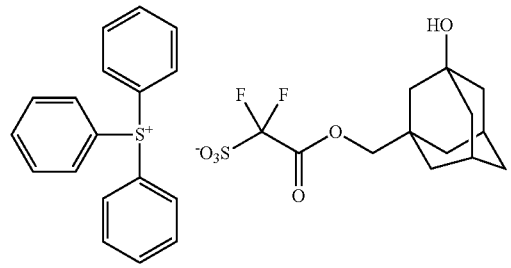

(B1-3)

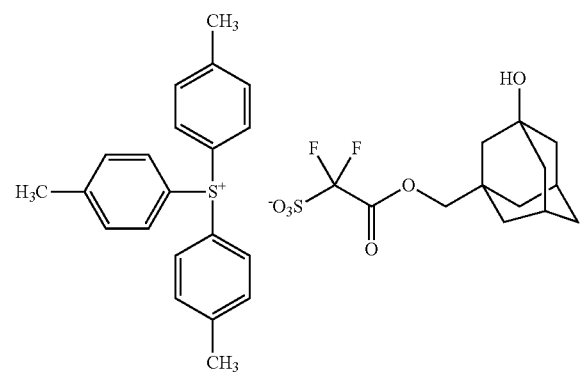

-continued (B1-4)

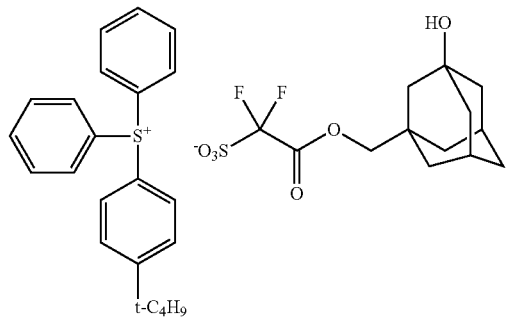

(B1-5)

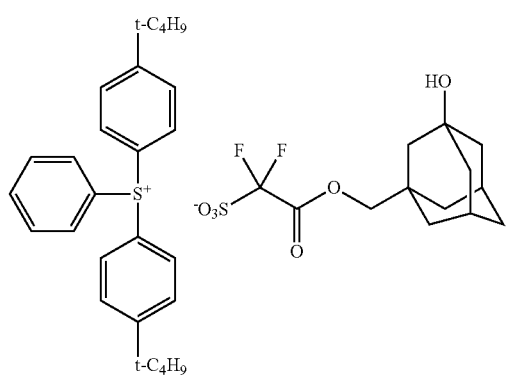

(B1-6)

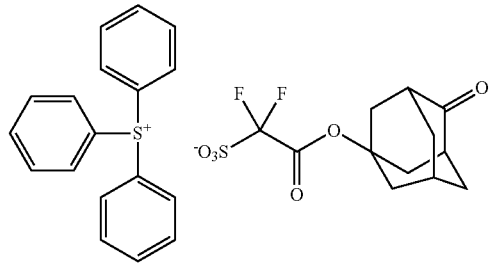

(B1-7)

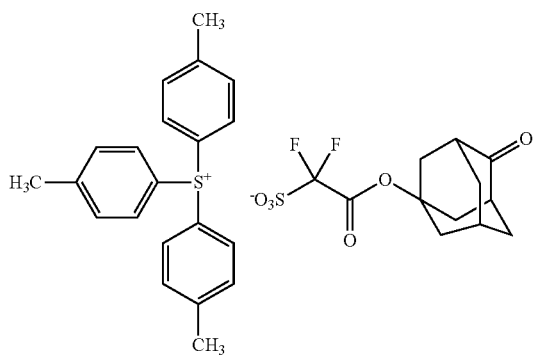

(B1-8) 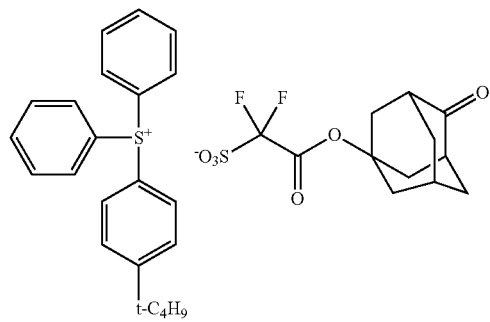
(B1-9) 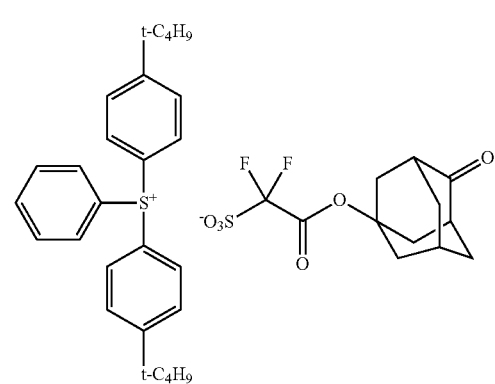
(B1-10) 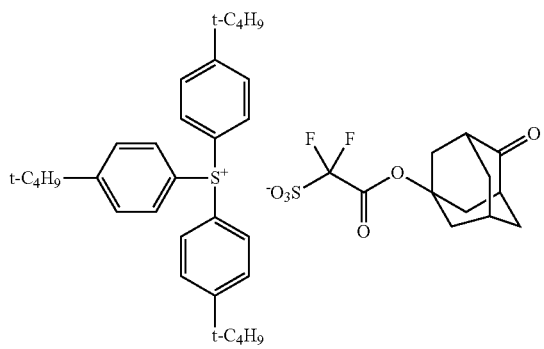
(B1-11) 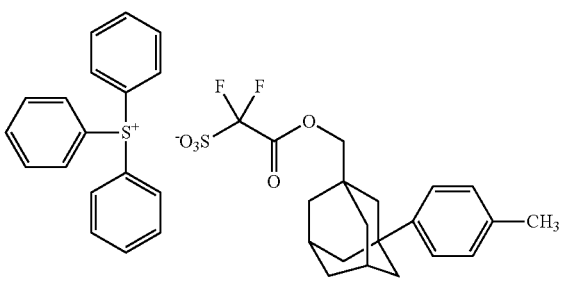
(B1-12) 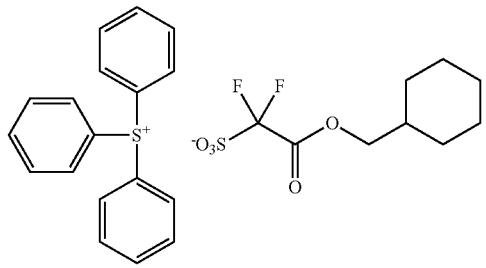
(B1-13) 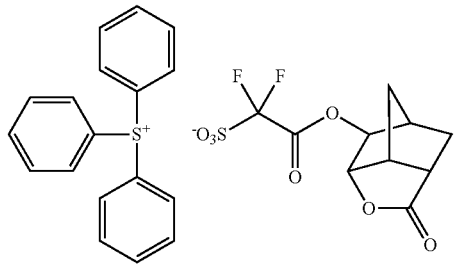
(B1-14) 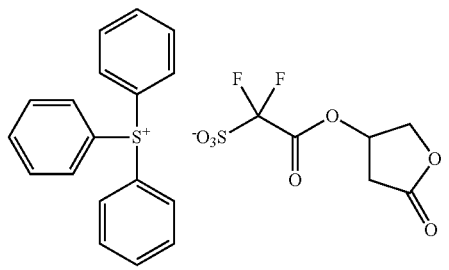
(B1-15) 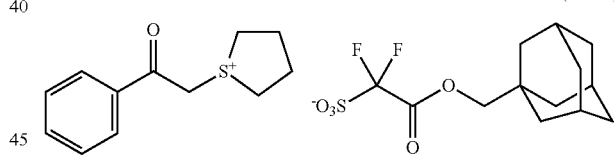
(B1-16) 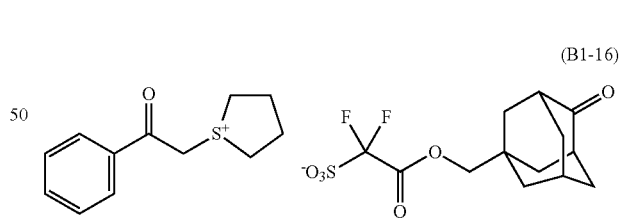
(B1-17) 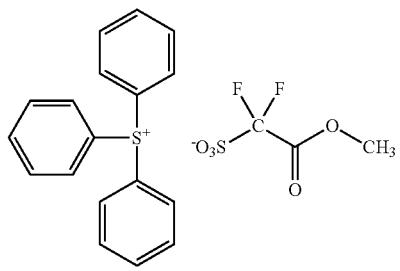

-continued (B1-18)
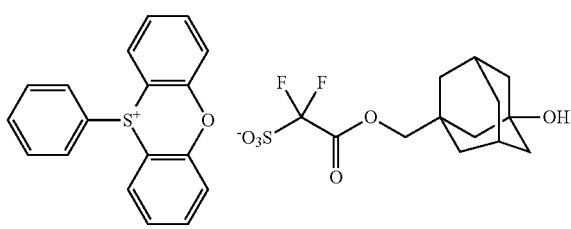

(B1-19)
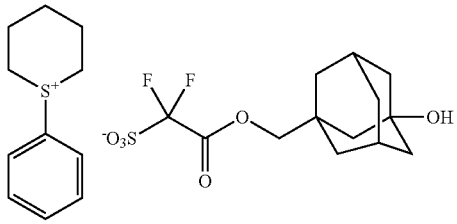

(B1-20)
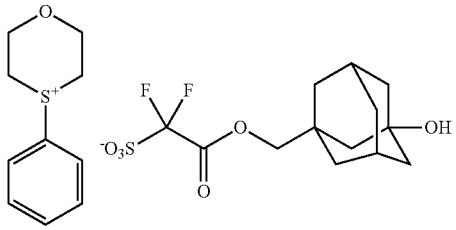

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound and an ammonium salt. Amine compound includes an aliphatic amine and an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

The basic compounds include preferably a compound represented by the formulae (C1), (C2), (C3), (C4), (C5), (C6), (C7) and (C8), more preferably a compound represented by the formulae (C1-1).

(C1)

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxy group, an amino group and a C1-C6 alkoxy group, and the aromatic hydrocarbon group can have a substituent selected from the group consisting of C1-C6 alkyl groups, a C5-C10 alicyclic hydrocarbon group, a hydroxy group, an amino group, and a C1-C6 alkoxy group, (C1-1)
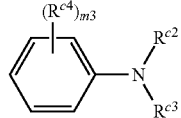

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3, (C2)
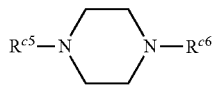

(C3)
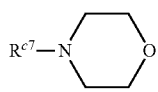

(C4)

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8, (C5)
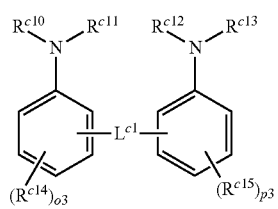

(C6)
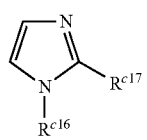

wherein each of $R^{c10}$, $R^{c11}$, $R^{c12}$, $R^{c13}$ and $R^{c16}$ is defined same as $R^{c1}$, each of $R^{c14}$, $R^{c15}$ and $R^{c17}$ is defined same as $R^{c4}$, $L^{c1}$ represents a C1-C6 alkanediyl group, —CO—, —C(=NH)—, —S— or a combination thereof, and o3 and p3 respectively represent an integer of 0 to 3, (C7)
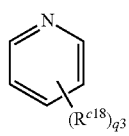

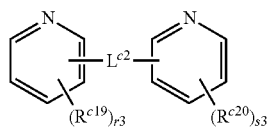

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A1.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The photoresist compositions of the present invention usually contain a solvent.

Examples of the solvent include a glycol ether ester such as ethyl cellosolve acetate, methyl cellosolve acetate and propylene glycol monomethyl ether acetate; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, in a solvent, an acid generator containing the SALT (I), and a resin (A), and if necessary a basic compound and/or additives at a suitable ratio for the composition, optionally followed by filtrating the mixture with a filter having 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist composition of the present invention usually contains 80% by weight or more of the resins based on sum of solid component. The photoresist composition of the present invention usually contains 99% by mass or less of the resins based on sum of solid component. In this specification, "solid component" means components other than solvent in the photoresist composition.

When the photoresist composition contains the resin (X), the content of the resin (X) is usually 0.1 to 30 weight parts, preferably 0.5 to 20 weight parts, more preferably 1 to 15 weight parts relative to 100 weight parts of the resin (A) The content of SALT (I) is preferably 1 parts by weight or more and more preferably 3 parts by weight or more, and the content of SALT (I) is preferably 30 parts by weight or less and more preferably 25 parts by weight or less, per 100 parts by weight of the total resin of the photoresist composition. When the acid generator of the present invention contains SALT (I) and the acid generator other than SALT (I), the content of SALT (I) is preferably 10 parts by weight or more and more preferably 30 parts by weight or more per 100 parts by weight of the total acid generator of the photoresist composition.

When the photoresist compositions contain the basic compound, the content thereof is usually 0.01 to 5%, preferably 0.01 to 3%, more preferably 0.01 to 1% by weight based on sum of solid component.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention are useful for a chemically amplified photoresist composition.

A photoresist pattern can be produced using the photoresist composition of the present invention by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film to form a photoresist pattern.

The applying of the photoresist composition on a substrate is usually conducted using a conventional apparatus such as spin coater. The photoresist composition is preferably filtrated with filter having 0.2 µm of a pore size before applying. Examples of the substrate include a silicon wafer or a quartz wafer on which a sensor, a circuit, a transistor or the like is formed. The substrate may be coated with a reflect-preventing layer such as one containing hexamethyldisilazane. For forming the reflect-preventing layer, such composition for organic reflect-preventing layer as available on the market can be used.

The photoresist film is usually formed by heating the cost layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

Exposure through a mask makes the composition layer have exposed areas and unexposed area. At the exposed area, the acid generator contained in the component layer gives an acid due to exposure energy. The acid generated from the acid generator acts on an acid-labile group of the resin, so that the deprotection reaction proceeds, resulting that the resin shows hydrophilic. Therefore, the resin becomes soluble with an alkaline solution at exposed area of the composition layer. On the other hand, unexposed area of the composition layer remains insoluble or poorly soluble in an aqueous alkali solution even after exposure. The solubility for an aqueous alkali solution is much different between the exposed area and unexposed area.

The step of baking of the exposed photoresist film is so called post-exposure bake, which is conducted with heating means such as hot plates. The temperature of baking of the exposed photoresist film is preferably 50 to 200° C., and more preferably 70 to 150° C. The deprotection reaction further proceeds by post-exposure bake.

The development of the baked photoresist film is usually carried out with alkaline developer using a development apparatus. The development can be conducted by contacting the baked photoresist film into with an aqueous alkaline solution to thereby remove the film at exposed area from the substrate while remain the film at unexposed area, forming the photoresist pattern. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, EUV exposure lithography and EB (electron beam) lithography, particularly for ArF excimer laser lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 µL] using standard polystyrene as a standard reference material.

Structures of compounds were determined by mass spectrometry (Liquid Chromatography; 1100 Type, manufactured by AGILENT TECHNOLOGIES LTD., Mass Spectrometry: LC/MSD Type, manufactured by AGILENT TECHNOLOGIES LTD.). Hereinafter, the value of the peak in the mass spectrometry is referred to as "MASS".

Synthesis Example 1

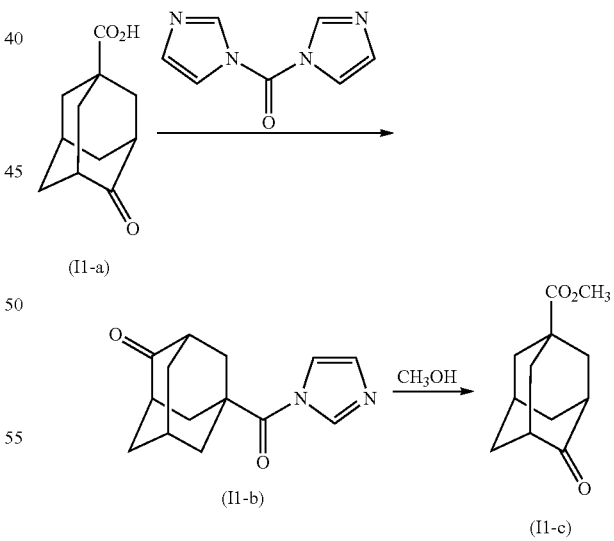

Feeding 10 parts of the compound represented by formula (I1-a) and 50 parts of chloroform into a reactor, they was stirred at 23° C. for 30 minutes, and then 9.18 parts of carbonyldiimidazole was added thereto. Then the resulting mixture was heated to 60° C., stirred at the same temperature for 1 hour, followed by being cooled to approximately 23° C. to give a reaction solution containing the compound represented by formula (I1-b). Into the reaction solution, 1.81 parts of methanol was fed at approximately 23° C., stirring it for 12 hours.

Into the reaction solution, 12.5 parts of deionized water was added thereto, followed by stirring it at 23° C. for 30 minutes. Then setting it still, an organic layer was separated. Washing with water was conducted three times. After washing with water, the resulting organic layer was concentrated to give 10.72 parts of the compound represented by formula (I1-c).

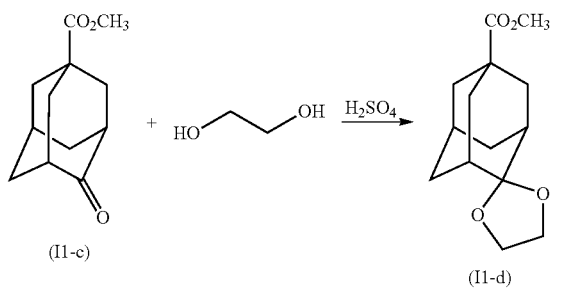

Feeding 9.06 parts of the compound represented by formula (I1-c), 5.4 parts of ethylene glycol, 0.21 parts of sulfuric acid and 68 parts of toluene into a reactor, they were mixed under reflux (inner temperature approximately 105° C.) for 2 hours, followed by cooling it 23° C. To the reaction mixture, 34 parts of 10% aqueous potassium carbonate solution was added and then stirred at 23° C. for 30 minutes. The resulting mixture was set still to separate into an organic layer. Washing with water was conducted three times.

Filtrating the resulting organic layer to remove insoluble matters therefrom, the filtrate was concentrated to give 9.26 parts of the compound represented by formula (I1-d).

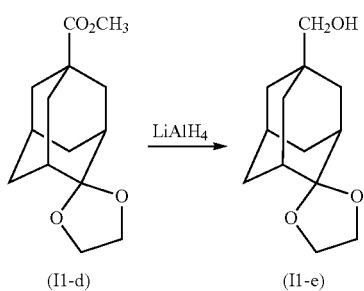

To 10.56 parts of tetrahydrofuran at 0° C., 2.78 parts of lithium aluminum hydride was added and then dropped thereto over 1 hour was a solution in which 9.26 parts of the compound represented by formula (I1-d) was dissolved in 21.16 parts of tetrahydrofuran.

Setting the temperature at approximately 23° C., the resulting mixture was stirred for 12 hours. To the resulting reaction mixture, 52.9 parts of ethyl acetate was added little by little, 105.8 parts of deionized water was fed thereinto, followed by stirring it at 23° C. for 30 minutes. Then it was set still to separate into an organic layer. Washing with water was conducted twice. The resulting organic layer was filtrated to remove insoluble matters therefrom, followed by concentrating it to give 7.05 parts of the compound represented by formula (I1-e).

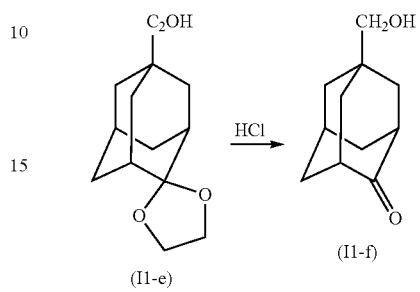

Feeding 3.17 parts of the compound represented by formula (I1-e), 15.85 parts of acetonitrile and 15.85 parts of methanol thereto, they were stirred at 23° C. for 30 minutes. Thereto 0.14 parts of hydrochloric acid and 12.68 parts of deionized water were added and then heated to approximately 50° C., followed by stirring it at the same temperature for 6 hours to obtain a reaction mixture.

Concentrating the reaction mixture, 31.7 parts of ethyl acetate was added thereto and stirred, followed by being set still to separate into an organic layer. To the resulting organic layer, 7.93 parts of 10% aqueous potassium hydrocarbonate solution was added and stirred at 23° C. for 30 minutes, followed by being set still to separate into an organic layer. Such washing with water was conducted twice.

The resulting organic layer was filtrated to remove insoluble matters therefrom, followed by concentrating it to give 1.72 parts of the compound represented by formula (I1-f).

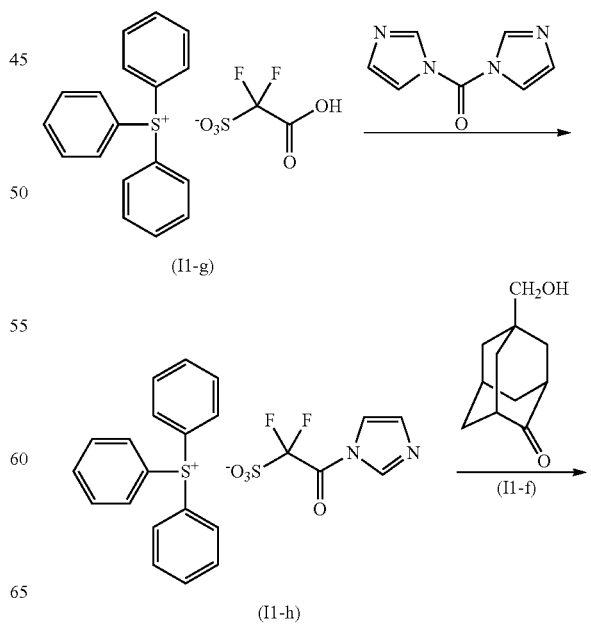

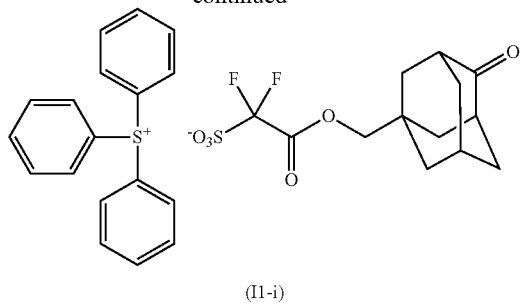

(I1-i)

Feeding 3.5 parts of the compound represented by formula (I1-g) and 17.5 parts of chloroform into a reactor, they were mixed at 23° C. for 30 minutes. Then 1.54 parts of carbonyldiimidazole was added thereto, heated to 80° C., and then stirred at the same temperature for 1 hour to give a reaction mixture containing the compound represented by formula (I1-h). To the reaction mixture, dropped over 1 hour was a solution in which 1.71 parts of the compound represented by formula (I1-f) was dissolved in 4.59 parts of acetonitrile, stirring them at 80° C. for 1 hour to obtain a reaction mixture. The reaction mixture was concentrated, and 35 parts of chloroform and 8.75 parts of deionized water were added thereto, and then stirred at 23° C. for 30 minutes. The resulting mixture was set still to separate into an organic layer. Such washing with water was conducted five times. To the resulting organic layer 0.5 parts of active carbon was added and then stirred at 23° C. for 30 minutes, followed by filtrating it. The filtrate was concentrated and 20 parts of tert-butylmethylether was added and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 3.19 parts of the compound represented by formula (I1-i).

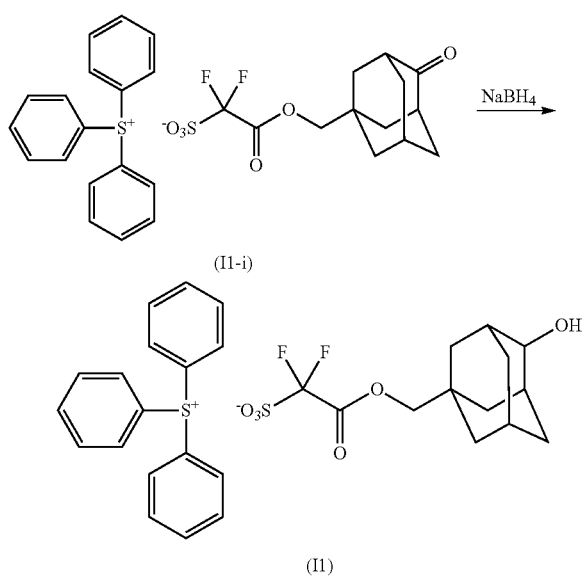

Feeding 2.69 parts of the compound represented by formula (I1-i) and 15 parts of acetonitrile into a reactor, they were stirred at 23° C. for 30 minutes, followed by cooling to 0° C. Thereto dropped over 5 minutes was an aqueous solution in which 0.08 parts of sodium borohydride was dissolved in 0.85 parts of deionized water. Then keeping it at approximately 0° C., the mixture was stirred for 2 hours. Then 2.24 parts of 1N hydrochloric acid was added thereto and stirred to obtain a reaction mixture. Concentrating the reaction mixture, 24 parts of chloroform and 6 parts of deionized water were fed into the resulting concentrate, and they were stirred at 23° C. for 30 minutes. The mixture was set still to separate into an organic layer. Such washing with water was conducted three times. To the resulting organic layer, 10 parts of tert-butylmethylether was added and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 1.88 parts of the salt represented by formula (I1).

MASS(ESI(+) Spectrum): M$^+$ 263.1

MASS(ESI(−) Spectrum): M$^-$ 339.1

Synthesis Example 2

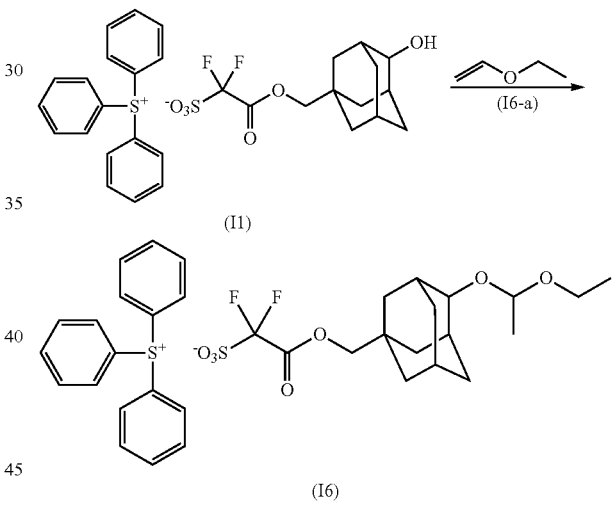

Feeding 5.75 parts of the compound represented by formula (I1) and 36.23 parts of tetrahydrofuran into a reactor, they were stirred at 23° C. for 30 minutes. Thereto added was a solution in which 0.00036 parts of p-toluenesulfonic acid was dissolved in 0.18 parts of tetrahydrofuran, 1.38 parts of the compound represented by formula (I6-a) was dropped, followed by stirring it at 23° C. for 3 hours.

To the reaction mixture 0.03 parts of triethylamine was added and then concentrated. To the resulting concentrates 50 parts of ethyl acetate and 20 parts of deionized water were added and stirred, followed by being set still to separate into an organic layer. Such washing with water was conducted three times.

Filtrating the resulting organic layer to remove insoluble matters therefrom, the filtrate was concentrated to obtain 3.89 parts of the compound represented by formula (I6).

MASS(ESI(+) Spectrum): M$^+$ 263.1

MASS(ESI(−) Spectrum): M$^-$ 411.1

Synthesis Example 3

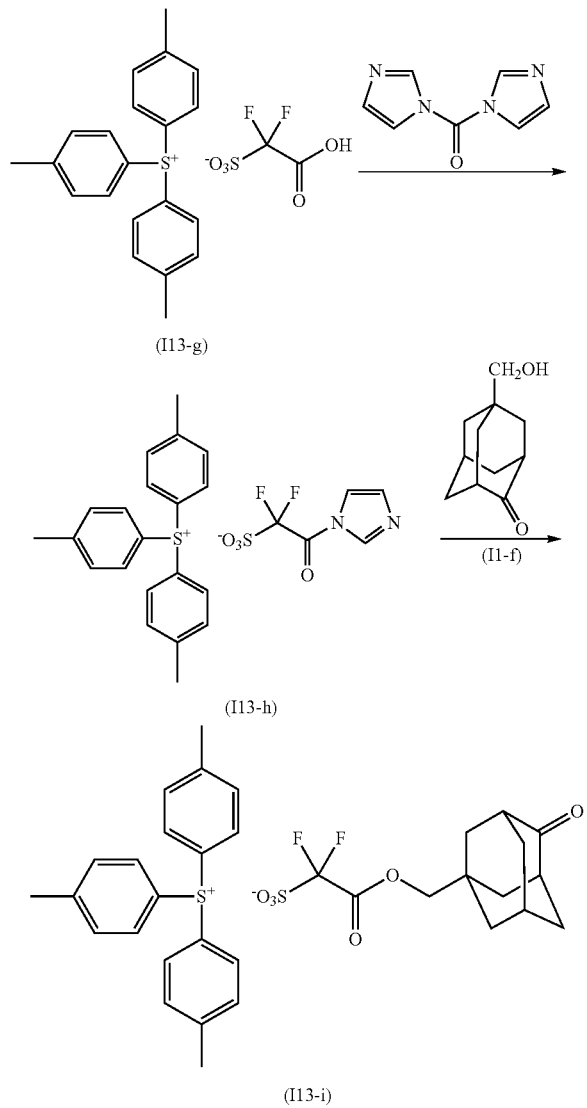

Feeding 3.84 parts of the compound represented by formula (I13-g) and 19.2 parts of chloroform into a reactor, they were stirred at 23° C. for 30 minutes. Then 1.54 parts of carbonyldiimidazole was added thereto, stirred at 80° C. for 1 hour to give a reaction solution containing the compound represented by formula (I13-h). The compound represented by formula (I1-f) was produced according to the method of Example 1.

Into the reaction solution, dropped over 1 hour was a solution in which 1.71 parts of the compound represented by formula (I1-f) was dissolved in 4.59 parts of acetonitrile, and then stirred at 80° C. for 1 hour. The reaction mixture was concentrated. To the resulting concentrate, 40 parts of chloroform and 10 parts of deionized water were added, and then stirred at 23° C. for 30 minutes, followed by being set still to separate into an organic layer. Such washing with water was conducted further five times. To the resulting organic layer 0.5 parts of active carbon was added and then stirred at 23° C. for 30 minutes, followed by filtrating it.

The filtrate was concentrated and 20 parts of tert-butylmethylether was added and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 3.31 parts of the salt represented by formula (I13-i).

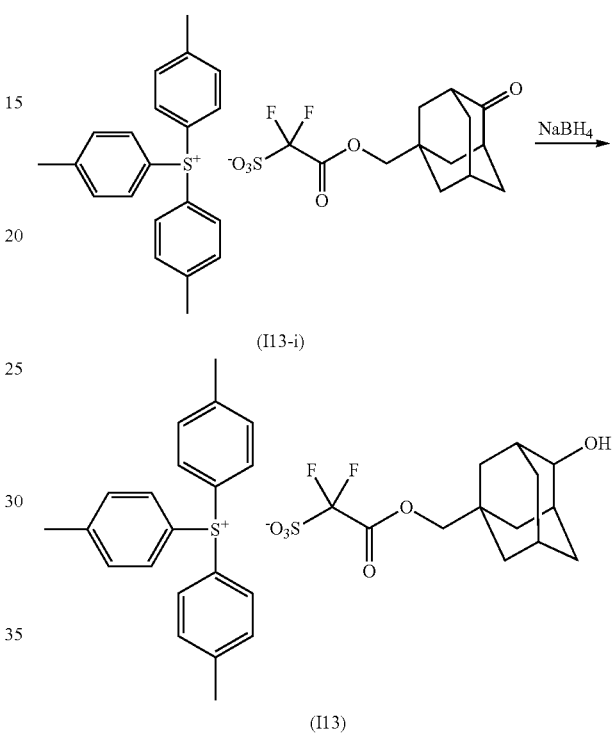

Feeding 2.88 parts of the compound represented by formula (I13-i) and 15 parts of acetonitrile into a reactor, they were stirred at 23° C. for 30 minutes, followed by cooling to 0° C. Thereto dropped over 5 minutes was an aqueous solution in which 0.08 parts of sodium borohydride was dissolved in 0.85 parts of deionized water. Then keeping it at approximately 0° C., the mixture was stirred for 2 hours. Then 2.24 parts of 1N hydrochloric acid was added thereto and stirred to obtain a reaction mixture. Concentrating the reaction mixture, 30 parts of chloroform and 10 parts of deionized water were fed into the resulting concentrate, and they were stirred at 23° C. for 30 minutes. The mixture was set still to separate into an organic layer. Such washing with water was conducted three times. To the resulting organic layer, 10 parts of tert-butylmethylether was added and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 2.04 parts of the salt represented by formula (I13).

MASS(ESI(+) Spectrum): $M^+$ 305.1

MASS(ESI(−) Spectrum): $M^-$ 339.1

Synthesis Example 4

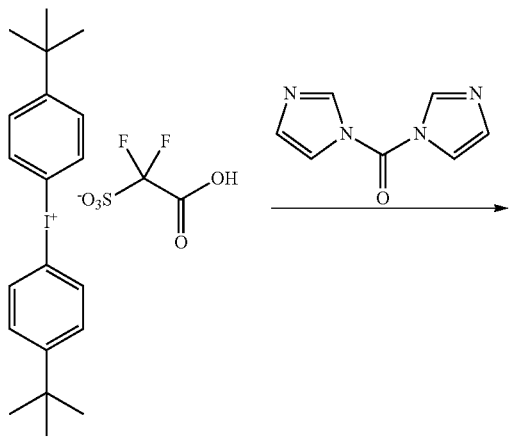

(I109-g)

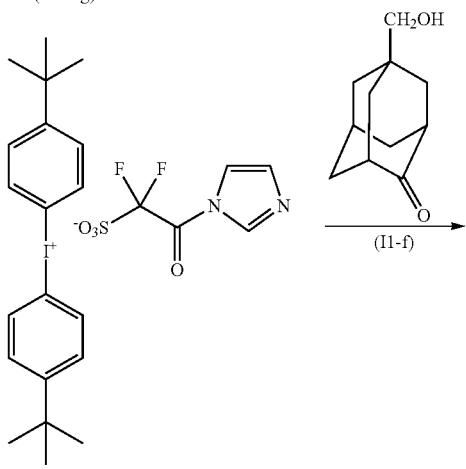

(I109-h)

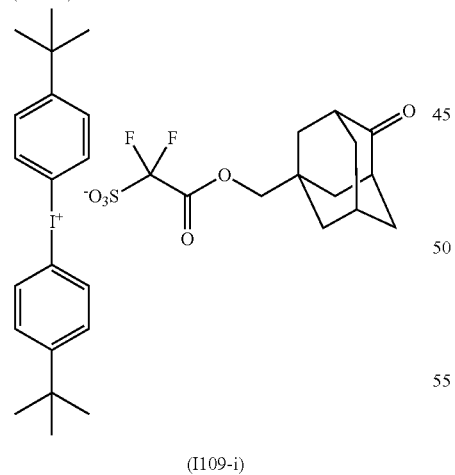

(I109-i)

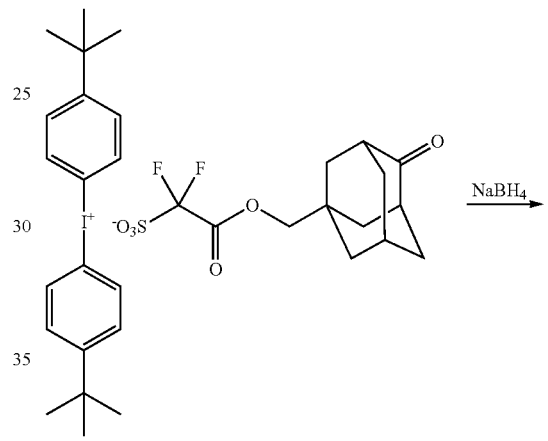

(I109-i)

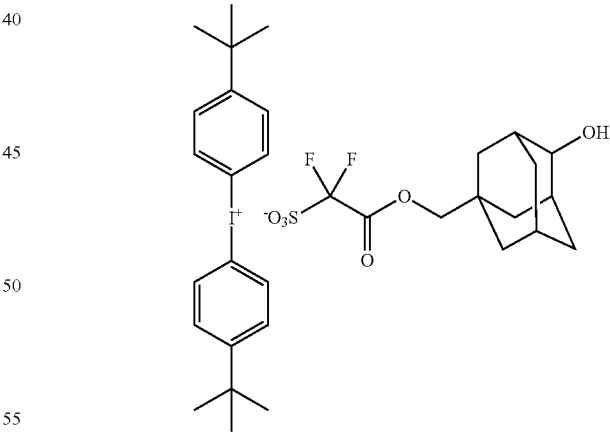

(I109)

Feeding 4.54 parts of the compound represented by formula (I109-g) and 22.7 parts of chloroform into a reactor, they were stirred at 23° C. for 30 minutes. Then 1.54 parts of carbonyldiimidazole was added thereto, stirred at 80° C. for 1 hour to give a reaction solution containing the compound represented by formula (I109-h). The compound represented by formula (I1-f) was produced according to the method of Example 1. Into the reaction solution, dropped over 1 hour was a solution in which 1.71 parts of the compound represented by formula (I1-f) was dissolved in 4.59 parts of acetonitrile, and then stirred at 80° C. for 1 hour. The reaction mixture was concentrated. To the resulting concentrate, 40 parts of chloroform and 10 parts of deionized water were added, and then stirred at 23° C. for 30 minutes, followed by being set still to separate into an organic layer. Such washing with water was conducted further five times. To the resulting organic layer 0.5 parts of active carbon was added and then stirred at 23° C. for 30 minutes, followed by filtrating it. The filtrate was concentrated and 20 parts of tert-butylmethylether was added and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 4.12 parts of the salt represented by formula (I109-i).

Feeding 3.27 parts of the compound represented by formula (I109-i) and 20 parts of acetonitrile into a reactor, they were stirred at 23° C. for 30 minutes, followed by cooling to 0° C. Thereto dropped over 5 minutes was axe aqueous solution in which 0.08 parts of sodium borohydride was dissolved in 0.85 parts of deionized water. Then keeping it at approximately 0° C., the mixture was stirred for 2 hours. Then 2.24 parts of 1N hydrochloric acid was added thereto and stirred to obtain a reaction mixture. Concentrating the reaction mixture, 40 parts of chloroform and 15 parts of deionized water were fed into the resulting concentrate, and they were stirred at 23° C. for 30 minutes. The mixture was set still to separate into an organic layer. Such washing with water was conducted three times. To the resulting organic layer, 10 parts of tert-butylmethylether was added and then a supernatant was removed therefrom. The resulting residue was concentrated and 10 parts of ethyl acetate was added thereto, followed by stirring them. The resulting supernatant was removed therefrom, and 10 parts of ethyl acetate was added thereto, followed by stirring it. The resulting supernatant was removed therefrom and the residue was concentrated. The concentrate was dissolved in acetonitrile, followed by concentrating it to obtain 2.93 parts of the salt represented by formula (I109).

MS (ESI(+) Spectrum): M+ 393.1
MS (ESI(−) Spectrum): M− 339.1

Synthesis Example 5

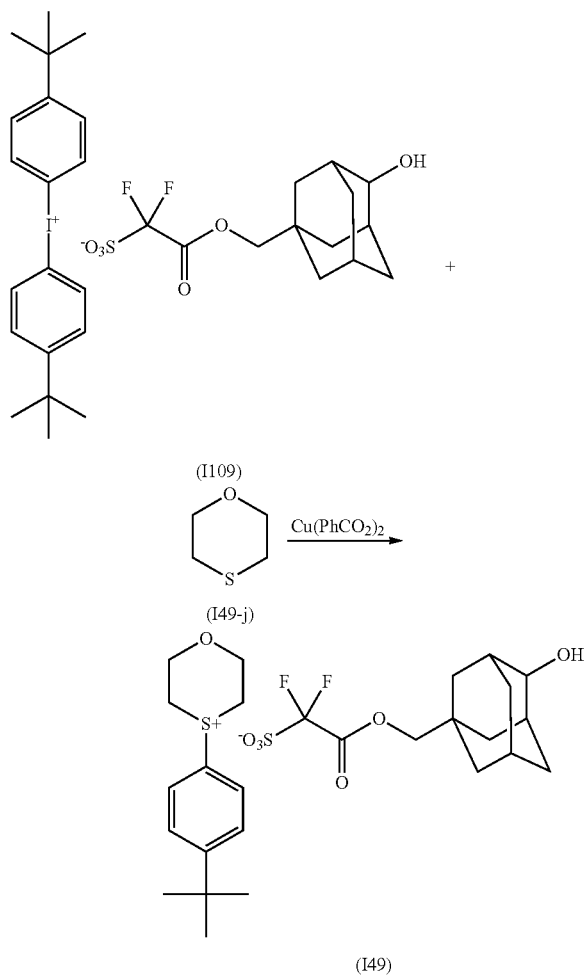

Feeding 2 parts of the compound represented by formula (I109), 0.28 parts of the compound represented by formula (I49-j) and 25 parts of monochlorobenzene into a reactor, they were stirred at 23° C. for 30 minutes. To the resulting mixture, 0.02 parts of copper (II) dibenzoic acid was added, followed by stirring it at 100° C. for 1 hour. The resulting reaction mixture was concentrated and then 20 parts of chloroform and 5 parts of deionized water were added thereto and stirred at 23° C. for 30 minutes, followed by separating into an organic layer. To the collected organic layer, 5 parts of deionized water was added and stirred at 23° C. for 30 minutes, followed by separating into an organic layer. Such washing with water was conducted five times. The resulting organic layer was concentrated, and then 10 parts of tert-butylmethylether was added thereto and stirred, followed by removing a supernatant therefrom. The resulting residue was concentrated, and 10 parts of ethyl acetate was added thereto, followed by stirring it. The resulting supernatant was removed therefrom and the residue was concentrated. The concentrates were dissolved in acetonitrile, followed by concentrating it to obtain 1.12 parts of the salt represented by formula (I49).

MS (ESI(+) Spectrum): M+ 237.1
MS (ESI(−) Spectrum): M− 339.1

Synthesis Example 6

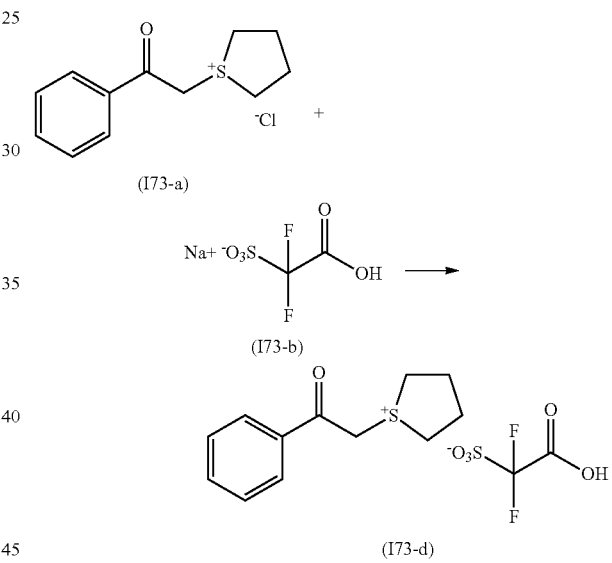

Feeding 10.95 parts of the compound represented by formula (I73-a), 8.96 parts of the compound represented by formula (I73-b), 100 parts of acetonitrile and 50 parts of deionized water into a reactor, they were stirred at 23° C. for 15 hours. The resulting mixture was concentrated, followed by extracting it with 100 parts of chloroform to obtain an organic layer. The organic layer was concentrated to obtain 14.63 parts of the compound represented by formula (I73-d).

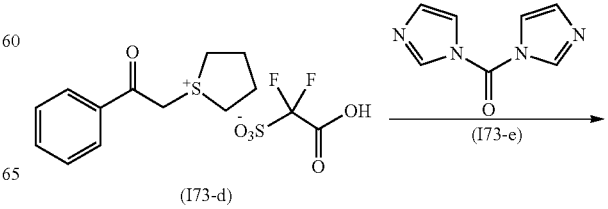

-continued

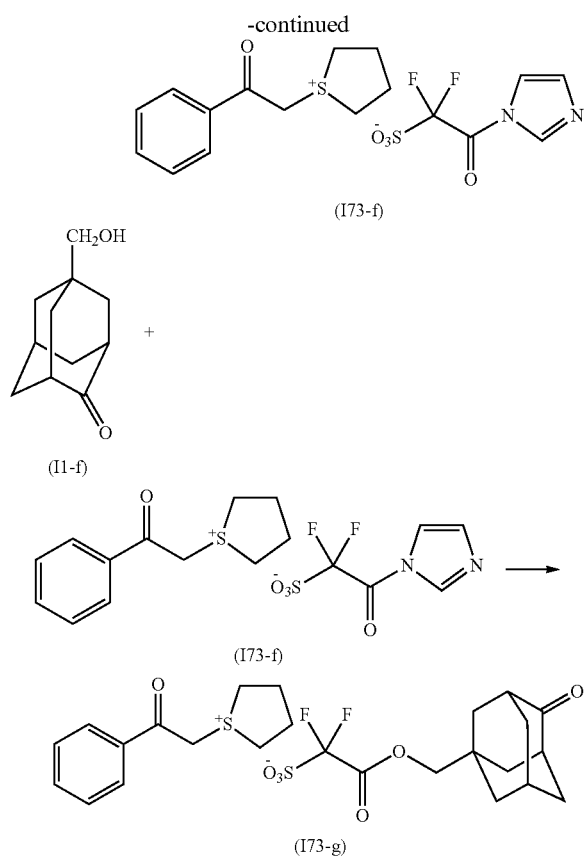

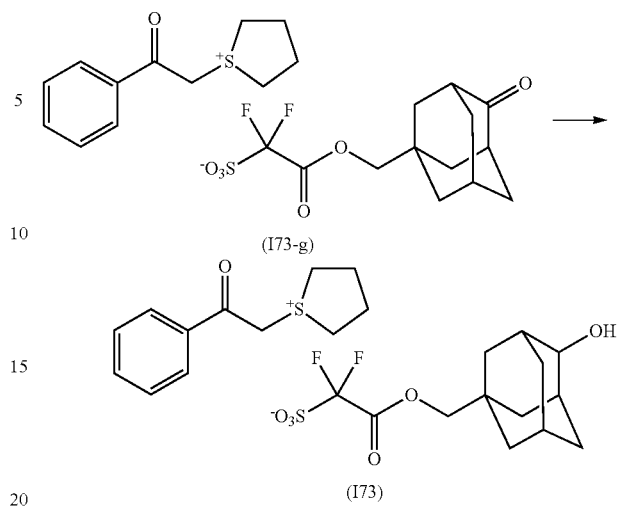

Feeding 2.16 parts of the compound represented by formula (I73-d) and 15 parts of acetonitrile into a reactor, they were stirred at 23° C. for 30 minutes. Then 1.3 parts of the compound represented by formula (I73-e) was added thereto, and then stirred at 70° C. for 2 hour.

The resulting reaction mixture was cooled to 23° C. and then filtrated to obtain a solution containing the compound represented by formula (I73-f). The compound represented by formula (I1-f) was produced according to the method of Example 1.

Into the solution containing the compound represented by formula (I73-f), dropped over 1 hour was a solution in which 1.06 parts of the compound represented by formula (I1-f) was dissolved in 3.18 parts of chloroform, and then stirred at 23° C. for 23 hours.

The reaction mixture was concentrated. To the resulting concentrate, 60 parts of chloroform and 30 parts of 2% aqueous oxalic acid solution were added, and then stirred, followed by separating into an organic layer. Such washing with oxalic acid was conducted five times. To the collected organic layer, 30 parts of deionized water was added thereto and stirred, followed by separating into an organic layer. Such washing with water was conducted five times. The resulting organic layer was concentrated, and 50 parts of tert-butylmethylether was added thereto and stirred to remove a supernatant therefrom. The resulting residue was dissolved in acetonitrile, followed by concentrating it to obtain 1.69 parts of the salt represented by formula (I73-g).

Feeding 1.22 parts of the compound represented by formula (I73-g) and 10 parts of acetonitrile into a reactor, they were stirred at 23° C. for 30 minutes, followed by cooling to 0° C. Thereto dropped over 5 minutes was an aqueous solution in which 0.04 parts of sodium borohydride was dissolved in 0.43 parts of deionized water. Then keeping it at approximately 0° C., the mixture was stirred for 2 hours. Then 1.12 parts of 1N hydrochloric acid was added thereto and stirred to obtain a reaction mixture. Concentrating the reaction mixture, 20 parts of chloroform and 10 parts of deionized water were fed into the resulting concentrate, and they were stirred at 23° C. for 30 minutes. The mixture was set still to separate into an organic layer. Such washing with water was conducted three times. The resulting organic layer was concentrated and 10 parts of tert-butylmethylether was added thereto and then a supernatant was removed therefrom. The resulting residue was concentrated and 10 parts of ethyl acetate was added thereto, followed by stirring them. The resulting supernatant was removed therefrom, and the residue was concentrated. The concentrate was dissolved in acetonitrile, followed by concentrating it to obtain 0.88 parts of the salt represented by formula (I73).

MS (ESI(+) Spectrum): M⁺ 207.1

MS (ESI(−) Spectrum): M⁻ 339.1

Synthesis of Resin

The compounds used for producing resins were shown as follow.

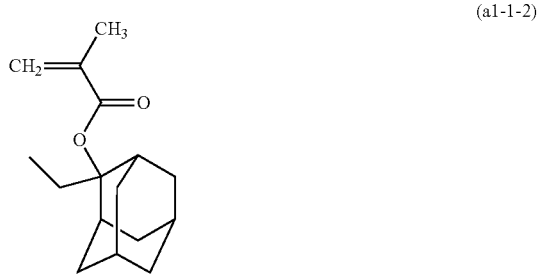

(a1-1-3) 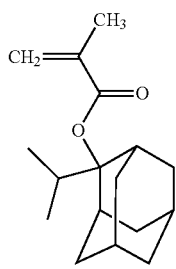

(a1-2-3) 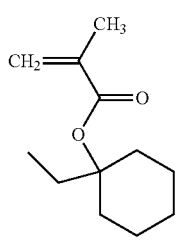

(a1-5-1) 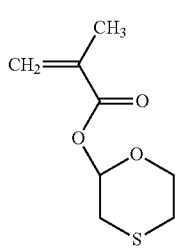

(a2-1-1) 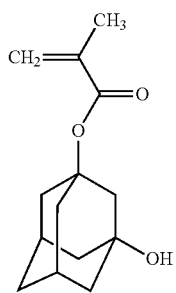

(a3-1-1) 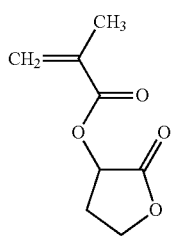

(a3-2-3) 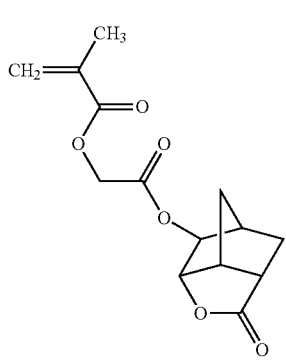

(H) 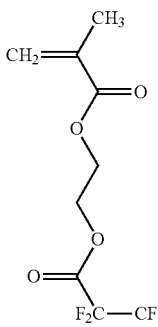

Hereinafter, the compounds of the formulae are referred to as the symbols below the formulae. For example, the compound represented by formula (a1-1-2) is referred to as "monomer (a1-1-2)".

Synthesis Example 7

The monomers (a1-1-3), (a1-2-3), (a2-1-1), (a3-1-1) and (a3-2-3) were mixed in a molar ratio of 30/14/6/20/30 (monomer (a1-1-2)/monomer (a1-2-3)/monomer (a2-1-1)/monomer (a3-1-1)/monomer (a3-2-3)), and 1,4-dioxane was added thereto in the amount ratio of 1.5 times weight parts relative to the total parts of all monomers to prepare a mixture.

To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the resulting reaction mixture was heated at 75° C. for about 5 hours.

The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated again for purification. As a result, a resin having a weight-average molecular weight of about $8.1 \times 10^3$ was obtained in a yield of 65%. This resin is called as resin A1. Resin A1 had the following structural units.

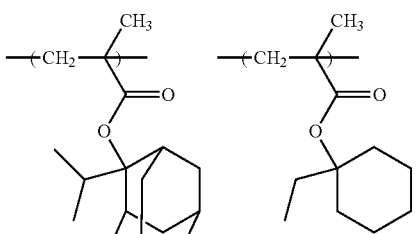
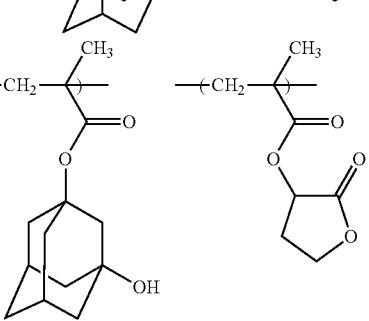

-continued

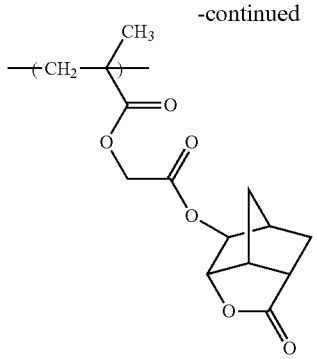

Synthesis Example 8

The monomers (a1-1-2), (a2-1-1) and (a3-1-1) were mixed in a molar ratio of 50/25/25 (monomer (a1-1-2)/monomer (a2-1-1)/monomer (a3-1-1)), and 1,4-dioxane was added thereto in the amount ratio of 1.5 times weight parts relative to the total parts of all monomers to prepare a mixture. To the mixture, azobisisobutyronitrile as an initiator in the molar ratio of azobisisobutyronitrile/all monomer=1/100, and azobis(2,4-dimethylvaleronitrile) as an initiator in the molar ratio of azobis(2,4-dimethylvaleronitrile)/all monomer=3/100 were added, and the obtained mixture was heated at 80° C. for about 8 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about 9.2×10³ was obtained in a yield of 60%.

This resin is called as resin A2. Resin A2 had the following structural units.

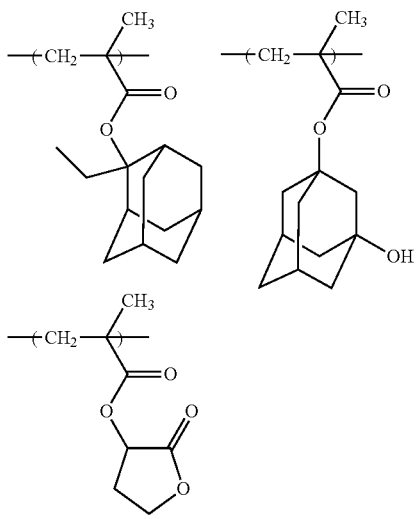

Synthesis Example 9

The monomers (a1-1-3), (a1-2-3), (a2-1-1), (a3-2-3) and (a3-1-1) were mixed in a molar ratio of 30/14/6/20/30 (monomer (a1-1-3)/monomer (a1-2-3)/monomer (a2-1-1)/monomer (a3-2-3)/monomer (a3-1-1)), and 1,4-dioxane was added thereto in the amount ratio of 1.5 times weight parts relative to the total parts of all monomers to prepare a mixture. To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the obtained mixture was heated at 75° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about 7×10³ was obtained in a yield of 60%.

This resin is called as resin A3. Resin A3 had the following structural units.

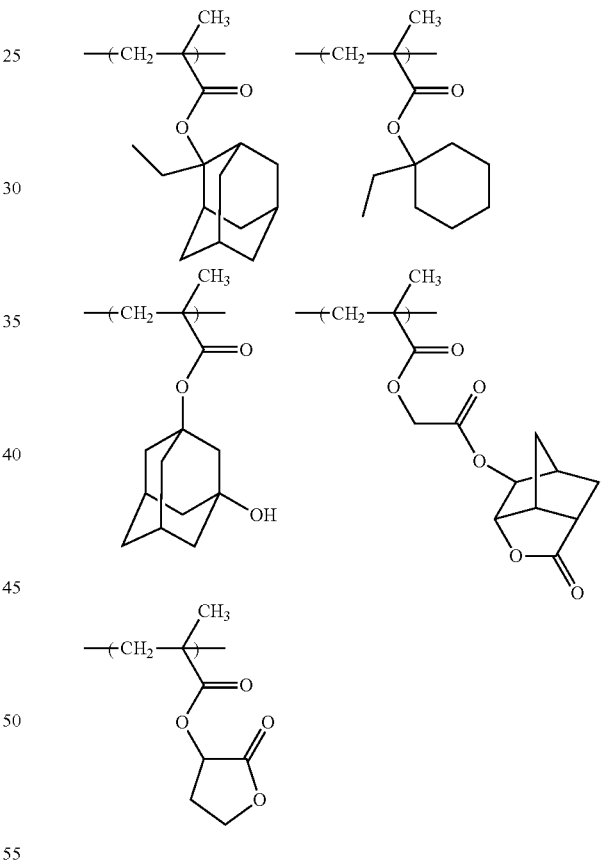

Synthesis Example 10

The monomers (a1-1-3), (a1-5-1), (a2-1-1), (a3-2-3) and (a3-1-1) were mixed in a molar ratio of 30/14/6/20/30 (monomer (a1-1-3)/monomer (a1-5-1)/monomer (a2-1-1)/monomer (a3-2-3)/monomer (a3-1-1)), and 1,4-dioxane was added thereto in the amount ratio of 1.5 times weight parts relative to the total parts of all monomers to prepare a mixture. To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the obtained mixture was heated at 75° C. for about 5 hours.

The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about $7.4 \times 10^3$ was obtained in a yield of 62%. This resin is called as resin A4. Resin A4 had the following structural units

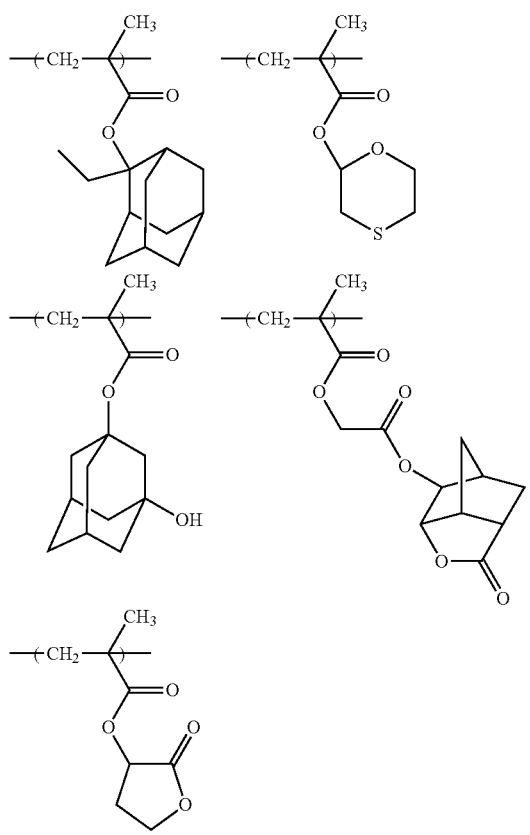

Synthesis Example 11

To monomer (H), 1,4-dioxane was added in the amount ratio of 1.5 times weight parts relative to the total parts of all monomer to prepare a mixture. To the mixture, azobisisobutyronitrile as an initiator in the molar ratio of azobisisobutyronitrile/all monomer=0.7/100 and azobis(2,4-dimethylvaleronitrile) as an initiator in the molar ratio of azobis(2,4-dimethylvaleronitrile)/all monomer=2.1/100 were added, and the obtained mixture was heated at 75° C. for about 5 hours. The reaction mixture obtained was poured into a large amount of a mixture of methanol and water (weight ratio=4/1) to cause precipitation. The precipitate was collected by filtration and then, was dissolved in 1,4-dioxane followed by poured the resultant solution into a large amount of a mixture of methanol and water to cause precipitation. This operation was conducted twice for purification. As a result, a resin having a weight-average molecular weight of about $1.8 \times 10^4$ was obtained in a yield of 77%.

This resin is called as resin X1. Resin X1 had the following structural unit.

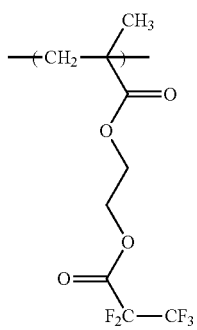

Examples 1 to 11 and Comparative Examples 1 to 2

Preparation of Photoresist Composition

The following components were mixed and dissolved, further, filtrated through a fluorine resin filter having pore diameter of 0.2 μm, to prepare photoresist compositions shown in Table 5.

\<Resin\>
Resin A1, Resin A2, Resin A3, Resin A4, Resin X1
\<Acid Geneator\>
I1: Salt represented by formula (I1)
I6: Salt represented by formula (I6)
I13: Salt represented by formula (I13)
I109: Salt represented by formula (I109)
I49: Salt represented by formula (I49)
I73: Salt represented by formula (I73)
B1:

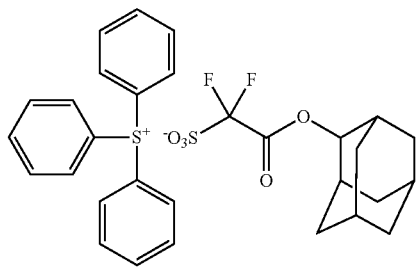

B2:

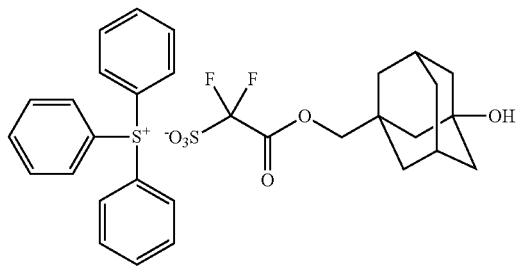

<Quencher>
Basic compound C1; 2,6-diisopropylaniline
<Solvent>

| propylene glycol monomethyl ether acetate | 265 parts |
| propylene glycol monomethyl ether | 20 parts |
| 2-heptane | 20 parts |
| γ-butyrolactone | 3.5 parts |

TABLE 5

| | Acid generator (Parts) | Resin (Parts) | Quencher (Parts) | PB/PEB |
|---|---|---|---|---|
| Ex. 1 | I1 = 1.2 | A1/X1 = 10/0.9 | C1 = 0.07 | 100° C./95° C. |
| Ex. 2 | I1 = 1.2 | A2/X1 = 10/0.9 | C1 = 0.07 | 110° C./105° C. |
| Ex. 3 | I1 = 1.2 | A1 = 10 | C1 = 0.07 | 100° C./95° C. |
| Ex. 4 | I1 = 1.2 | A2 = 10 | C1 = 0.07 | 110° C./105° C. |
| Ex. 5 | I1 = 1.2 | A3/X1 = 10/0.9 | C1 = 0.07 | 100° C./95° C. |
| Ex. 6 | I1 = 1.2 | A4/X1 = 10/0.9 | C1 = 0.07 | 100° C./95° C. |
| Ex. 7 | I13 = 1.2 | A3/X1 = 10/0.9 | C1 = 0.07 | 100° C./95° C. |
| Ex. 8 | I109 = 1.2 | A3/X1 = 10/0.9 | C1 = 0.07 | 100° C./95° C. |
| Ex. 9 | I13/I49 = 0.80/0.40 | A3/X1 = 10/0.9 | C1 = 0.07 | 100° C./95° C. |
| Ex. 10 | I13/I73 = 0.80/0.40 | A3/X1 = 10/0.9 | C1 = 0.07 | 100° C./95° C. |
| Ex. 11 | I6 = 1.2 | A3/X1 = 10/0.9 | C1 = 0.07 | 100° C./95° C. |
| Compar. Ex. 1 | B1 = 1.2 | A2 = 10 | C1 = 0.07 | 110° C./105° C. |
| Compar. Ex. 2 | B2 = 1.2 | A2 = 10 | C1 = 0.07 | 110° C./105° C. |

(Evaluation of CDU)

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating.

Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 5 for 60 seconds. Using an ArF excimer stepper for immersion exposure ("XT: 1900Gi" manufactured by ASML, NA=1.35, 3/4 Annular, X-Y polarization) and a mask forming contact-hole pattern (hole pitch 100 nm/diameter of hole 70 nm), each wafer thus formed with the respective resist film was subjected to line and space pattern exposure with the exposure quantity being varied stepwise. Ultra pure water was used for immersion solvent.

After the exposure, each wafer was subjected to post-exposure baking on a hotplate at a temperature shown in the column "PEB" in Table 5 for 60 seconds and then to paddle development for 60 seconds with an aqueous solution of 2.38 wt % tetramethylammonium hydroxide.

Each of patterns developed on the organic anti-reflective coating substrate after the development was observed with a scanning electron microscope.

Effective Sensitivity (ES) was expressed as the amount of exposure that the line width of the line and space pattern of 55 nm became 1:1 after exposure through line and space pattern mask with 70 nm of diameter of hole and development.

CD uniformity (CDU): The photoresist pattern at ES was observed with a scanning electron microscope. The hole diameter of the contact hole pattern was twenty four (24) times measured and its average diameter was calculated. The average diameters of four hundred (400) holes on the same wafer were respectively measured. When population was the average diameters of four hundred holes, the standard deviation was calculated as CDU. The smaller the standard deviation is, the better pattern profile is.

Further, each of CDU is shown in columns of "CDU".

TABLE 6

| Ex. No. | CDU |
|---|---|
| Ex. 1 | 1.63 |
| Ex. 2 | 1.83 |
| Ex. 3 | 1.62 |
| Ex. 4 | 1.81 |
| Ex. 5 | 1.58 |
| Ex. 6 | 1.59 |
| Ex. 7 | 1.53 |
| Ex. 8 | 1.66 |
| Ex. 9 | 1.51 |
| Ex. 10 | 1.56 |
| Ex. 11 | 1.69 |
| Compar. Ex. 1 | 2.28 |
| Compar. Ex. 2 | 1.91 |

The photoresist composition of the present invention provides a good photoresist pattern with excellent pattern profile. Therefore, the photoresist pattern of the present invention is suitable for semiconductor microfabrication employing lithography process.

What is claimed is:

1. A photoresist composition comprising
(A) a resin which has an acid-labile group-containing structural unit and a lactone ring-containing structural unit, and (B) a salt represented by formula (I):

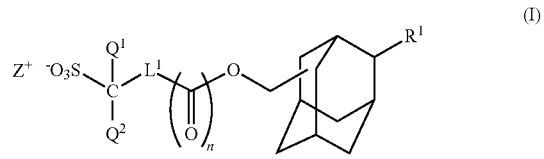

wherein $Q^1$ and $Q^2$ each independently represent a fluorine atom or a C1-C6 perfluoroalkyl group, n represents 0 or 1, $L^1$ represents a single bond or a C1-C10 alkanediyl group in which a methylene group may be replaced by an oxygen atom or a carbonyl group, provided that $L^1$ is not a single bond when n is 0, $R^1$ represents a hydroxy group protected by a protecting group, and $Z^+$ represents an organic cation, said hydroxy group protected by a protecting group being represented by formula (2A):

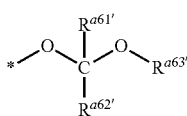
(2A)

wherein $R^{a61'}$ and $R^{a62'}$ independently each represent a hydrogen atom or a C1-C12 monovalent hydrocarbon group, and $R^{a63'}$ represents a C1-C20 monovalent hydrocarbon group, or $R^{a63'}$ represents a C2-C20 divalent hydrocarbon group together with $R^{a62'}$, and a methylene group of the monovalent hydrocarbon groups may be replaced by an oxygen atom or a sulfur atom, and a methylene group of the divalent hydrocarbon groups may be replaced by an oxygen atom or a sulfur atom, and * represents a binding position.

2. The photoresist composition according to claim 1, which further comprises a solvent.

3. The photoresist composition according to claim 1, wherein n is 1.

4. The photoresist composition according to claim 1, 2 or 3, wherein $L^1$ is a single bond.

5. The photoresist composition according to claim 1, 2 or 3, wherein $Z^+$ is an arylsulfonium cation.

6. The photoresist composition according to claim 1, 2 or 3, wherein the lactone ring-containing structural unit is represented by formula (a3-1), formula (a3-2) or formula (a3-3):

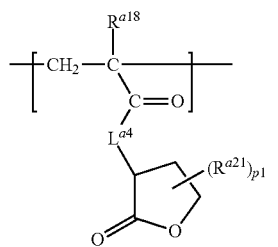
(a3-1)

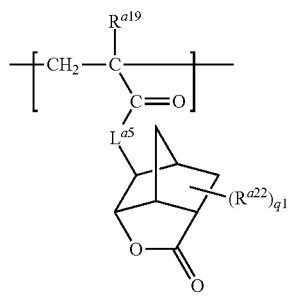
(a3-2)

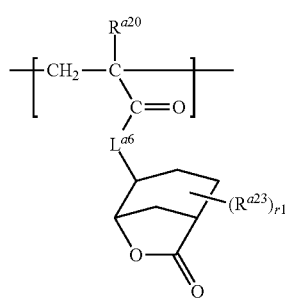
(a3-3)

wherein $L^{a4}$, $L^{a5}$ and $L^{a6}$ each independently represent *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

7. The photoresist composition according to claim 6, wherein the lactone ring-containing structural unit is represented by formula (a3-2) wherein $L^{a5}$ represents *—O—$(CH_2)_{k3}$—CO—O— in which * represents a binding position to —CO— and k3 represents an integer of 1 to 7, and q1 is 0.

8. The photoresist composition according to claim 1, 2 or 3, wherein the acid-labile group-containing structural unit is represented by formula (a1-1) or formula (a1-2):

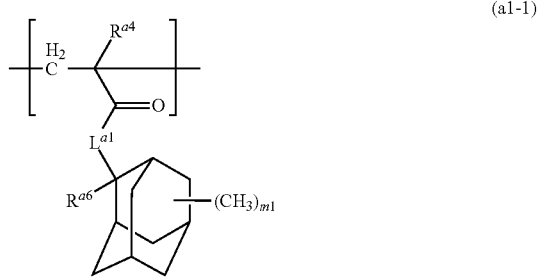
(a1-1)

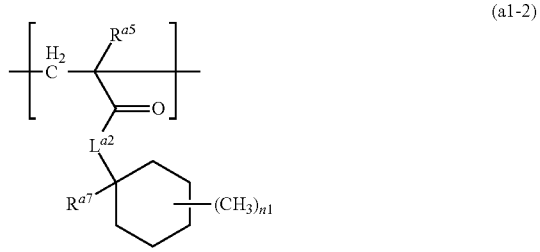
(a1-2)

wherein $L^{a1}$ and $L^{a2}$ each independently represent *—O— or

*—O—$(CH_2)_{k1}$—CO— in which * represents a binding position to —CO—, and k1 represents an integer of 1 to 7, $R^{a4}$ and $R^{a5}$ each independently represent a hydrogen atom or a methyl group, $R^{a6}$ and $R^{a7}$ each independently represent a C1-C10 aliphatic hydrocarbon group, m1 represents an integer of 0 to 14, and n1 represents an integer of 0 to 10.

9. The photoresist composition according to claim 1, 2 or 3, wherein the resin further comprises a hydroxyadamantan-1-yl group-containing structural unit.

10. The photoresist composition according to claim 1, 2 or 3, which further comprises a resin comprising a structural unit represented by formula (a4-1):

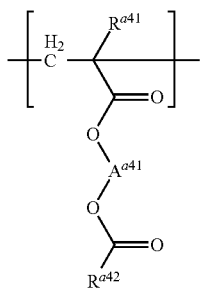

(a4-1)

wherein $R^{a41}$ represents a C6-C12 monovalent aromatic hydrocarbon group, or a C1-C12 monovalent aliphatic hydrocarbon group in which a methylene group may be replaced by an oxygen atom or a carbonyl group, $A^{a41}$ represents a C1-C6 alkanediyl group, or a moiety represented by formula (a-g1):

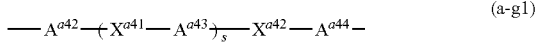

(a-g1)

in which s represents 0 or 1, $A^{a42}$ and $A^{a44}$ respectively represent a C1-C5 aliphatic hydrocarbon group which may have a substituent, $A^{a43}$ represents a single bond or a C1-C5 aliphatic hydrocarbon group which may have a substituent, $X^{a41}$ and $X^{a42}$ respectively represent —O—, —CO—, —CO—O—, or —O—CO—, the total number of carbon atoms of $A^{a42}$, $A^{a43}$, $A^{a44}$, $X^{a41}$ and $X^{a42}$ is not more than 6, $R^{a42}$ represents an aliphatic hydrocarbon group which may have a substituent.

11. The photoresist composition according to claim 1, 2 or 3, which further comprises a basic compound.

12. A process for producing a photoresist pattern comprising the following steps (1) to (5):

(1) a step of applying the photoresist composition according to claim 1, 2 or 3 on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

* * * * *